United States Patent [19]

Hall et al.

[11] Patent Number: 6,027,912
[45] Date of Patent: *Feb. 22, 2000

[54] GENE ENCODING AN INVERTEBRATE ALPHA1 CALCIUM CHANNEL SUBUNIT

[75] Inventors: Linda M. Hall, Williamsville; Dejian Ren, Buffalo, both of N.Y.; Wei Zheng, Lafeyette, Calif.; Manuel Marcel Paul Dubald, Chapel Hill, N.C.

[73] Assignee: The Research Foundation of State University of New York, Amherst, N.Y.

[ * ] Notice: This patent is subject to a terminal disclaimer.

[21] Appl. No.: 08/374,077

[22] Filed: Jan. 19, 1995

[51] Int. Cl.⁷ .............................. C12N 1/21; C12N 15/12; C12N 15/63; C12P 21/02
[52] U.S. Cl. ................ 435/69.1; 435/252.3; 435/254.11; 435/320.1; 435/325; 536/23.5
[58] Field of Search ........................ 536/23.5; 435/69.1, 435/320.1, 240.2, 252.3, 254.11, 325

[56] References Cited

PUBLICATIONS

Pelzer et al., EMBO J. 8:2365–2371 (1989).
Williams et al., Neuron 8: 71–84 (1992).
Grabner et al., FEBS Letters 339:189–194 (1994).
Matthews et al., Soc. Neuroscience Abstr. 20:69 (1994).
Zheng et al., Soc. Neuroscience Abstr. 18:1138 (1992).
Grabner et al., J. Biol. Chem. 269(38):23668–23674, 1994.
Snutch et al., "Rat brain expresses a heterogeneous family of calcium channels", Proc. Natl. Acad. Sci. USA, (1990) 87:3391–3395.
Snutch et al., "distinct Calcium Channels Are Generated by Alternative Splicing and Are Differentially Expressed in the Mammalian CNS", Neuron, (1991) 7:45–57.
Hui et al., "Molecular Cloning of Multiple Subtypes of a Novel Rat Brain Isoform of the $\alpha_1$ Subunit of the Voltage–Dependent Calcium Channel", Neuron, (1991) 7:35–44.
Starr et al., "Primary structure of a calcium channel that is highly expressed in the rat cerebellum", Proc. Natl. Acad. Sci. USA, (1991) 88:5621–5625.
Dubel et al., "Molecular cloning of the $\alpha_1$ subunit of an ω–conotoxin–sensitive calcium channel", Proc. Natl. Acad. Sci. USA, (1992) 89:5058–5062.
Soong et al., "Structure and Functional Expression of a Member of the Low–Voltage–Activated Calcium Channel Family", Science, (1993) 260:1133–1136.
Biel et al., "Primary structure and functional expression of a high voltage activated calcium channel from rabbit lung", FEBS Lett., (1990) 269:409–412.
Koch et al., "cDNA Cloning of a Dihydropyridine–sensitive Calcium Channel from Rat Aorta", J. Biol. Chem., (1990) 265:17786–17791.
Perez–Reyes et al., "Molecular Diversity of L–type Calcium Channels", J. Biol. Chem., (1990) 265:20430–20436.
Williams et al., "Structure and Functional Expression of an ω–Conotoxin–Sensitive Human N–Type Calcium Channel", Science, (1992a) 257:389–395.

ffrench–Constant et al., "Molecular cloning and transformation of cyclodiene resistance in Drosophila: An invertebrate γ–aminobutyric acid subtype A receptor locus", Proc Natl. Acad. Sci. USA, (1991) 88:7209–7213.
ffrench–Constant et al., "A point mutation in a Drosphila GABA receptor confers insecticide resistance", Nature, (1993) 363:449–451.
Harvey et al., "Sequence of a functional invertebrate $GABA_a$ receptor subunit which can form a chimeric receptor with a vertebrate α subunit", EMBO J., (1991) 10:3239–3245.
Ruth et al., "Primary Structure of the β Subunit of the DHP–Sensitive Calcium Channel from Skeletal Muscle", Science, (1989) 245:1115–1118.
Pragnell et al., "Calcium channel β–subunit binds to a conserved motif in the I–II cytoplasmic linker of the $\alpha_1$–subunit", Nature (1994) 368:67–70.
Tanabe et al., "Primary structure of the receptor for calcium channel blockers from skeletal muscle", Nature, (1987) 328:313–318.
Mikami et al., "Primary structure and functional expression of the cardiac dihydropyridine–sensitive calcium channel", Nature, (1989) 340:230–233.
Mori et al., "Primary structure and functional expression from complementary DNA of a brain calcium channel", Nature, (1991) 350:398–402.
Gragner et al, "Calcium channels from *Cyprinus carpio* skeletal muscle", Proc. Natl. Acad. Sci. USA, (1991) 88:727–731.
Martin et al., "Base pairing involving deoxyinosine: implications for probe design", Nucleic Acids Res., (1985) 13:8927.
Knoth et al., "Highly degenerate, inosine–containing primers specifically amplify rare cDMA using the polymerase chain reaction", Nucleic Acids Res., (1988) 16:11932.
Pauron et al., "Identification and affinity Labeling of Very High Affinity Binding Sites for the Phenylalkylamine Series of $Ca^+$ Channel Blockers in the Drosophila Nervous System", Biochemistry, (1987) 26:6311–6315.
Greenberg et al., "Native and Detergent–Solubilized Membrane Extracts From Drosophila Heads Contain Binding Sites for Phenylalkylamine Calcium Channel Blockers", Insect Biochem., (1989) 19:309–322.
Glossmann et al., "Very high affinity interaction of DPI 201–106 and BDF 8784 enantiomers with the phenylalkylamine–sensitive $Ca^{2+}$–channel in Drosophila head membranes", Br. J. Pharmacol., (1991) 102:446–452.
Babitch, J., "Channel Hands", Nature, (1989) 346:321–322.
Stühmer et al., Structural parts involved in activation and inactivation of the sodium channel, Nature, (1989) 339:597–603.

(List continued on next page.)

Primary Examiner—Eric Grimes
Attorney, Agent, or Firm—Burns, Doane, Swecker & Mathis, L.L.P.

[57] ABSTRACT

The present invention provides for the isolation and characterization of a calcium channel al subunit gene cloned from Drosophila melanogaster, and designated "DmcalD".

12 Claims, 13 Drawing Sheets

OTHER PUBLICATIONS

Tufty, R. M. and Kretsinger, R. H. "Troponin and Parvalbumin Calcium Binding Regions Predicted in Myosin Light Chain and T4 Lysozyme", *Science,* (1975) 187:167–169.

Tang et al., "Molecular Localization of Ion Selectivity Sites within the Pore of a Human L–type cardiac Calcium Channel", *J. Biol. Chem.,* (1993) 268:13026–13029.

Tanabe et al., "Regions of the skeletal muscle dihydropyridine receptor critical for excitation–contraction coupling", *Nature,* (1990) 346:567–569.

Striessnig et al., "Identification of a phenylalkylamine binding region withIN the α1 subunit of skeletal muscle $Ca^{2+}$ channels", *Proc. Natl. Acad. Sci. USA,* (1990) 87:9108–9112.

Nakayama et al., "Identification of 1,4–dihydropyridine binding regions within the α1 subunit of skeletal muscle $Ca^{2+}$ channels by protaffinity labeling with diazipine", *Proc. Natl. Acad. Sci. USA,* (1991) 88:9203–9207.

Striessnig et al., Dihydropyridine receptor of L–type $Ca^{2+}$ channels: Identification of binding domains for [3H](+)–PN200–110 and [3H]azidopine within the α1 subunit, *Proc. Natl. Acad. Sci. USA,* (1991) 88:10769–10773.

Catterall, W. A. and Striessnig, J., "Receptor sites for $Ca^{2+}$ channel antagonists", *TIPS,* (1992) 13:256–262.

J. R. Thackery and B. Ganetzky, "developmentally Regulated Alternative Splicing Generates a Complex Array of *Drosophila para* Sodium Channel Isoforms", *J. Neurosci,* (1994) 14:2569–2578.

Hullin et al, "Calcium channel β subunit heterogeneity: functional expression of cloned cDNA from heart, aorta and brain", *EMBO J.* (1992) 11:885–890.

Pragnell et al., "Cloning and tissue–specific expression of the brain calcium channel β–subunit" *FEBS Lett.* (1991) 291:253–258.

| | | | | | |
|---|---|---|---|---|---|
|MGGGELVNCI|AYDDNTLVIE|RKPSPSSPST|SRRYLKAETP|TRGSRKYNRK|50|
|SSAKSDLEVV|VVKPEHHHQH|RSPTITLPVP|ANPLTTSASA|GSSPTGAGLA|100|
|AGLGTASGTV|LQQSCSALDP|PEDSNQPSGT|RRRATSTELA|LSNVTSQIVN|150|
|NATYKLDFKQ|RRHKSNNGGS|ESGSLTGIAT|GPATSPAGPT|GPTSSSGKRR|200|
|KSSCTSCGGG|GISAPPPRLT|PEEAWQLQPQ|NSVTSAGSTN|SSFSSGGGRD|250|
|DNSSYSAVGG|DSSSSNSCNC|DITGDNSTLH|GLGVGDVCSF|IADCDDNSED|300|
|DDGDPNNQDL|SSQTLRTAAI|VAAVAAAAKE|QAQEQSLADC|ESFSDRRQDA|350|
|DEDVRIIQDC|CGGNNDSLED|VGEVDDNADV|VVRKNSRNRP|SIRRTCRITE|400|
|EDDDEDENAD|YGDFDREDQE|LDDEEPEGTT|IDIDEQEQQH|DQGDSAEEED|450|
|DDEDVDEYFE|EEEDDTQAFS|PFYSSSAELI|DNFGGGAGKF|FNIMDFERGA|500|
|SGEGGFSPNG|NGGPGSGDVS|RTARYDSGEG|DLGGGNNIMG|IDSMGIANIP|550|
|ETMNGTTIGP|SGAGGQKGGA|AAGAAGQKRQ|QRRGKPQPDR|PQRALFCLSV|600|
|KNPLRALCIR|IVEWKPFEFL|ILLTIFANCI|ALAVYTPYPG|SDSNVTNQTL|650|
|EKVEYVFLVI|FTAECVMKIL|AYGFVLHDGA|YLGNGWNLLD|FTIVVMGAIS|700|
|TALSQLMKDA|FDVKALRAFR|VLRPLRLVSG|VPSLQVVLNS|ILKAMVPLFH|750|
|IALLVLFVII|IYAIIGLELF|SGKLHKACRD|EITGEYEENI|RPCGVGYQCP|800|
|PGYKCYGGWD|GPNDGITNFD|NFGLAMLTVF|QCVTLEGWTD|VLYSIQDAMG|850|
|SDWQWMYFIS|MVILGAFFVM|NLILGVLSGE|FSKERNKAKN|RGDFQKLREK|900|
|QQIEEDLRGY|LDWITQAEDI|EPDAVGGLIS|DGKGKQPNEM|DSTENLGEEM|950|
|PEVQMTESRW|RKMKKDFDRV|NRRMRRACRK|AVKSQAFYWL|IIVLVFLNTG|1000|
|VLATEHYGQL|DWLDNFQEYT|NVFFIGLFTC|EMLLKMYSLG|FQGYFVSLFN|1050|
|RFDCFVVIGS|ITETLLTNTG|MMPPLGVSVL|RCVRLLRVFK|VTKYWRSLSN|1100|
|LVASLLNSIQ|SIASLLLLLF|LFIVIFALLG|MQVFGGKFNF|DGKEEKYRMN|1150|
|FDCFWQALLT|VFQIMTGEDW|NAVMYVGINA|YGGVSSYGAL|ACIYFIILFI|1200|
|CGNYILLNVF|LAIAVDNLAD|ADSLSEVEKE|EEPHDESAQK|KSHSPTPTID|1250|
|GMDDHLSIDI|DMEQQELDDE|DKMDHETLSD|EEVREMCEEE|EEVDEEGMIT|1300|
|ARPRRMSEVN|TATKILPIPP|GTSFFLFSQT|NRFRVFCHWL|CNHSNFGNII|1350|
|LCCIMFSSAM|LAAENPLRAN|DDLNKVLNKF|DYFFTAVFTM|ELILKLISYG|1400|
|FVLHDGAFCR|SAFNLLDLLV|VCVSLISLVS|SSDAISVVKI|LRVLRVLRPL|1450|
|RAINRAKGLK|HVVQCVIVAV|KTIGNIVLVT|CLLQFMFAVI|GVQLFKGKFF|1500|
|KCTDGSKMTQ|DECYGTYLVY|DDGDVHKPRL|REREWSNNRF|HFDDVAKGML|1550|
|TLFTVSTFEG|WPGLLYVSID|SNKENGGPIH|NFRPIVAAYY|IIYIIIIAFF|1600|
|MVNIFVGFVI|VTFQNEGEQE|YKNCDLDKNQ|RNCIEFALKA|KPVRRYIPKH|1650|
|GIQYKVWWFV|TSSSFEYTIF|ILIMINTVTL|AMKFYNQPLW|YTELLDALNM|1700|
|IFTAVFALEF|VFKLAAFRFK|NYFGDAWNVF|DFIIVLGSFI|DIVYSEIKSK|1750|
|DTSQIAECDI|VEGCKSTKKS|AGSNLISINF|FRLFRVMRLV|KLLSKGEGIR|1800|
|TLLWTFIKSF|QALPYVALLI|VLLFFIYAVV|GMQVFGKIAL|DGGNAITANN|1850|
|NFQTFQQAVL|VLFRSATGEA|WQEIMMSCSA|QPDVKCDMNS|DTPGEPCGSS|1900|
|IAYPYFISFY|VLCSFLIINL|FVAVIMDNFD|YLTRDWSILG|PHHLDEFIRL|1950|
|WSEYDPDAKG|RIKHLDVVTL|LRKISPPLGF|GKLCPHRMAC|KRLVSMNMPL|2000|
|NSDGTVLFNA|TLFAVVRTSL|SIKTDGNIDD|ANSELRATIK|QIWKRTNPKL|2050|
|LDQVVPPPGN|DDEVTVGKFY|ATYLIQDYFR|RFKKRKEQEG|KEGHPDSNTV|2100|
|TLQAGLRTLH|EVSPALKRAI|SGNLDELDQE|PEPMHRRHHT|LFGSVWSSIR|2150|
|RHGNGTFRRS|AKATASQSNG|ALAIGGSASA|ALGVGGSSLV|LGSSDPAGGD|2200|
|YLYDTLNRSV|ADGVNNITRN|IMQARLAAAG|KLQDELQGAG|SGGELRTFGE|2250|
|SISMRPLAKN|GGGAATVAGT|LPPEANAINY|DNRNRGILLH|PYNNVYAPNG|2300|
|ALPGHERMIQ|STPASPYDQR|RLPTSSDMNG|LAESLIGGVL|AAEGLGKYCD|2350|
|SEFVGTAARE|MREALDMTPE|EMNLAAHQIL|SNEHSLSLIG|SSNGSIFGGS|2400|
|AGGLGGAGSG|GVGGLGGSSS|IRNAFGGSGS|GPSSLSPQHQ|PYSGTLNSPP|2450|
|IPDNRLRRVA|TVTTTNNNNK|SQVSQNNSSS|LNVRANANSQ|MNMSPTGQPV|2500|
|QQQSPLRGQG|NQTYSSX| | | |2517|

SEQUENCE LISTING (1) GENERAL INFORMATION:

(iii) NUMBER OF SEQUENCES: 57

(2) INFORMATION FOR SEQ ID NO:1:

(i) SEQUENCE CHARACTERISTICS:
       (A) LENGTH: 8075 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 157..7704

(xi) SEQUENCE DESCRIPTION: SEQ ID NO:1:

```
GGTCATCATT GGCTCTCAGA GGATTCTCTG CTGCCAACAT AGCCGATGAA AACATAATGC        60

AACACAGAAT AATGTTGCCG AAATTGCTGT GATTGCAAAG CCTCGACCTC GACCTCAACC       120

TCGACCTCCG CCTCCACCAC CACCACGAAT ACTGTG ATG GGT GGC GGG GAG CTG        174
                                        Met Gly Gly Gly Glu Leu
                                          1               5

GTG AAC TGT ATA GCC TAC GAT GAC AAC ACC CTG GTC ATC GAG AGG AAA        222
Val Asn Cys Ile Ala Tyr Asp Asp Asn Thr Leu Val Ile Glu Arg Lys
         10                  15                  20

CCC TCG CCC TCC TCC CCG TCC ACC AGC CGG CGT TAT CTG AAG GCC GAA        270
Pro Ser Pro Ser Ser Pro Ser Thr Ser Arg Arg Tyr Leu Lys Ala Glu
     25                  30                  35

ACG CCG ACG CGT GGC AGT CGA AAG TAC AAC CGC AAG TCA TCG GCT AAA        318
Thr Pro Thr Arg Gly Ser Arg Lys Tyr Asn Arg Lys Ser Ser Ala Lys
 40                  45                  50

AGT GAT TTG GAA GTG GTC GTT GTC AAG CCG GAA CAC CAT CAT CAG CAT        366
Ser Asp Leu Glu Val Val Val Val Lys Pro Glu His His His Gln His
 55                  60                  65                  70

CGA TCT CCG ACG ATA ACG CTT CCG GTT CCG GCT AAC CCA CTA ACC ACA        414
Arg Ser Pro Thr Ile Thr Leu Pro Val Pro Ala Asn Pro Leu Thr Thr
                 75                  80                  85

TCG GCA TCG GCG GGA TCC TCG CCC ACG GGA GCG GGA TTG GCA GCC GGA        462
Ser Ala Ser Ala Gly Ser Ser Pro Thr Gly Ala Gly Leu Ala Ala Gly
             90                  95                 100

TTG GGA ACT GCC TCG GGA ACG GTC CTG CAA CAA AGC TGC AGT GCA CTT        510
Leu Gly Thr Ala Ser Gly Thr Val Leu Gln Gln Ser Cys Ser Ala Leu
         105                 110                 115

GAT CCG CCC GAG GAT TCG AAT CAG CCC AGC GGG ACC AGG AGG CGA GCC        558
Asp Pro Pro Glu Asp Ser Asn Gln Pro Ser Gly Thr Arg Arg Arg Ala
 120                 125                 130

ACC AGC ACC GAG CTC GCC CTC AGC AAC GTC ACC AGT CAG ATT GTG AAC        606
Thr Ser Thr Glu Leu Ala Leu Ser Asn Val Thr Ser Gln Ile Val Asn
135                 140                 145                 150

AAT GCC ACC TAC AAG CTA GAC TTC AAG CAA CGT CGT CAC AAA AGC AAC        654
Asn Ala Thr Tyr Lys Leu Asp Phe Lys Gln Arg Arg His Lys Ser Asn
                 155                 160                 165

AAC GGA GGC AGT GAG TCA GGA TCT CTA ACC GGA ATA GCC ACA GGA CCG        702
Asn Gly Gly Ser Glu Ser Gly Ser Leu Thr Gly Ile Ala Thr Gly Pro
             170                 175                 180

GCG ACA AGT CCC GCA GGA CCA ACA GGA CCA ACC AGT TCC AGC GGC AAG        750
Ala Thr Ser Pro Ala Gly Pro Thr Gly Pro Thr Ser Ser Ser Gly Lys
         185                 190                 195
```

```
CGG CGC AAG TCC AGT TGC ACA TCC TGC GGC GGA GGT GGC ATC AGT GCC        798
Arg Arg Lys Ser Ser Cys Thr Ser Cys Gly Gly Gly Gly Ile Ser Ala
        200             205             210

CCA CCC CCG AGA CTA ACG CCC GAG GAG GCG TGG CAA CTG CAA CCA CAG        846
Pro Pro Pro Arg Leu Thr Pro Glu Glu Ala Trp Gln Leu Gln Pro Gln
215             220             225             230

AAC AGT GTT ACC AGT GCC GGC AGC ACA AAT AGT AGT TTC AGC AGC GGC        894
Asn Ser Val Thr Ser Ala Gly Ser Thr Asn Ser Ser Phe Ser Ser Gly
                235             240             245

GGC GGA CGC GAC GAT AAT AGT AGT TAC AGT GCC GTC GGC GGC GAT AGC        942
Gly Gly Arg Asp Asp Asn Ser Ser Tyr Ser Ala Val Gly Gly Asp Ser
            250             255             260

AGC AGC AGC AAT AGT TGC AAC TGC GAT ATC ACC GGT GAT AAC AGT ACA        990
Ser Ser Ser Asn Ser Cys Asn Cys Asp Ile Thr Gly Asp Asn Ser Thr
        265             270             275

TTG CAT GGT TTG GGC GTC GGC GAC GTT TGT AGT TTC ATC GCC GAT TGT       1038
Leu His Gly Leu Gly Val Gly Asp Val Cys Ser Phe Ile Ala Asp Cys
    280             285             290

GAC GAC AAT AGC GAG GAC GAC GAC GGC GAT CCG AAT AAC CAG GAT CTC       1086
Asp Asp Asn Ser Glu Asp Asp Asp Gly Asp Pro Asn Asn Gln Asp Leu
295             300             305             310

AGC TCG CAA ACC CTG CGC ACA GCG GCC ATC GTA GCG GCA GTT GCG GCA       1134
Ser Ser Gln Thr Leu Arg Thr Ala Ala Ile Val Ala Ala Val Ala Ala
                315             320             325

GCA GCC AAG GAA CAG GCC CAG GAG CAA TCG CTC GCC GAC TGC GAG AGC       1182
Ala Ala Lys Glu Gln Ala Gln Glu Gln Ser Leu Ala Asp Cys Glu Ser
            330             335             340

TTC AGC GAT CGC CGG CAG GAT GCC GAT GAG GAC GTC CGC ATC ATT CAG       1230
Phe Ser Asp Arg Arg Gln Asp Ala Asp Glu Asp Val Arg Ile Ile Gln
        345             350             355

GAT TGC TGC GGC GGC AAC AAC GAC TCA CTC GAA GAC GTT GGC GAG GTG       1278
Asp Cys Cys Gly Gly Asn Asn Asp Ser Leu Glu Asp Val Gly Glu Val
    360             365             370

GAC GAC AAC GCC GAC GTT GTC GTG AGA AAG AAC TCA AGG AAT CGT CCC       1326
Asp Asp Asn Ala Asp Val Val Val Arg Lys Asn Ser Arg Asn Arg Pro
375             380             385             390

TCG ATC AGA AGG ACA TGC AGG ATA ACC GAG GAG GAC GAC GAC GAG GAC       1374
Ser Ile Arg Arg Thr Cys Arg Ile Thr Glu Glu Asp Asp Asp Glu Asp
                395             400             405

GAG AAC GCG GAC TAC GGT GAT TTC GAT CGG GAG GAT CAA GAG CTA GAC       1422
Glu Asn Ala Asp Tyr Gly Asp Phe Asp Arg Glu Asp Gln Glu Leu Asp
            410             415             420

GAC GAG GAG CCC GAG GGC ACC ACC ATT GAC ATT GAT GAG CAG GAA CAG       1470
Asp Glu Glu Pro Glu Gly Thr Thr Ile Asp Ile Asp Glu Gln Glu Gln
        425             430             435

CAG CAC GAC CAA GGT GAT TCC GCT GAA GAG GAA GAC CAC GAC GAG GAC       1518
Gln His Asp Gln Gly Asp Ser Ala Glu Glu Glu Asp His Asp Glu Asp
    440             445             450

GTC GAC GAG TAC TTT GAG GAG GAG GAG GAC GAC ACG CAG GCC TTT TCG       1566
Val Asp Glu Tyr Phe Glu Glu Glu Glu Asp Asp Thr Gln Ala Phe Ser
455             460             465             470

CCA TTC TAC TCC AGT TCC GCG GAG CTA ATT GAT AAT TTT GGT GGC GGT       1614
Pro Phe Tyr Ser Ser Ser Ala Glu Leu Ile Asp Asn Phe Gly Gly Gly
                475             480             485

GCG GGC AAG TTC TTC AAC ATA ATG GAC TTC GAG CGT GGA GCC TCC GGC       1662
Ala Gly Lys Phe Phe Asn Ile Met Asp Phe Glu Arg Gly Ala Ser Gly
            490             495             500

GAG GGA GGC TTT TCG CCA AAC GGC AAC GGT GGT CCC GGC AGC GGT GAT       1710
Glu Gly Gly Phe Ser Pro Asn Gly Asn Gly Gly Pro Gly Ser Gly Asp
```

-continued

|  |  |  |  |  |  |  |  |  |  |  |  |  |  |  |  |
|---|---|---|---|---|---|---|---|---|---|---|---|---|---|---|---|
|  |  | 505 |  |  |  |  | 510 |  |  |  |  | 515 |  |  |  |
| GTT | TCC | CGT | ACG | GCG | AGA | TAC | GAC | TCC | GGG | GAG | GGG | GAT | CTG | GGC | GGC | 1758 |
| Val | Ser | Arg | Thr | Ala | Arg | Tyr | Asp | Ser | Gly | Glu | Gly | Asp | Leu | Gly | Gly |
|  |  | 520 |  |  |  |  | 525 |  |  |  |  | 530 |  |  |  |
| GGC | AAC | AAT | ATC | ATG | GGC | ATC | GAT | TCT | ATG | GGC | ATT | GCA | AAC | ATT | CCG | 1806 |
| Gly | Asn | Asn | Ile | Met | Gly | Ile | Asp | Ser | Met | Gly | Ile | Ala | Asn | Ile | Pro |
| 535 |  |  |  |  | 540 |  |  |  |  | 545 |  |  |  |  | 550 |
| GAA | ACC | ATG | AAC | GGC | ACC | ACA | ATT | GGA | CCA | AGT | GGA | GCC | GGT | GGC | CAA | 1854 |
| Glu | Thr | Met | Asn | Gly | Thr | Thr | Ile | Gly | Pro | Ser | Gly | Ala | Gly | Gly | Gln |
|  |  |  |  | 555 |  |  |  |  | 560 |  |  |  |  | 565 |  |
| AAA | GGT | GGT | GCT | GCT | GCA | GGT | GCC | GCT | GGC | CAA | AAG | AGA | CAA | CAA | CGC | 1902 |
| Lys | Gly | Gly | Ala | Ala | Ala | Gly | Ala | Ala | Gly | Gln | Lys | Arg | Gln | Gln | Arg |
|  |  |  | 570 |  |  |  |  | 575 |  |  |  |  | 580 |  |  |
| CGT | GGA | AAA | CCG | CAA | CCA | GAC | AGA | CCA | CAA | CGA | GCA | TTA | TTT | TGC | CTG | 1950 |
| Arg | Gly | Lys | Pro | Gln | Pro | Asp | Arg | Pro | Gln | Arg | Ala | Leu | Phe | Cys | Leu |
|  |  | 585 |  |  |  |  | 590 |  |  |  |  | 595 |  |  |  |
| AGC | GTC | AAG | AAT | CCC | CTG | CGA | GCC | CTG | TGC | ATT | CGC | ATT | GTG | GAG | TGG | 1998 |
| Ser | Val | Lys | Asn | Pro | Leu | Arg | Ala | Leu | Cys | Ile | Arg | Ile | Val | Glu | Trp |
|  |  | 600 |  |  |  |  | 605 |  |  |  |  | 610 |  |  |  |
| AAA | CCA | TTT | GAG | TTC | CTT | ATT | TTG | TTA | ACC | ATT | TTT | GCC | AAC | TGT | ATT | 2046 |
| Lys | Pro | Phe | Glu | Phe | Leu | Ile | Leu | Leu | Thr | Ile | Phe | Ala | Asn | Cys | Ile |
| 615 |  |  |  |  | 620 |  |  |  |  | 625 |  |  |  |  | 630 |
| GCC | TTG | GCG | GTT | TAC | ACC | CCT | TAT | CCG | GGA | AGC | GAT | TCA | AAC | GTG | ACG | 2094 |
| Ala | Leu | Ala | Val | Tyr | Thr | Pro | Tyr | Pro | Gly | Ser | Asp | Ser | Asn | Val | Thr |
|  |  |  |  | 635 |  |  |  |  | 640 |  |  |  |  | 645 |  |
| AAT | CAA | ACC | TTG | GAA | AAA | GTT | GAA | TAT | GTA | TTC | CTA | GTT | ATA | TTC | ACA | 2142 |
| Asn | Gln | Thr | Leu | Glu | Lys | Val | Glu | Tyr | Val | Phe | Leu | Val | Ile | Phe | Thr |
|  |  |  | 650 |  |  |  |  | 655 |  |  |  |  | 660 |  |  |
| GCG | GAA | TGT | GTT | ATG | AAA | ATT | TTA | GCA | TAT | GGT | TTT | GTG | TTA | CAT | GAT | 2190 |
| Ala | Glu | Cys | Val | Met | Lys | Ile | Leu | Ala | Tyr | Gly | Phe | Val | Leu | His | Asp |
|  |  | 665 |  |  |  |  | 670 |  |  |  |  | 675 |  |  |  |
| GGT | GCA | TAT | CTG | GGA | AAT | GGA | TGG | AAT | TTA | TTA | GAT | TTT | ACA | ATT | GTA | 2238 |
| Gly | Ala | Tyr | Leu | Gly | Asn | Gly | Trp | Asn | Leu | Leu | Asp | Phe | Thr | Ile | Val |
|  | 680 |  |  |  |  | 685 |  |  |  |  | 690 |  |  |  |  |
| GTT | ATG | GGG | GCG | ATA | AGT | ACT | GCA | CTC | TCC | CAA | TTG | ATG | AAG | GAC | GCC | 2286 |
| Val | Met | Gly | Ala | Ile | Ser | Thr | Ala | Leu | Ser | Gln | Leu | Met | Lys | Asp | Ala |
| 695 |  |  |  |  | 700 |  |  |  |  | 705 |  |  |  |  | 710 |
| TTT | GAT | GTG | AAG | GCT | CTA | CGT | GCC | TTT | CGA | GTG | CTA | CGT | CCA | CTG | CGA | 2334 |
| Phe | Asp | Val | Lys | Ala | Leu | Arg | Ala | Phe | Arg | Val | Leu | Arg | Pro | Leu | Arg |
|  |  |  | 715 |  |  |  |  | 720 |  |  |  |  | 725 |  |  |
| CTT | GTA | TCG | GGT | GTA | CCA | AGT | CTA | CAG | GTT | GTG | CTG | AAT | TCA | ATT | TTA | 2382 |
| Leu | Val | Ser | Gly | Val | Pro | Ser | Leu | Gln | Val | Val | Leu | Asn | Ser | Ile | Leu |
|  |  | 730 |  |  |  |  | 735 |  |  |  |  | 740 |  |  |  |
| AAG | GCC | ATG | GTG | CCA | CTG | TTT | CAC | ATT | GCA | CTC | CTG | GTC | CTA | TTC | GTA | 2430 |
| Lys | Ala | Met | Val | Pro | Leu | Phe | His | Ile | Ala | Leu | Leu | Val | Leu | Phe | Val |
|  | 745 |  |  |  |  | 750 |  |  |  |  | 755 |  |  |  |  |
| ATC | ATA | ATC | TAT | GCG | ATA | ATT | GGC | CTA | GAG | CTC | TTC | TCT | GGC | AAA | TTG | 2478 |
| Ile | Ile | Ile | Tyr | Ala | Ile | Ile | Gly | Leu | Glu | Leu | Phe | Ser | Gly | Lys | Leu |
|  | 760 |  |  |  |  | 765 |  |  |  |  | 770 |  |  |  |  |
| CAC | AAG | GCG | TGT | CGC | GAT | GAG | ATC | ACA | GGT | GAA | TAC | GAG | GAA | AAC | ATC | 2526 |
| His | Lys | Ala | Cys | Arg | Asp | Glu | Ile | Thr | Gly | Glu | Tyr | Glu | Glu | Asn | Ile |
| 775 |  |  |  |  | 780 |  |  |  |  | 785 |  |  |  |  | 790 |
| CGG | CCC | TGC | GGA | GTG | GGC | TAC | CAG | TGT | CCG | CCG | GGC | TAC | AAG | TGC | TAC | 2574 |
| Arg | Pro | Cys | Gly | Val | Gly | Tyr | Gln | Cys | Pro | Pro | Gly | Tyr | Lys | Cys | Tyr |
|  |  |  |  | 795 |  |  |  |  | 800 |  |  |  |  | 805 |  |
| GGC | GGA | TGG | GAT | GGA | CCA | AAC | GAC | GGC | ATC | ACC | AAC | TTC | GAC | AAC | TTT | 2622 |
| Gly | Gly | Trp | Asp | Gly | Pro | Asn | Asp | Gly | Ile | Thr | Asn | Phe | Asp | Asn | Phe |
|  |  |  | 810 |  |  |  |  | 815 |  |  |  |  | 820 |  |  |
| GGC | CTG | GCC | ATG | TTG | ACG | GTG | TTC | CAG | TGC | GTC | ACC | CTT | GAG | GGC | TGG | 2670 |

```
Gly Leu Ala Met Leu Thr Val Phe Gln Cys Val Thr Leu Glu Gly Trp
            825                 830                 835

ACT GAT GTC CTT TAT AGC ATC CAA GAT GCA ATG GGC AGC GAT TGG CAG      2718
Thr Asp Val Leu Tyr Ser Ile Gln Asp Ala Met Gly Ser Asp Trp Gln
840                 845                 850

TGG ATG TAC TTC ATT TCC ATG GTT ATC CTG GGT GCC TTC TTC GTG ATG      2766
Trp Met Tyr Phe Ile Ser Met Val Ile Leu Gly Ala Phe Phe Val Met
855                 860                 865                 870

AAT CTG ATT CTC GGT GTG TTG TCC GGT GAG TTC TCC AAG GAG CGT AAC      2814
Asn Leu Ile Leu Gly Val Leu Ser Gly Glu Phe Ser Lys Glu Arg Asn
                875                 880                 885

AAG GCC AAA AAC CGC GGT GAC TTC CAG AAG CTG CGC GAG AAG CAG CAG      2862
Lys Ala Lys Asn Arg Gly Asp Phe Gln Lys Leu Arg Glu Lys Gln Gln
            890                 895                 900

ATC GAA GAG GAT CTG CGG GGC TAT CTC GAT TGG ATT ACC CAA GCC GAG      2910
Ile Glu Glu Asp Leu Arg Gly Tyr Leu Asp Trp Ile Thr Gln Ala Glu
        905                 910                 915

GAC ATT GAA CCA GAC GCC GTG GGA GGT CTG ATA TCC GAT GGC AAG GGC      2958
Asp Ile Glu Pro Asp Ala Val Gly Gly Leu Ile Ser Asp Gly Lys Gly
920                 925                 930

AAG CAG CCC AAC GAA ATG GAT TCC ACC GAG AAT CTG GGC GAA GAA ATG      3006
Lys Gln Pro Asn Glu Met Asp Ser Thr Glu Asn Leu Gly Glu Glu Met
935                 940                 945                 950

CCC GAG GTC CAA ATG ACT GAA TCA CGA TGG CGC AAA ATG AAG AAG GAC      3054
Pro Glu Val Gln Met Thr Glu Ser Arg Trp Arg Lys Met Lys Lys Asp
                955                 960                 965

TTC GAT CGA GTC AAT CGT CGA ATG CGA AGA GCC TGT CGC AAG GCA GTC      3102
Phe Asp Arg Val Asn Arg Arg Met Arg Arg Ala Cys Arg Lys Ala Val
            970                 975                 980

AAG TCG CAG GCC TTC TAT TGG CTC ATC ATC GTT TTG GTG TTT CTC AAT      3150
Lys Ser Gln Ala Phe Tyr Trp Leu Ile Ile Val Leu Val Phe Leu Asn
        985                 990                 995

ACG GGT GTC TTG GCC ACG GAG CAT TAT GGC CAA CTT GAT TGG CTA GAT      3198
Thr Gly Val Leu Ala Thr Glu His Tyr Gly Gln Leu Asp Trp Leu Asp
    1000                1005                1010

AAC TTC CAG GAG TAC ACC AAC GTG TTC TTC ATC GGA CTG TTC ACC TGC      3246
Asn Phe Gln Glu Tyr Thr Asn Val Phe Phe Ile Gly Leu Phe Thr Cys
1015                1020                1025                1030

GAA ATG TTG TTG AAG ATG TAC AGC TTG GGC TTT CAG GGC TAC TTC GTT      3294
Glu Met Leu Leu Lys Met Tyr Ser Leu Gly Phe Gln Gly Tyr Phe Val
            1035                1040                1045

TCG CTG TTC AAT CGT TTT GAT TGT TTT GTG GTG ATT GGC AGC ATT ACG      3342
Ser Leu Phe Asn Arg Phe Asp Cys Phe Val Val Ile Gly Ser Ile Thr
        1050                1055                1060

GAA ACC CTG CTA ACA AAC ACG GGA ATG ATG CCG CCA TTG GGT GTC TCC      3390
Glu Thr Leu Leu Thr Asn Thr Gly Met Met Pro Pro Leu Gly Val Ser
    1065                1070                1075

GTG CTG CGT TGT GTA CGT CTC CTG AGA GTC TTT AAA GTA ACT AAG TAC      3438
Val Leu Arg Cys Val Arg Leu Leu Arg Val Phe Lys Val Thr Lys Tyr
1080                1085                1090

TGG CGG TCT CTC TCA AAT CTC GTC GCT TCC CTA TTG AAC TCT ATA CAA      3486
Trp Arg Ser Leu Ser Asn Leu Val Ala Ser Leu Leu Asn Ser Ile Gln
1095                1100                1105                1110

TCG ATT GCT TCA CTT TTG TTA CTG CTC TTC CTA TTT ATT GTG ATA TTT      3534
Ser Ile Ala Ser Leu Leu Leu Leu Phe Leu Phe Ile Val Ile Phe
            1115                1120                1125

GCT TTG CTG GGC ATG CAA GTT TTT GGC GGT AAA TTT AAT TTT GAT GGC      3582
Ala Leu Leu Gly Met Gln Val Phe Gly Gly Lys Phe Asn Phe Asp Gly
        1130                1135                1140
```

```
AAA GAG GAG AAG TAT CGA ATG AAC TTC GAC TGC TTC TGG CAG GCT CTA         3630
Lys Glu Glu Lys Tyr Arg Met Asn Phe Asp Cys Phe Trp Gln Ala Leu
            1145                1150                1155

CTC ACA GTG TTT CAG ATC ATG ACT GGC GAG GAT TGG AAT GCT GTG ATG         3678
Leu Thr Val Phe Gln Ile Met Thr Gly Glu Asp Trp Asn Ala Val Met
    1160                1165                1170

TAT GTG GGC ATC AAT GCC TAT GGC GGT GTG TCC TCC TAT GGT GCC TTG         3726
Tyr Val Gly Ile Asn Ala Tyr Gly Gly Val Ser Ser Tyr Gly Ala Leu
1175                1180                1185                1190

GCC TGT ATT TAC TTT ATT ATT TTG TTC ATA TGC GGT AAC TAC ATC CTG         3774
Ala Cys Ile Tyr Phe Ile Ile Leu Phe Ile Cys Gly Asn Tyr Ile Leu
            1195                1200                1205

CTA AAC GTG TTC TTG GCC ATT GCT GTG GAT AAT TTG GCC GAT GCC GAC         3822
Leu Asn Val Phe Leu Ala Ile Ala Val Asp Asn Leu Ala Asp Ala Asp
    1210                1215                1220

TCG CTC TCT GAG GTC GAA AAA GAA GAG GAA CCT CAC GAT GAA TCT GCT         3870
Ser Leu Ser Glu Val Glu Lys Glu Glu Glu Pro His Asp Glu Ser Ala
            1225                1230                1235

CAG AAA AAG TCA CAT AGT CCG ACT CCA ACA ATT GAT GGC ATG GAT GAT         3918
Gln Lys Lys Ser His Ser Pro Thr Pro Thr Ile Asp Gly Met Asp Asp
1240                1245                1250

CAC CTC AGC ATA GAT ATC GAT ATG GAG CAA CAG GAA CTG GAT GAC GAA         3966
His Leu Ser Ile Asp Ile Asp Met Glu Gln Gln Glu Leu Asp Asp Glu
1255                1260                1265                1270

GAC AAA ATG GAC CAT GAA ACA TTA TCA GAC GAG GAA GTT CGT GAA ATG         4014
Asp Lys Met Asp His Glu Thr Leu Ser Asp Glu Glu Val Arg Glu Met
            1275                1280                1285

TGC GAG GAG GAA GAG GAA GTG GAT GAA GAA GGC ATG ATT ACA GCA CGA         4062
Cys Glu Glu Glu Glu Glu Val Asp Glu Glu Gly Met Ile Thr Ala Arg
    1290                1295                1300

CCC CGA CGT ATG TCT GAG GTT AAT ACG GCA ACG AAA ATT CTA CCC ATA         4110
Pro Arg Arg Met Ser Glu Val Asn Thr Ala Thr Lys Ile Leu Pro Ile
            1305                1310                1315

CCG CCG GGC ACA TCA TTT TTT CTT TTC TCA CAA ACG AAC AGA TTT CGC         4158
Pro Pro Gly Thr Ser Phe Phe Leu Phe Ser Gln Thr Asn Arg Phe Arg
1320                1325                1330

GTC TTC TGC CAC TGG CTT TGC AAT CAC AGC AAT TTC GGC AAC ATT ATT         4206
Val Phe Cys His Trp Leu Cys Asn His Ser Asn Phe Gly Asn Ile Ile
1335                1340                1345                1350

CTG TGT TGC ATT ATG TTT TCA TCG GCT ATG TTG GCA GCA GAG AAT CCT         4254
Leu Cys Cys Ile Met Phe Ser Ser Ala Met Leu Ala Ala Glu Asn Pro
            1355                1360                1365

CTG AGA GCC AAT GAT GAC CTG AAT AAA GTG CTC AAT AAA TTT GAT TAT         4302
Leu Arg Ala Asn Asp Asp Leu Asn Lys Val Leu Asn Lys Phe Asp Tyr
    1370                1375                1380

TTT TTC ACG GCA GTT TTC ACA ATG GAA CTG ATT CTG AAA TTG ATT TCA         4350
Phe Phe Thr Ala Val Phe Thr Met Glu Leu Ile Leu Lys Leu Ile Ser
            1385                1390                1395

TAC GGC TTC GTA TTA CAC GAC GGA GCC TTT TGC AGA TCC GCA TTT AAT         4398
Tyr Gly Phe Val Leu His Asp Gly Ala Phe Cys Arg Ser Ala Phe Asn
1400                1405                1410

CTA TTA GAT TTA CTT GTG GTC TGC GTG TCA TTG ATT TCT CTA GTG TCC         4446
Leu Leu Asp Leu Leu Val Val Cys Val Ser Leu Ile Ser Leu Val Ser
1415                1420                1425                1430

AGT TCG GAT GCG ATT TCA GTC GTG AAA ATT CTA CGT GTG CTC CGT GTT         4494
Ser Ser Asp Ala Ile Ser Val Val Lys Ile Leu Arg Val Leu Arg Val
            1435                1440                1445

TTA AGG CCA CTC AGA GCC ATT AAT CGT GCC AAG GGA CTG AAG CAT GTT         4542
Leu Arg Pro Leu Arg Ala Ile Asn Arg Ala Lys Gly Leu Lys His Val
    1450                1455                1460
```

```
-continued

GTT CAA TGT GTC ATA GTC GCT GTT AAG ACT ATC GGA AAT ATT GTG CTC        4590
Val Gln Cys Val Ile Val Ala Val Lys Thr Ile Gly Asn Ile Val Leu
        1465                1470                1475

GTC ACA TGC CTA CTG CAG TTC ATG TTT GCC GTA ATA GGA GTC CAA TTG        4638
Val Thr Cys Leu Leu Gln Phe Met Phe Ala Val Ile Gly Val Gln Leu
    1480                1485                1490

TTT AAG GGC AAA TTT TTC AAG TGC ACT GAT GGT TCC AAA ATG ACT CAA        4686
Phe Lys Gly Lys Phe Phe Lys Cys Thr Asp Gly Ser Lys Met Thr Gln
1495                1500                1505                1510

GAT GAA TGC TAC GGA ACC TAT CTG GTC TAT GAT GAT GGC GAT GTT CAT        4734
Asp Glu Cys Tyr Gly Thr Tyr Leu Val Tyr Asp Asp Gly Asp Val His
                1515                1520                1525

AAG CCG CGA CTC AGG GAA CGG GAA TGG AGT AAC AAT CGC TTC CAC TTC        4782
Lys Pro Arg Leu Arg Glu Arg Glu Trp Ser Asn Asn Arg Phe His Phe
            1530                1535                1540

GAT GAT GTG GCC AAG GGC ATG TTG ACT TTG TTC ACG GTG TCC ACA TTT        4830
Asp Asp Val Ala Lys Gly Met Leu Thr Leu Phe Thr Val Ser Thr Phe
        1545                1550                1555

GAG GGC TGG CCA GGT TTG CTG TAT GTT TCA ATT GAT TCG AAT AAG GAA        4878
Glu Gly Trp Pro Gly Leu Leu Tyr Val Ser Ile Asp Ser Asn Lys Glu
    1560                1565                1570

AAC GGC GGT CCA ATA CAC AAC TTC CGT CCG ATC GTA GCT GCC TAC TAT        4926
Asn Gly Gly Pro Ile His Asn Phe Arg Pro Ile Val Ala Ala Tyr Tyr
1575                1580                1585                1590

ATA ATC TAC ATT ATT ATT ATT GCC TTC TTC ATG GTG AAC ATA TTC GTC        4974
Ile Ile Tyr Ile Ile Ile Ile Ala Phe Phe Met Val Asn Ile Phe Val
                1595                1600                1605

GGT TTC GTT ATC GTC ACT TTC CAA AAT GAG GGT GAA CAG GAA TAT AAG        5022
Gly Phe Val Ile Val Thr Phe Gln Asn Glu Gly Glu Gln Glu Tyr Lys
            1610                1615                1620

AAT TGT GAT CTG GAT AAG AAT CAG CGC AAT TGC ATA GAA TTT GCC TTG        5070
Asn Cys Asp Leu Asp Lys Asn Gln Arg Asn Cys Ile Glu Phe Ala Leu
        1625                1630                1635

AAA GCG AAA CCC GTT AGA CGC TAT ATA CCA AAG CAT GGT ATA CAA TAT        5118
Lys Ala Lys Pro Val Arg Arg Tyr Ile Pro Lys His Gly Ile Gln Tyr
    1640                1645                1650

AAG GTC TGG TGG TTC GTC ACG TCG TCA TCC TTC GAG TAC ACA ATA TTC        5166
Lys Val Trp Trp Phe Val Thr Ser Ser Ser Phe Glu Tyr Thr Ile Phe
1655                1660                1665                1670

ATA CTG ATC ATG ATA AAC ACG GTA ACG CTG GCT ATG AAG TTT TAC AAT        5214
Ile Leu Ile Met Ile Asn Thr Val Thr Leu Ala Met Lys Phe Tyr Asn
                1675                1680                1685

CAG CCG CTG TGG TAC ACG GAA CTT TTA GAT GCC TTG AAT ATG ATA TTT        5262
Gln Pro Leu Trp Tyr Thr Glu Leu Leu Asp Ala Leu Asn Met Ile Phe
            1690                1695                1700

ACG GCG GTG TTT GCT TTG GAA TTT GTC TTT AAA TTA GCC GCG TTT CGA        5310
Thr Ala Val Phe Ala Leu Glu Phe Val Phe Lys Leu Ala Ala Phe Arg
        1705                1710                1715

TTT AAG AAC TAC TTT GGA GAT GCT TGG AAC GTA TTC GAT TTT ATC ATC        5358
Phe Lys Asn Tyr Phe Gly Asp Ala Trp Asn Val Phe Asp Phe Ile Ile
    1720                1725                1730

GTT TTA GGC AGT TTC ATT GAC ATT GTC TAC TCT GAA ATT AAG AGC AAG        5406
Val Leu Gly Ser Phe Ile Asp Ile Val Tyr Ser Glu Ile Lys Ser Lys
1735                1740                1745                1750

GAT ACT TCT CAG ATA GCA GAA TGT GAC ATT GTA GAG GGC TGC AAA TCC        5454
Asp Thr Ser Gln Ile Ala Glu Cys Asp Ile Val Glu Gly Cys Lys Ser
                1755                1760                1765

ACC AAG AAA TCA GCT GGT TCA AAT TTA ATA TCC ATC AAT TTC TTC CGA        5502
Thr Lys Lys Ser Ala Gly Ser Asn Leu Ile Ser Ile Asn Phe Phe Arg
```

-continued

```
                 1770                1775                1780
CTG TTC CGA GTT ATG CGA CTC GTC AAG CTT CTC AGC AAA GGC GAG GGC    5550
Leu Phe Arg Val Met Arg Leu Val Lys Leu Leu Ser Lys Gly Glu Gly
        1785                1790                1795

ATT CGA ACA TTA CTG TGG ACT TTT ATC AAA TCC TTC CAG GCA CTG CCC    5598
Ile Arg Thr Leu Leu Trp Thr Phe Ile Lys Ser Phe Gln Ala Leu Pro
    1800                1805                1810

TAC GTA GCC CTG CTA ATT GTG CTT CTA TTT TTC ATT TAT GCG GTT GTG    5646
Tyr Val Ala Leu Leu Ile Val Leu Leu Phe Phe Ile Tyr Ala Val Val
1815                1820                1825                1830

GGG ATG CAA GTG TTC GGC AAA ATT GCT CTA GAT GGT GGA AAC GCC ATC    5694
Gly Met Gln Val Phe Gly Lys Ile Ala Leu Asp Gly Gly Asn Ala Ile
            1835                1840                1845

ACG GCC AAT AAC AAT TTC CAA ACG TTC CAG CAG GCT GTT TTA GTA CTC    5742
Thr Ala Asn Asn Asn Phe Gln Thr Phe Gln Gln Ala Val Leu Val Leu
            1850                1855                1860

TTC CGA TCG GCC ACC GGA GAA GCT TGG CAG GAA ATT ATG ATG TCC TGC    5790
Phe Arg Ser Ala Thr Gly Glu Ala Trp Gln Glu Ile Met Met Ser Cys
        1865                1870                1875

TCG GCG CAA CCG GAT GTG AAG TGC GAT ATG AAT TCA GAT ACG CCG GGA    5838
Ser Ala Gln Pro Asp Val Lys Cys Asp Met Asn Ser Asp Thr Pro Gly
    1880                1885                1890

GAA CCA TGC GGT TCC TCA ATA GCC TAT CCG TAC TTT ATT TCC TTC TAT    5886
Glu Pro Cys Gly Ser Ser Ile Ala Tyr Pro Tyr Phe Ile Ser Phe Tyr
1895                1900                1905                1910

GTT CTC TGC TCG TTT TTG ATT ATT AAT CTT TTC GTG GCC GTC ATT ATG    5934
Val Leu Cys Ser Phe Leu Ile Ile Asn Leu Phe Val Ala Val Ile Met
            1915                1920                1925

GAC AAC TTT GAC TAT CTG ACT CGT GAT TGG TCG ATT TTG GGT CCC CAC    5982
Asp Asn Phe Asp Tyr Leu Thr Arg Asp Trp Ser Ile Leu Gly Pro His
            1930                1935                1940

CAC TTG GAC GAG TTT ATT CGC CTT TGG AGC GAA TAC GAT CCG GAT GCC    6030
His Leu Asp Glu Phe Ile Arg Leu Trp Ser Glu Tyr Asp Pro Asp Ala
        1945                1950                1955

AAG GGA CGC ATC AAA CAC TTG GAT GTG GTC ACA TTG CTG AGA AAG ATC    6078
Lys Gly Arg Ile Lys His Leu Asp Val Val Thr Leu Leu Arg Lys Ile
    1960                1965                1970

TCC CCA CCA CTT GGC TTC GGC AAA CTG TGT CCA CAT AGA ATG GCC TGC    6126
Ser Pro Pro Leu Gly Phe Gly Lys Leu Cys Pro His Arg Met Ala Cys
1975                1980                1985                1990

AAG CGA CTG GTT TCC ATG AAC ATG CCC CTC AAC TCA GAT GGA ACG GTT    6174
Lys Arg Leu Val Ser Met Asn Met Pro Leu Asn Ser Asp Gly Thr Val
            1995                2000                2005

CTC TTC AAT GCC ACA CTG TTT GCT GTG GTC CGC ACT TCG CTG AGC ATC    6222
Leu Phe Asn Ala Thr Leu Phe Ala Val Val Arg Thr Ser Leu Ser Ile
            2010                2015                2020

AAA ACT GAC GGT AAT ATC GAT GAT GCC AAC TCC GAG CTG CGC GCC ACT    6270
Lys Thr Asp Gly Asn Ile Asp Asp Ala Asn Ser Glu Leu Arg Ala Thr
        2025                2030                2035

ATC AAG CAG ATC TGG AAG CGT ACC AAT CCG AAG CTT CTG GAT CAG GTT    6318
Ile Lys Gln Ile Trp Lys Arg Thr Asn Pro Lys Leu Leu Asp Gln Val
    2040                2045                2050

GTT CCA CCG CCG GGC AAC GAT GAC GAG GTG ACC GTC GGC AAG TTC TAC    6366
Val Pro Pro Pro Gly Asn Asp Asp Glu Val Thr Val Gly Lys Phe Tyr
2055                2060                2065                2070

GCC ACA TAT CTA ATT CAG GAC TAC TTC CGG CGC TTC AAG AAG CGC AAG    6414
Ala Thr Tyr Leu Ile Gln Asp Tyr Phe Arg Arg Phe Lys Lys Arg Lys
            2075                2080                2085

GAA CAG GAG GGC AAG GAG GGT CAT CCG GAC AGC AAT ACA GTC ACG CTG    6462
```

```
Glu Gln Glu Gly Lys Glu Gly His Pro Asp Ser Asn Thr Val Thr Leu
            2090            2095                2100

CAG GCC GGC TTG CGA ACC TTA CAC GAA GTG TCC CCA GCT CTA AAG AGA        6510
Gln Ala Gly Leu Arg Thr Leu His Glu Val Ser Pro Ala Leu Lys Arg
        2105            2110                2115

GCC ATC TCC GGC AAT CTC GAC GAG CTG GAC CAG GAG CCG GAG CCC ATG        6558
Ala Ile Ser Gly Asn Leu Asp Glu Leu Asp Gln Glu Pro Glu Pro Met
            2120            2125                2130

CAT CGT CGT CAT CAT ACG CTT TTC GGC AGC GTG TGG TCA TCG ATC CGC        6606
His Arg Arg His His Thr Leu Phe Gly Ser Val Trp Ser Ser Ile Arg
2135            2140            2145                2150

CGA CAT GGA AAC GGA ACC TTC AGG CGA AGT GCC AAG GCA ACT GCT TCG        6654
Arg His Gly Asn Gly Thr Phe Arg Arg Ser Ala Lys Ala Thr Ala Ser
                2155            2160                2165

CAG AGC AAC GGA GCC TTG GCG ATC GGT GGA TCC GCG TCC GCG GCC TTG        6702
Gln Ser Asn Gly Ala Leu Ala Ile Gly Gly Ser Ala Ser Ala Ala Leu
            2170            2175                2180

GGT GTG GGC GGT AGC TCG CTG GTC CTG GGA AGC AGC GAT CCC GCT GGC        6750
Gly Val Gly Gly Ser Ser Leu Val Leu Gly Ser Ser Asp Pro Ala Gly
            2185            2190                2195

GGG GAT TAT CTG TAC GAC ACT CTG AAC CGC AGC GTA GCC GAC GGA GTG        6798
Gly Asp Tyr Leu Tyr Asp Thr Leu Asn Arg Ser Val Ala Asp Gly Val
        2200            2205                2210

AAC AAT ATA ACG CGG AAC ATA ATG CAG GCC CGT TTG GCG GCA GCC GGA        6846
Asn Asn Ile Thr Arg Asn Ile Met Gln Ala Arg Leu Ala Ala Ala Gly
2215            2220            2225                2230

AAG CTG CAG GAC GAA CTG CAG GGG GCA GGA AGT GGC GGA GAG CTA AGG        6894
Lys Leu Gln Asp Glu Leu Gln Gly Ala Gly Ser Gly Gly Glu Leu Arg
            2235            2240                2245

ACA TTC GGC GAG AGC ATA TCC ATG CGA CCG CTG GCC AAA AAT GGA GGC        6942
Thr Phe Gly Glu Ser Ile Ser Met Arg Pro Leu Ala Lys Asn Gly Gly
            2250            2255                2260

GGA GCG GCC ACT GTG GCC GGA ACA CTG CCG CCT GAG GCG AAT GCC ATT        6990
Gly Ala Ala Thr Val Ala Gly Thr Leu Pro Pro Glu Ala Asn Ala Ile
            2265            2270                2275

AAC TAT GAC AAC CGC AAT CGT GGT ATT TTA TTG CAT CCA TAT AAC AAT        7038
Asn Tyr Asp Asn Arg Asn Arg Gly Ile Leu Leu His Pro Tyr Asn Asn
        2280            2285                2290

GTC TAC GCA CCC AAT GGT GCT CTT CCT GGC CAC GAA CGC ATG ATC CAA        7086
Val Tyr Ala Pro Asn Gly Ala Leu Pro Gly His Glu Arg Met Ile Gln
2295            2300            2305                2310

TCG ACA CCA GCT AGT CCC TAC GAT CAG CGT CGT TTA CCA ACT TCA TCT        7134
Ser Thr Pro Ala Ser Pro Tyr Asp Gln Arg Arg Leu Pro Thr Ser Ser
            2315            2320                2325

GAT ATG AAC GGT CTA GCC GAA TCA TTG ATT GGA GGG GTA CTC GCC GCT        7182
Asp Met Asn Gly Leu Ala Glu Ser Leu Ile Gly Gly Val Leu Ala Ala
            2330            2335                2340

GAA GGG ATG GGT AAA TAC TGC GAC TCC GAG TTC GTG GGG ACT GCT GCA        7230
Glu Gly Met Gly Lys Tyr Cys Asp Ser Glu Phe Val Gly Thr Ala Ala
            2345            2350                2355

CGG GAG ATG CGC GAA GCG CTG GAC ATG ACG CCC GAG GAA ATG AAC CTG        7278
Arg Glu Met Arg Glu Ala Leu Asp Met Thr Pro Glu Glu Met Asn Leu
            2360            2365                2370

GCC GCC CAC CAG ATC CTC TCC AAC GAG CAC TCG CTG AGT CTG ATC GGC        7326
Ala Ala His Gln Ile Leu Ser Asn Glu His Ser Leu Ser Leu Ile Gly
2375            2380            2385                2390

AGT AGC AAT GGT AGC ATC TTC GGT GGA TCC GCC GGT GGC CTG GGA GGG        7374
Ser Ser Asn Gly Ser Ile Phe Gly Gly Ser Ala Gly Gly Leu Gly Gly
            2395            2400                2405
```

```
GCT GGA TCT GGA GGT GTG GGT GGA TTG GGC GGT AGT AGC AGC ATT CGC      7422
Ala Gly Ser Gly Gly Val Gly Gly Leu Gly Gly Ser Ser Ser Ile Arg
            2410                2415                2420

AAC GCT TTC GGC GGA AGC GGA AGT GGA CCG TCC TCG CTG TCG CCG CAA      7470
Asn Ala Phe Gly Gly Ser Gly Ser Gly Pro Ser Ser Leu Ser Pro Gln
        2425                2430                2435

CAT CAG CCT TAC TCG GGC ACT CTG AAC TCA CCA CCG ATT CCG GAT AAT      7518
His Gln Pro Tyr Ser Gly Thr Leu Asn Ser Pro Pro Ile Pro Asp Asn
    2440                2445                2450

CGT CTG AGA CGT GTT GCC ACA GTC ACG ACC ACA AAC AAT AAC AAT AAG      7566
Arg Leu Arg Arg Val Ala Thr Val Thr Thr Thr Asn Asn Asn Asn Lys
2455                2460                2465                2470

TCC CAA GTT AGC CAA AAC AAT TCG AGT AGC TTA AAT GTT AGG GCT AAT      7614
Ser Gln Val Ser Gln Asn Asn Ser Ser Ser Leu Asn Val Arg Ala Asn
            2475                2480                2485

GCC AAT AGC CAA ATG AAC ATG TCA CCA ACT GGA CAA CCA GTG CAG CAA      7662
Ala Asn Ser Gln Met Asn Met Ser Pro Thr Gly Gln Pro Val Gln Gln
        2490                2495                2500

CAA TCG CCG CTA AGA GGA CAG GGC AAT CAG ACT TAC TCC TCA              7704
Gln Ser Pro Leu Arg Gly Gln Gly Asn Gln Thr Tyr Ser Ser
    2505                2510                2515

TAGCACCCAC ATTGTAAGCT ATACATACAG AATGTCTTCT TGATGGAACT TTAAATGTGC    7764

ATTCAGCGCA AGCTGAGGTT TATTGGCTAA TTTATTTGTT ATTTTTAGCG AAGAAAAACA    7824

CATTAGTCTT AGCATCGGGA ATTGTTATAT TTGAATTGTT CGCACACACA CAAGCGGGAA    7884

CCAAACCAAC AAAACTTGTA TAACTTGTAT AAAGAAAATC AGCTAATTGT ATATGTATAA    7944

ATATATTAAT GTTTTTGCCT TTTTGAGAAA TCTATCGTGG GCCTTCGTCC TCTAACGAGC    8004

CAGAAAACCA AAAACCAAC AACACTAAAC TGAACAAATT AAGGAAAAAT GTATATTTTT    8064

GGATAAAAAA A                                                         8075

(2) INFORMATION FOR SEQ ID NO:2:

(i) SEQUENCE CHARACTERISTICS:
        (A) LENGTH: 2516 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Gly Gly Glu Leu Val Asn Cys Ile Ala Tyr Asp Asp Asn Thr
1               5                   10                  15

Leu Val Ile Glu Arg Lys Pro Ser Pro Ser Pro Ser Thr Ser Arg
            20                  25                  30

Arg Tyr Leu Lys Ala Glu Thr Pro Thr Arg Gly Ser Arg Lys Tyr Asn
        35                  40                  45

Arg Lys Ser Ser Ala Lys Ser Asp Leu Glu Val Val Val Lys Pro
    50                  55                  60

Glu His His Gln His Arg Ser Pro Thr Ile Thr Leu Pro Val Pro
65              70                  75                  80

Ala Asn Pro Leu Thr Thr Ser Ala Ser Ala Gly Ser Ser Pro Thr Gly
            85                  90                  95

Ala Gly Leu Ala Ala Gly Leu Gly Thr Ala Ser Gly Thr Val Leu Gln
        100                 105                 110

Gln Ser Cys Ser Ala Leu Asp Pro Pro Glu Asp Ser Asn Gln Pro Ser
    115                 120                 125

Gly Thr Arg Arg Arg Ala Thr Ser Thr Glu Leu Ala Leu Ser Asn Val
```

-continued

```
            130                 135                 140
Thr Ser Gln Ile Val Asn Asn Ala Thr Tyr Lys Leu Asp Phe Lys Gln
145                 150                 155                 160
Arg Arg His Lys Ser Asn Asn Gly Gly Ser Glu Ser Gly Ser Leu Thr
                165                 170                 175
Gly Ile Ala Thr Gly Pro Ala Thr Ser Pro Ala Gly Pro Thr Gly Pro
                180                 185                 190
Thr Ser Ser Ser Gly Lys Arg Arg Lys Ser Ser Cys Thr Ser Cys Gly
                195                 200                 205
Gly Gly Gly Ile Ser Ala Pro Pro Arg Leu Thr Pro Glu Glu Ala
210                 215                 220
Trp Gln Leu Gln Pro Gln Asn Ser Val Thr Ser Ala Gly Ser Thr Asn
225                 230                 235                 240
Ser Ser Phe Ser Ser Gly Gly Arg Asp Asp Asn Ser Ser Tyr Ser
                245                 250                 255
Ala Val Gly Gly Asp Ser Ser Ser Asn Ser Cys Asn Cys Asp Ile
                260                 265                 270
Thr Gly Asp Asn Ser Thr Leu His Gly Leu Gly Val Gly Asp Val Cys
                275                 280                 285
Ser Phe Ile Ala Asp Cys Asp Asp Asn Ser Glu Asp Asp Asp Gly Asp
290                 295                 300
Pro Asn Asn Gln Asp Leu Ser Ser Gln Thr Leu Arg Thr Ala Ala Ile
305                 310                 315                 320
Val Ala Ala Val Ala Ala Ala Lys Glu Gln Ala Gln Glu Gln Ser
                325                 330                 335
Leu Ala Asp Cys Glu Ser Phe Ser Asp Arg Arg Gln Asp Ala Asp Glu
                340                 345                 350
Asp Val Arg Ile Ile Gln Asp Cys Cys Gly Gly Asn Asn Asp Ser Leu
                355                 360                 365
Glu Asp Val Gly Glu Val Asp Asp Asn Ala Asp Val Val Arg Lys
370                 375                 380
Asn Ser Arg Asn Arg Pro Ser Ile Arg Arg Thr Cys Arg Ile Thr Glu
385                 390                 395                 400
Glu Asp Asp Asp Glu Asp Glu Asn Ala Asp Tyr Gly Asp Phe Asp Arg
                405                 410                 415
Glu Asp Gln Glu Leu Asp Asp Glu Pro Glu Gly Thr Thr Ile Asp
                420                 425                 430
Ile Asp Glu Gln Glu Gln Gln His Asp Gln Gly Asp Ser Ala Glu Glu
                435                 440                 445
Glu Asp His Asp Glu Asp Val Asp Glu Tyr Phe Glu Glu Glu Asp
                450                 455                 460
Asp Thr Gln Ala Phe Ser Pro Phe Tyr Ser Ser Ser Ala Glu Leu Ile
465                 470                 475                 480
Asp Asn Phe Gly Gly Gly Ala Gly Lys Phe Phe Asn Ile Met Asp Phe
                485                 490                 495
Glu Arg Gly Ala Ser Gly Glu Gly Phe Ser Pro Asn Gly Asn Gly
                500                 505                 510
Gly Pro Gly Ser Gly Asp Val Ser Arg Thr Ala Arg Tyr Asp Ser Gly
                515                 520                 525
Glu Gly Asp Leu Gly Gly Gly Asn Asn Ile Met Gly Ile Asp Ser Met
                530                 535                 540
Gly Ile Ala Asn Ile Pro Glu Thr Met Asn Gly Thr Thr Ile Gly Pro
545                 550                 555                 560
```

```
Ser Gly Ala Gly Gly Gln Lys Gly Gly Ala Ala Gly Ala Ala Gly
                565                 570                 575
Gln Lys Arg Gln Gln Arg Arg Gly Lys Pro Gln Pro Asp Arg Pro Gln
            580                 585                 590
Arg Ala Leu Phe Cys Leu Ser Val Lys Asn Pro Leu Arg Ala Leu Cys
            595                 600                 605
Ile Arg Ile Val Glu Trp Lys Pro Phe Glu Phe Leu Ile Leu Leu Thr
            610                 615                 620
Ile Phe Ala Asn Cys Ile Ala Leu Ala Val Tyr Thr Pro Tyr Pro Gly
625                 630                 635                 640
Ser Asp Ser Asn Val Thr Asn Gln Thr Leu Glu Lys Val Glu Tyr Val
                645                 650                 655
Phe Leu Val Ile Phe Thr Ala Glu Cys Val Met Lys Ile Leu Ala Tyr
                660                 665                 670
Gly Phe Val Leu His Asp Gly Ala Tyr Leu Gly Asn Gly Trp Asn Leu
                675                 680                 685
Leu Asp Phe Thr Ile Val Val Met Gly Ala Ile Ser Thr Ala Leu Ser
            690                 695                 700
Gln Leu Met Lys Asp Ala Phe Asp Val Lys Ala Leu Arg Ala Phe Arg
705                 710                 715                 720
Val Leu Arg Pro Leu Arg Leu Val Ser Gly Val Pro Ser Leu Gln Val
                725                 730                 735
Val Leu Asn Ser Ile Leu Lys Ala Met Val Pro Leu Phe His Ile Ala
                740                 745                 750
Leu Leu Val Leu Phe Val Ile Ile Tyr Ala Ile Ile Gly Leu Glu
                755                 760                 765
Leu Phe Ser Gly Lys Leu His Lys Ala Cys Arg Asp Glu Ile Thr Gly
            770                 775                 780
Glu Tyr Glu Glu Asn Ile Arg Pro Cys Gly Val Gly Tyr Gln Cys Pro
785                 790                 795                 800
Pro Gly Tyr Lys Cys Tyr Gly Gly Trp Asp Gly Pro Asn Asp Gly Ile
                805                 810                 815
Thr Asn Phe Asp Asn Phe Gly Leu Ala Met Leu Thr Val Phe Gln Cys
            820                 825                 830
Val Thr Leu Glu Gly Trp Thr Asp Val Leu Tyr Ser Ile Gln Asp Ala
            835                 840                 845
Met Gly Ser Asp Trp Gln Trp Met Tyr Phe Ile Ser Met Val Ile Leu
            850                 855                 860
Gly Ala Phe Phe Val Met Asn Leu Ile Leu Gly Val Leu Ser Gly Glu
865                 870                 875                 880
Phe Ser Lys Glu Arg Asn Lys Ala Lys Asn Arg Gly Asp Phe Gln Lys
                885                 890                 895
Leu Arg Glu Lys Gln Gln Ile Glu Glu Asp Leu Arg Gly Tyr Leu Asp
                900                 905                 910
Trp Ile Thr Gln Ala Glu Asp Ile Glu Pro Asp Ala Val Gly Gly Leu
            915                 920                 925
Ile Ser Asp Gly Lys Gly Lys Gln Pro Asn Glu Met Asp Ser Thr Glu
            930                 935                 940
Asn Leu Gly Glu Glu Met Pro Glu Val Gln Met Thr Glu Ser Arg Trp
945                 950                 955                 960
Arg Lys Met Lys Lys Asp Phe Asp Arg Val Asn Arg Arg Met Arg Arg
                965                 970                 975
```

-continued

```
Ala Cys Arg Lys Ala Val Lys Ser Gln Ala Phe Tyr Trp Leu Ile Ile
            980                 985                 990

Val Leu Val Phe Leu Asn Thr Gly Val Leu Ala Thr Glu His Tyr Gly
            995                1000                1005

Gln Leu Asp Trp Leu Asp Asn Phe Gln Glu Tyr Thr Asn Val Phe Phe
           1010                1015                1020

Ile Gly Leu Phe Thr Cys Glu Met Leu Leu Lys Met Tyr Ser Leu Gly
1025                1030                1035                1040

Phe Gln Gly Tyr Phe Val Ser Leu Phe Asn Arg Phe Asp Cys Phe Val
                1045                1050                1055

Val Ile Gly Ser Ile Thr Glu Thr Leu Leu Thr Asn Thr Gly Met Met
            1060                1065                1070

Pro Pro Leu Gly Val Ser Val Leu Arg Cys Val Arg Leu Leu Arg Val
            1075                1080                1085

Phe Lys Val Thr Lys Tyr Trp Arg Ser Leu Ser Asn Leu Val Ala Ser
            1090                1095                1100

Leu Leu Asn Ser Ile Gln Ser Ile Ala Ser Leu Leu Leu Leu Leu Phe
1105                1110                1115                1120

Leu Phe Ile Val Ile Phe Ala Leu Leu Gly Met Gln Val Phe Gly Gly
                1125                1130                1135

Lys Phe Asn Phe Asp Gly Lys Glu Glu Lys Tyr Arg Met Asn Phe Asp
            1140                1145                1150

Cys Phe Trp Gln Ala Leu Leu Thr Val Phe Gln Ile Met Thr Gly Glu
            1155                1160                1165

Asp Trp Asn Ala Val Met Tyr Val Gly Ile Asn Ala Tyr Gly Gly Val
            1170                1175                1180

Ser Ser Tyr Gly Ala Leu Ala Cys Ile Tyr Phe Ile Ile Leu Phe Ile
1185                1190                1195                1200

Cys Gly Asn Tyr Ile Leu Leu Asn Val Phe Leu Ala Ile Ala Val Asp
                1205                1210                1215

Asn Leu Ala Asp Ala Asp Ser Leu Ser Glu Val Glu Lys Glu Glu Glu
            1220                1225                1230

Pro His Asp Glu Ser Ala Gln Lys Lys Ser His Ser Pro Thr Pro Thr
            1235                1240                1245

Ile Asp Gly Met Asp Asp His Leu Ser Ile Asp Ile Asp Met Glu Gln
            1250                1255                1260

Gln Glu Leu Asp Asp Glu Asp Lys Met Asp His Glu Thr Leu Ser Asp
1265                1270                1275                1280

Glu Glu Val Arg Glu Met Cys Glu Glu Glu Glu Val Asp Glu Glu
                1285                1290                1295

Gly Met Ile Thr Ala Arg Pro Arg Arg Met Ser Glu Val Asn Thr Ala
            1300                1305                1310

Thr Lys Ile Leu Pro Ile Pro Pro Gly Thr Ser Phe Phe Leu Phe Ser
            1315                1320                1325

Gln Thr Asn Arg Phe Arg Val Phe Cys His Trp Leu Cys Asn His Ser
            1330                1335                1340

Asn Phe Gly Asn Ile Ile Leu Cys Cys Ile Met Phe Ser Ser Ala Met
1345                1350                1355                1360

Leu Ala Ala Glu Asn Pro Leu Arg Ala Asn Asp Asp Leu Asn Lys Val
                1365                1370                1375

Leu Asn Lys Phe Asp Tyr Phe Phe Thr Ala Val Phe Thr Met Glu Leu
            1380                1385                1390

Ile Leu Lys Leu Ile Ser Tyr Gly Phe Val Leu His Asp Gly Ala Phe
```

-continued

```
            1395                1400                1405

Cys Arg Ser Ala Phe Asn Leu Leu Asp Leu Leu Val Val Cys Val Ser
    1410                1415                1420

Leu Ile Ser Leu Val Ser Ser Asp Ala Ile Ser Val Val Lys Ile
1425                1430                1435                1440

Leu Arg Val Leu Arg Val Leu Arg Pro Leu Arg Ala Ile Asn Arg Ala
            1445                1450                1455

Lys Gly Leu Lys His Val Val Gln Cys Val Ile Val Ala Val Lys Thr
        1460                1465                1470

Ile Gly Asn Ile Val Leu Val Thr Cys Leu Leu Gln Phe Met Phe Ala
    1475                1480                1485

Val Ile Gly Val Gln Leu Phe Lys Gly Lys Phe Lys Cys Thr Asp
    1490                1495                1500

Gly Ser Lys Met Thr Gln Asp Glu Cys Tyr Gly Thr Tyr Leu Val Tyr
1505                1510                1515                1520

Asp Asp Gly Asp Val His Lys Pro Arg Leu Arg Glu Arg Glu Trp Ser
            1525                1530                1535

Asn Asn Arg Phe His Phe Asp Asp Val Ala Lys Gly Met Leu Thr Leu
            1540                1545                1550

Phe Thr Val Ser Thr Phe Glu Gly Trp Pro Gly Leu Leu Tyr Val Ser
            1555                1560                1565

Ile Asp Ser Asn Lys Glu Asn Gly Gly Pro Ile His Asn Phe Arg Pro
    1570                1575                1580

Ile Val Ala Ala Tyr Tyr Ile Ile Tyr Ile Ile Ile Ala Phe Phe
1585                1590                1595                1600

Met Val Asn Ile Phe Val Gly Phe Val Ile Val Thr Phe Gln Asn Glu
            1605                1610                1615

Gly Glu Gln Glu Tyr Lys Asn Cys Asp Leu Asp Lys Asn Gln Arg Asn
            1620                1625                1630

Cys Ile Glu Phe Ala Leu Lys Ala Lys Pro Val Arg Arg Tyr Ile Pro
            1635                1640                1645

Lys His Gly Ile Gln Tyr Lys Val Trp Trp Phe Val Thr Ser Ser Ser
    1650                1655                1660

Phe Glu Tyr Thr Ile Phe Ile Leu Ile Met Ile Asn Thr Val Thr Leu
1665                1670                1675                1680

Ala Met Lys Phe Tyr Asn Gln Pro Leu Trp Tyr Thr Glu Leu Leu Asp
            1685                1690                1695

Ala Leu Asn Met Ile Phe Thr Ala Val Phe Ala Leu Glu Phe Val Phe
        1700                1705                1710

Lys Leu Ala Ala Phe Arg Phe Lys Asn Tyr Phe Gly Asp Ala Trp Asn
    1715                1720                1725

Val Phe Asp Phe Ile Ile Val Leu Gly Ser Phe Ile Asp Ile Val Tyr
    1730                1735                1740

Ser Glu Ile Lys Ser Lys Asp Thr Ser Gln Ile Ala Glu Cys Asp Ile
1745                1750                1755                1760

Val Glu Gly Cys Lys Ser Thr Lys Lys Ser Ala Gly Ser Asn Leu Ile
            1765                1770                1775

Ser Ile Asn Phe Phe Arg Leu Phe Arg Val Met Arg Leu Val Lys Leu
            1780                1785                1790

Leu Ser Lys Gly Glu Gly Ile Arg Thr Leu Leu Trp Thr Phe Ile Lys
        1795                1800                1805

Ser Phe Gln Ala Leu Pro Tyr Val Ala Leu Leu Ile Val Leu Leu Phe
    1810                1815                1820
```

-continued

Phe Ile Tyr Ala Val Val Gly Met Gln Val Phe Gly Lys Ile Ala Leu
1825                1830                1835                1840

Asp Gly Gly Asn Ala Ile Thr Ala Asn Asn Phe Gln Thr Phe Gln
            1845                1850                1855

Gln Ala Val Leu Val Leu Phe Arg Ser Ala Thr Gly Glu Ala Trp Gln
                1860                1865                1870

Glu Ile Met Met Ser Cys Ser Ala Gln Pro Asp Val Lys Cys Asp Met
        1875                1880                1885

Asn Ser Asp Thr Pro Gly Glu Pro Cys Gly Ser Ser Ile Ala Tyr Pro
            1890                1895                1900

Tyr Phe Ile Ser Phe Tyr Val Leu Cys Ser Phe Leu Ile Ile Asn Leu
1905                1910                1915                1920

Phe Val Ala Val Ile Met Asp Asn Phe Asp Tyr Leu Thr Arg Asp Trp
                1925                1930                1935

Ser Ile Leu Gly Pro His His Leu Asp Glu Phe Ile Arg Leu Trp Ser
            1940                1945                1950

Glu Tyr Asp Pro Asp Ala Lys Gly Arg Ile Lys His Leu Asp Val Val
    1955                1960                1965

Thr Leu Leu Arg Lys Ile Ser Pro Pro Leu Gly Phe Gly Lys Leu Cys
1970                1975                1980

Pro His Arg Met Ala Cys Lys Arg Leu Val Ser Met Asn Met Pro Leu
1985                1990                1995                2000

Asn Ser Asp Gly Thr Val Leu Phe Asn Ala Thr Leu Phe Ala Val Val
            2005                2010                2015

Arg Thr Ser Leu Ser Ile Lys Thr Asp Gly Asn Ile Asp Ala Asn
            2020                2025                2030

Ser Glu Leu Arg Ala Thr Ile Lys Gln Ile Trp Lys Arg Thr Asn Pro
            2035                2040                2045

Lys Leu Leu Asp Gln Val Val Pro Pro Gly Asn Asp Asp Glu Val
            2050                2055                2060

Thr Val Gly Lys Phe Tyr Ala Thr Tyr Leu Ile Gln Asp Tyr Phe Arg
2065                2070                2075                2080

Arg Phe Lys Lys Arg Lys Glu Gln Glu Gly Lys Glu Gly His Pro Asp
                2085                2090                2095

Ser Asn Thr Val Thr Leu Gln Ala Gly Leu Arg Thr Leu His Glu Val
            2100                2105                2110

Ser Pro Ala Leu Lys Arg Ala Ile Ser Gly Asn Leu Asp Glu Leu Asp
            2115                2120                2125

Gln Glu Pro Glu Pro Met His Arg Arg His Thr Leu Phe Gly Ser
            2130                2135                2140

Val Trp Ser Ser Ile Arg Arg His Gly Asn Gly Thr Phe Arg Arg Ser
2145                2150                2155                2160

Ala Lys Ala Thr Ala Ser Gln Ser Asn Gly Ala Leu Ala Ile Gly Gly
                2165                2170                2175

Ser Ala Ser Ala Ala Leu Gly Val Gly Gly Ser Ser Leu Val Leu Gly
            2180                2185                2190

Ser Ser Asp Pro Ala Gly Gly Asp Tyr Leu Tyr Asp Thr Leu Asn Arg
            2195                2200                2205

Ser Val Ala Asp Gly Val Asn Asn Ile Thr Arg Asn Ile Met Gln Ala
    2210                2215                2220

Arg Leu Ala Ala Ala Gly Lys Leu Gln Asp Glu Leu Gln Gly Ala Gly
2225                2230                2235                2240

-continued

```
Ser Gly Gly Glu Leu Arg Thr Phe Gly Glu Ser Ile Ser Met Arg Pro
            2245                2250                2255

Leu Ala Lys Asn Gly Gly Ala Ala Thr Val Ala Gly Thr Leu Pro
        2260                2265                2270

Pro Glu Ala Asn Ala Ile Asn Tyr Asp Asn Arg Asn Arg Gly Ile Leu
        2275                2280                2285

Leu His Pro Tyr Asn Asn Val Tyr Ala Pro Asn Gly Ala Leu Pro Gly
        2290                2295                2300

His Glu Arg Met Ile Gln Ser Thr Pro Ala Ser Pro Tyr Asp Gln Arg
2305                2310                2315                2320

Arg Leu Pro Thr Ser Ser Asp Met Asn Gly Leu Ala Glu Ser Leu Ile
            2325                2330                2335

Gly Gly Val Leu Ala Ala Glu Gly Met Gly Lys Tyr Cys Asp Ser Glu
            2340                2345                2350

Phe Val Gly Thr Ala Ala Arg Glu Met Arg Glu Ala Leu Asp Met Thr
            2355                2360                2365

Pro Glu Glu Met Asn Leu Ala Ala His Gln Ile Leu Ser Asn Glu His
        2370                2375                2380

Ser Leu Ser Leu Ile Gly Ser Ser Asn Gly Ser Ile Phe Gly Gly Ser
2385                2390                2395                2400

Ala Gly Gly Leu Gly Gly Ala Gly Ser Gly Gly Val Gly Gly Leu Gly
            2405                2410                2415

Gly Ser Ser Ser Ile Arg Asn Ala Phe Gly Gly Ser Gly Ser Gly Pro
            2420                2425                2430

Ser Ser Leu Ser Pro Gln His Gln Pro Tyr Ser Gly Thr Leu Asn Ser
            2435                2440                2445

Pro Pro Ile Pro Asp Asn Arg Leu Arg Arg Val Ala Thr Val Thr Thr
        2450                2455                2460

Thr Asn Asn Asn Lys Ser Gln Val Ser Gln Asn Asn Ser Ser Ser
2465                2470                2475                2480

Leu Asn Val Arg Ala Asn Ala Asn Ser Gln Met Asn Met Ser Pro Thr
            2485                2490                2495

Gly Gln Pro Val Gln Gln Gln Ser Pro Leu Arg Gly Gln Gly Asn Gln
            2500                2505                2510

Thr Tyr Ser Ser
        2515
```

(2) INFORMATION FOR SEQ ID NO:3:

(i) SEQUENCE CHARACTERISTICS:
        (A) LENGTH: 785 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Ser Glu Val Asn Thr Ala Thr Lys Ile Leu Pro Ile Pro Gly
1               5                   10                  15

Thr Ser Phe Phe Leu Phe Ser Gln Thr Asn Arg Phe Arg Val Phe Cys
            20                  25                  30

His Trp Leu Cys Asn His Ser Asn Glu Gly Asn Met Val Gly Gly Gly
            35                  40                  45

Ile Met Glu Ser Ser Ala Met Glu Ala Ala Glu Asn Pro Leu Arg Ala
        50                  55                  60
```

-continued

```
Asn Asp Asp Leu Asn Lys Val Leu Asn Lys Glu Asp Tyr Phe Glu Thr
 65              70              75              80

Ala Val Phe Asp Pro Glu Leu Ile Leu Lys Asp Ile Ser Tyr Gly Phe
             85              90              95

Val Leu His Asp Gly Ala Phe Cys Arg Ser Ala Arg Asn Glu Leu Asp
            100             105             110

Leu Leu Val Val Cys Val Ser Ile Leu Ser Leu Val Ser Ser Ser Asn
            115             120             125

Ala Ile Ser Val Val Lys Ile Leu Arg Val Leu Arg Val Leu Arg Pro
130             135             140

Asx Arg Ala Ile Asn Arg Ala Lys Gly Leu Lys His Val Val Gln Cys
145             150             155             160

Ile Val Ala Val Thr Lys Thr Ile Gly Asn Ile Val Leu Val Ile Gly
            165             170             175

Leu Leu Gln Phe Met Glu Ala Val Ile Gly Val Leu Phe Lys Gly Lys
            180             185             190

Phe Phe Lys Cys Thr Asp Gly Ser Lys Met Thr Gln Asp Glu Cys Tyr
            195             200             205

Gly Thr Tyr Leu Val Tyr Asp Asp Gly Asp Val His Lys Pro Arg Leu
            210             215             220

Arg Glu Arg Glu Trp Ser Asn Asn Arg Phe His Phe Asp Asp Val Ala
225             230             235             240

Lys Gly Met Leu Thr Leu Phe Thr Val Ser Thr Phe Glu Gly Trp Pro
            245             250             255

Gly Leu Leu Tyr Val Ser Ile Asp Ser Asn Lys Glu Asn Gly Gly Pro
            260             265             270

Ile His Asn Phe Arg Pro Ile Val Ala Ala Tyr Tyr Asp Ile Tyr Ile
            275             280             285

Ile Ile Tyr Ala Phe Phe Met Val Asn Ile Glu Val Gly Arg Val Ile
            290             295             300

Val Thr Phe Gln Asn Glu Gly Glu Gln Glu Tyr Lys Asn Cys Asp Leu
305             310             315             320

Asp Lys Asn Gln Arg Asn Cys Ile Glu Phe Ala Leu Lys Ala Lys Pro
            325             330             335

Val Arg Arg Tyr Ile Pro Lys His Gly Ile Gln Tyr Lys Val Trp Trp
            340             345             350

Phe Val Thr Ser Ser Ser Glu Glu Tyr Thr Ile Glu Ile Leu Ile Met
            355             360             365

Ile Asn Thr Val Thr Leu Ala Met Lys Phe Tyr Asn Gln Pro Leu Trp
            370             375             380

Tyr Thr Glu Leu Leu Asp Ala Leu Asn Met Ile Glu Ile Ala Val Glu
385             390             395             400

Ala Leu Glu Glu Val Glu Lys Leu Ala Ala Phe Arg Phe Lys Asn Tyr
            405             410             415

Phe Gly Asp Ala Trp Asn Val Glu Asp Glu Ile Leu Val Leu Gly Ser
            420             425             430

Phe Ile Asp Leu Val Tyr Ser Glu Ile Lys Ser Lys Asp Thr Ser Gln
            435             440             445

Ile Ala Glu Cys Asp Ile Val Glu Gly Cys Lys Ser Thr Lys Lys Ser
            450             455             460

Ala Gly Ser Asn Leu Ile Ser Ile Asn Phe Phe Arg Leu Glu Arg Val
465             470             475             480

Met Arg Leu Val Lys Leu Leu Ser Lys Gly Glu Gly Ile Arg Thr Leu
```

-continued

```
                       485                 490                 495
Leu Trp Thr Phe Ile Lys Ser Phe Gln Ala Leu Pro Tyr Val Ala Leu
                500                 505                 510
Leu Ile Val Leu Glu Glu Ile Tyr Ala Val Val Gly Met Val Glu
            515                 520                 525
Gly Lys Ile Ala Leu Asp Gly Gly Asn Ala Ile Thr Ala Asn Asn Asn
        530                 535                 540
Phe Gln Thr Phe Gln Gln Ala Val Leu Val Leu Phe Arg Ser Ala Thr
545                 550                 555                 560
Gly Glu Ala Trp Gln Glu Ile Met Met Ser Cys Ser Ala Gln Pro Asp
                565                 570                 575
Val Lys Cys Asp Met Asn Ser Asp Thr Pro Gly Glu Pro Cys Gly Ser
                580                 585                 590
Ser Ile Ala Tyr Arg Tyr Glu Ile Ser Glu Tyr Val Leu Cys Ser Phe
                595                 600                 605
Leu Leu Ile Asn Leu Glu Val Ala Val Ile Met Asp Asn Phe Asp Tyr
            610                 615                 620
Leu Thr Arg Asp Trp Ser Ile Leu Gly Pro His His Leu Asp Glu Phe
625                 630                 635                 640
Ile Arg Leu Trp Ser Glu Tyr Asp Pro Asp Ala Lys Gly Arg Ile Lys
                    645                 650                 655
His Leu Asp Val Val Thr Leu Leu Arg Lys Ile Ser Pro Pro Leu Gly
                660                 665                 670
Phe Gly Lys Leu Cys Pro His Arg Met Ala Cys Lys Arg Leu Val Ser
                675                 680                 685
Met Asn Met Pro Leu Asn Ser Asp Gly Thr Val Leu Phe Asn Ala Thr
690                 695                 700
Leu Phe Ala Val Val Arg Thr Ser Leu Ser Ile Lys Thr Asp Gly Asn
705                 710                 715                 720
Ile Asp Asp Ala Asn Ser Glu Leu Arg Ala Thr Ile Lys Gln Ile Trp
                    725                 730                 735
Lys Arg Thr Asn Pro Lys Leu Leu Asp Gln Val Val Pro Pro Pro Gly
                740                 745                 750
Asn Asp Asp Glu Val Thr Val Gly Lys Phe Tyr Ala Thr Tyr Leu Ile
                755                 760                 765
Gln Asp Tyr Phe Arg Arg Phe Lys Lys Arg Lys Glu Gln Glu Gly Lys
770                 775                 780
Glu
785

(2) INFORMATION FOR SEQ ID NO:4:

(i) SEQUENCE CHARACTERISTICS:
        (A) LENGTH: 793 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Glu Ile Pro Val Ser Pro Arg Pro Arg Pro Leu Ala Glu Leu Gln Leu
1               5                   10                  15
Lys Glu Lys Ala Val Pro Ile Pro Glu Ala Ser Ser Phe Phe Ile Phe
                20                  25                  30
Ser Pro Thr Asn Lys Val Arg Val Leu Cys His Arg Ile Val Asn Ala
```

-continued

```
                35                  40                  45
Thr Trp Glu Ile Asn Glu Ile Leu Leu Phe Ile Leu Leu Ser Ser Ala
            50                  55                  60
Ala Asp Ala Ala Glu Asp Pro Ile Arg Ala Ser Val Arg Asn Gln
 65                  70                  75                  80
Ile Leu Gly Tyr Glu Asp Ile Ala Phe Ile Ser Val Glu Thr Val Glu
                85                  90                  95
Leu Val Leu Arg Met Ile Ser Tyr Gly Ala Phe Leu His Lys Gly Phe
                100                 105                 110
Ser Cys Arg Asn Leu Lys Asn Asn Ile Asp Ala Leu Leu Val Val Ala
            115                 120                 125
Val Gly Ile Arg Lys Met Ile Glu Ser Ser Thr Ile Ser Val Val Lys
        130                 135                 140
Ile Ile Arg Met Leu Arg Val Met Leu Arg His His Arg Ala Val Asn
145                 150                 155                 160
Arg Ala Lys Gly Leu Lys His Val Val Gln Cys Phe Val Ala Ile Arg
                165                 170                 175
Thr Ile Gly Asn Ile Val Ile Val Thr Leu Leu Gln Glu Met Glu
                180                 185                 190
Ala Gln Ile Gln Val Gln Leu Glu Lys Gly Lys Phe Phe Ser Cys Asn
            195                 200                 205
Asp Leu Ser Lys Met Thr Glu Glu Cys Arg Gly Tyr Tyr Tyr Val
        210                 215                 220
Tyr Lys Asp Gly Asp Pro Thr Gln Met Glu Leu Arg Pro Arg Trp Ile
225                 230                 235                 240
His Asn Asp Phe His Phe Asp Asn Val Leu Ser Ala Met Met Ser Leu
                245                 250                 255
Phe Thr Val Ser Thr Phe Glu Gly Trp Pro Gln Leu Leu Tyr Arg Ala
                260                 265                 270
Ile Asp Ser Asn Glu Glu Asp Met Gly Pro Val Tyr Asn Asn Arg Val
            275                 280                 285
Glu Met Ala Ile Phe Phe Ile Tyr Ile Ile Leu Ile Ala Lys Glu
        290                 295                 300
Met Met Asn Gln Phe Val Gly Ile Ala Ala Val Thr Phe Gln Glu Gln
305                 310                 315                 320
Gly Glu Thr Glu Tyr Lys Asn Cys Glu Leu Asp Lys Asn Gln Arg Gln
                325                 330                 335
Cys Val Gln Tyr Ala Leu Lys Ala Arg Pro Leu Arg Cys Tyr Ile Pro
                340                 345                 350
Lys Asn Pro Tyr Gln Tyr Gln Val Trp Tyr Val Val Thr Ser Ser Tyr
            355                 360                 365
Glu Glu Tyr Leu Met Glu Ala Leu Ile Met Leu Asn Thr Ile Gly Leu
        370                 375                 380
Gly Met Gln His Tyr His Gln Ser Glu Glu Met Asn His Ile Ser Asp
385                 390                 395                 400
Ile Leu Asn Val Ala Arg Asp Leu Glu Arg Ile Leu Glu Met Ile Asp
                405                 410                 415
Lys Asn Asn Ala Phe Lys Ala Arg Gly Tyr Phe Gly Asp Arg Trp Asn
            420                 425                 430
Val Leu Asp Glu Leu Ile Trp Leu Gly Ser Ile Ile Asp Val Ile Leu
        435                 440                 445
Ser Glu Ile Asp Thr Phe Leu Ala Ser Ser Gly Gly Leu Tyr Cys Leu
450                 455                 460
```

Gly Gly Gly Cys Gly Asn Val Asp Pro Asp Glu Ser Ala Arg Ile Ser
465                 470                 475                 480

Ser Ala Leu Lys Arg Leu Glu Arg Val Met Arg Leu Ile Lys Leu Asp
            485                 490                 495

Ser Arg Ala Glu Gly Val Arg Thr Leu Leu Trp Thr Phe Ile Lys Ser
            500                 505                 510

Phe Gln Ala Leu Pro Tyr Ile Ala Leu Leu Val Met Leu Glu Glu
            515                 520             525

Ile Tyr Ala Val Ile Gly Met Met Phe Gly Lys Ile Ala Leu Val Asp
        530                 535                 540

Gly Thr Gln Ile Asn Arg Asn Asn Phe Gln Thr Phe Pro Gln Ala
545                 550                 555                 560

Val Leu Leu Phe Arg Cys Ala Thr Gly Glu Ala Trp Gln Glu Ile
                565                 570                 575

Leu Leu Ala Cys Ser Tyr Gly Lys Leu Cys Asp Pro Glu Ser Asp Tyr
            580                 585                 590

Ala Pro Gly Glu Glu Tyr Thr Cys Gly Thr Asn Phe Ala Tyr Tyr Tyr
        595                 600                 605

Phe Ile Ser Phe Tyr Met Leu Cys Ala Leu Phe Ile Ile Asn Leu Phe
        610                 615                 620

Val Ala Val Phe Met Asp Asn Phe Asp Tyr Leu Thr Arg Asp Trp Ser
625                 630                 635                 640

Ile Leu Gly Pro His His Leu Asp Glu Phe Lys Ala Ile Trp Ala Glu
                645                 650                 655

Tyr Asp Pro Glu Ala Lys Gly Arg Ile Lys His Leu Asp Val Val Thr
            660                 665                 670

Leu Leu Arg Arg Ile Gln Pro Pro Leu Gly Phe Gly Lys Phe Cys Pro
        675                 680                 685

His Arg Val Ala Cys Lys Arg Leu Val Gly Met Asn Met Pro Leu Asn
        690                 695                 700

Ser Asp Gly Thr Val Thr Phe Asn Ala Thr Leu Phe Ala Leu Val Arg
705                 710                 715                 720

Thr Ala Leu Lys Ile Lys Thr Glu Gly Asn Phe Glu Gln Ala Asn Glu
            725                 730                 735

Glu Leu Arg Ala Ile Ile Lys Ile Trp Lys Lys Arg Thr Ser Met Lys
            740                 745                 750

Leu Leu Asp Gln Val Ile Pro Pro Ile Gly Asp Asp Glu Val Thr Val
        755                 760                 765

Gly Lys Phe Tyr Ala Thr Phe Leu Ile Gln His Phe Arg Lys Phe
770                 775                 780

Met Lys Arg Gln Glu Glu Tyr Tyr Gly
785                 790

(2) INFORMATION FOR SEQ ID NO:5:

(i) SEQUENCE CHARACTERISTICS:
        (A) LENGTH: 26
        (B) TYPE: nucleic acid
        (C) STRANDEDNESS: single
        (D) TOPOLOGY: linear (ii) MOLECULE TYPE:

(ix) FEATURE:
        (A) NAME/KEY: misc_feature
        (B) LOCATION: 6
        (D) OTHER INFORMATION: /note= "inosine"

```
    (ix) FEATURE:
         (A) NAME/KEY: misc_feature
         (B) LOCATION: 12
         (D) OTHER INFORMATION: /note= "inosine"

(ix) FEATURE:
         (A) NAME/KEY: misc_feature
         (B) LOCATION: 21
         (D) OTHER INFORMATION: /note= "inosine"

(xi) SEQUENCE DESCRIPTION: SEQ ID NO:5:

ATHGYNATGY TNTTYTTYAT NTAYGC                                          26

(2) INFORMATION FOR SEQ ID NO:6:

(i) SEQUENCE CHARACTERISTICS:
         (A) LENGTH: 26
         (B) TYPE: nucleic acid
         (C) STRANDEDNESS: single
         (D) TOPOLOGY: linear (ii) MOLECULE TYPE:

(ix) FEATURE:
         (A) NAME/KEY: misc_feature
         (B) LOCATION: 6
         (D) OTHER INFORMATION: /note= "inosine"

(ix) FEATURE:
         (A) NAME/KEY: misc_feature
         (B) LOCATION: 15
         (D) OTHER INFORMATION: /note= "inosine"

(ix) FEATURE:
         (A) NAME/KEY: misc_feature
         (B) LOCATION: 18
         (D) OTHER INFORMATION: /note= "inosine"

(ix) FEATURE:
         (A) NAME/KEY: misc_feature
         (B) LOCATION: 21
         (D) OTHER INFORMATION: /note= "inosine"

(xi) SEQUENCE DESCRIPTION: SEQ ID NO:6:

TCRTCNARRT GRTGNGGNCC NARDAT                                          26

(2) INFORMATION FOR SEQ ID NO:7:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 2
         (D) OTHER INFORMATION: /note= "any amino acid except proline"

(ix) FEATURE:
         (A) NAME/KEY: Peptide
         (B) LOCATION: 3
         (D) OTHER INFORMATION: /note= "serine or threonine"

(ix) FEATURE:
         (A) NAME/KEY: Peptide
         (B) LOCATION: 4
         (D) OTHER INFORMATION: /note= "any amino acid except proline"

(xi) SEQUENCE DESCRIPTION: SEQ ID NO:7:

Asn Xaa Xaa Xaa
```

```
                                    -continued
1

(2) INFORMATION FOR SEQ ID NO:8:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1
         (D) OTHER INFORMATION: /note= "arginine or lysine"

(ix) FEATURE:
         (A) NAME/KEY: Peptide
         (B) LOCATION: 2
         (D) OTHER INFORMATION: /note= "any amino acid except proline"

(ix) FEATURE:
         (A) NAME/KEY: Peptide
         (B) LOCATION: 3
         (D) OTHER INFORMATION: /note= "any amino acid except proline"

(ix) FEATURE:
         (A) NAME/KEY: Peptide
         (B) LOCATION: 4
         (D) OTHER INFORMATION: /note= "serine or threonine"

(xi) SEQUENCE DESCRIPTION: SEQ ID NO:8:

Xaa Xaa Xaa Xaa
1

(2) INFORMATION FOR SEQ ID NO:9:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1
         (D) OTHER INFORMATION: /note= "serine or threonine"

(ix) FEATURE:
         (A) NAME/KEY: Modified-site
         (B) LOCATION: 2
         (D) OTHER INFORMATION: /note= "any amino acid except proline"

(ix) FEATURE:
         (A) NAME/KEY: Modified-site
         (B) LOCATION: 3
         (D) OTHER INFORMATION: /note= "any amino acid except proline"

(ix) FEATURE:
         (A) NAME/KEY: Modified-site
         (B) LOCATION: 4
         (D) OTHER INFORMATION: /note= "Aspartic acid or glutamic acid"

(xi) SEQUENCE DESCRIPTION: SEQ ID NO:9:

Xaa Xaa Xaa Xaa
1

(2) INFORMATION FOR SEQ ID NO:10:

(i) SEQUENCE CHARACTERISTICS:
         (A) LENGTH: 29 amino acids
```

(B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:10:

Met Phe Asp Glu Thr Trp His Lys Phe Asp Val His Gly Thr Gln Phe
1               5                   10                  15

Leu Asp Tyr Asn Asp Leu Pro Arg Phe Val Asn Ala Leu
            20                  25

(2) INFORMATION FOR SEQ ID NO:11:

(i) SEQUENCE CHARACTERISTICS:
           (A) LENGTH: 29 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:11:

Met Phe Tyr Glu Val Trp Glu Lys Phe Asp Pro Asp Ala Thr Gln Phe
1               5                   10                  15

Met Glu Phe Glu Lys Leu Ser Gln Phe Ala Ala Ala Leu
            20                  25

(2) INFORMATION FOR SEQ ID NO:12:

(i) SEQUENCE CHARACTERISTICS:
           (A) LENGTH: 29 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:12:

Met Phe Tyr Glu Val Trp Glu Lys Phe Asp Pro Asp Ala Thr Gln Phe
1               5                   10                  15

Ile Glu Phe Cys Lys Leu Ser Asp Phe Ala Ala Ala Leu
            20                  25

(2) INFORMATION FOR SEQ ID NO:13:

(i) SEQUENCE CHARACTERISTICS:
           (A) LENGTH: 29 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:13:

Met Phe Tyr Glu Val Trp Glu Lys Phe Asp Pro Asp Ala Thr Gln Phe
1               5                   10                  15

Ile Glu Phe Cys Lys Leu Ser Asp Phe Ala Ala Ala Leu
            20                  25

(2) INFORMATION FOR SEQ ID NO:14:

(i) SEQUENCE CHARACTERISTICS:
           (A) LENGTH: 29 amino acids
           (B) TYPE: amino acid
           (C) STRANDEDNESS: single
           (D) TOPOLOGY: linear -continued (ii) MOLECULE TYPE: peptide (xi) SEQUENCE DESCRIPTION: SEQ ID NO:14:

Met Phe Tyr Glu Ile Trp Glu Lys Phe Asp Pro Glu Ala Thr Gln Phe
1               5                   10                  15

Ile Glu Tyr Leu Ala Leu Ser Asp Phe Ala Asp Ala Leu
                20                  25

(2) INFORMATION FOR SEQ ID NO:15:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Met Phe Tyr Glu Thr Trp Glu Lys Phe Asp Pro Asp Ala Thr Gln Phe
1               5                   10                  15

Ile Asp Tyr Ser Arg Leu Ser Asp Phe Val Thr Asp Leu
                20                  25

(2) INFORMATION FOR SEQ ID NO:16:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Lys Ile Ser Tyr Leu Asp Val Leu Leu Ala Val Thr Gln Glu Val Leu
1               5                   10                  15

Gly Asp Thr Thr Glu Met Glu Ala Met Arg Leu Ser Ile
                20                  25

(2) INFORMATION FOR SEQ ID NO:17:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Lys Ile His Cys Leu Asp Ile Leu Phe Ala Leu Thr Lys Glu Val Leu
1               5                   10                  15

Gly Asp Ser Gly Glu Met Asp Ala Leu Lys Gln Thr Met
                20                  25

(2) INFORMATION FOR SEQ ID NO:18:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Glu Phe Lys Arg Ile Trp Ala Glu Tyr Asp Pro Glu Ala Lys Gly Arg
1               5                   10                  15

Ile Lys His Leu Asp Val Val Thr Leu Leu Arg Arg Ile
            20                  25

(2) INFORMATION FOR SEQ ID NO:19:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Glu Phe Lys Lys Ile Trp Ala Glu Tyr Asp Pro Glu Ala Thr Gly Arg
1               5                   10                  15

Ile Lys His Leu Asp Val Val Thr Leu Leu Arg Arg Ile
            20                  25

(2) INFORMATION FOR SEQ ID NO:20:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Glu Phe Lys Arg Ile Trp Ser Glu Tyr Asp Pro Glu Ala Lys Gly Arg
1               5                   10                  15

Ile Lys His Leu Asp Val Val Thr Leu Leu Arg Arg Ile
            20                  25

(2) INFORMATION FOR SEQ ID NO:21:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Glu Phe Lys Ala Ile Trp Ala Glu Tyr Asp Pro Glu Ala Lys Gly Arg
1               5                   10                  15

Ile Lys His Leu Asp Val Val Thr Leu Leu Arg Arg Ile
            20                  25

(2) INFORMATION FOR SEQ ID NO:22:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Glu Phe Lys Arg Ile Trp Ser Glu Tyr Asp Pro Glu Ala Lys Gly Arg

```
1               5                   10                  15
```
Ile Lys His Leu Asp Val Val Thr Leu Leu Arg Arg Ile
```
            20                  25
```

(2) INFORMATION FOR SEQ ID NO:23:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

Glu Phe Ile Arg Leu Trp Ser Glu Tyr Asp Pro Asp Ala Lys Gly Arg
```
1               5                   10                  15
```
Ile Lys His Leu Asp Val Val Thr Leu Leu Arg Lys Ile
```
            20                  25
```

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel consensus (Repeat I)

(xi) SEQUENCE DESCRIPTION: SEQ ID NO:24:

Gln Cys Ile Thr Met Glu Gly Trp Thr Asp Val Leu Tyr
```
1               5                   10
```

(2) INFORMATION FOR SEQ ID NO:25:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel Drosophila (Repeat I)

(xi) SEQUENCE DESCRIPTION: SEQ ID NO:25:

Gln Cys Val Thr Leu Glu Gly Trp Thr Asp Val Leu Tyr
```
1               5                   10
```

(2) INFORMATION FOR SEQ ID NO:26:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel Carp Skel (Repeat I)

(xi) SEQUENCE DESCRIPTION: SEQ ID NO:26:

Gln Cys Ile Thr Thr Glu Ser Trp Thr Asp Val Leu Tyr

```
1               5                    10
```

(2) INFORMATION FOR SEQ ID NO:27:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: Ca chan Rab. Skel, Human Br, Rat BrD,
            Rat BrC, Rat Aorta, Rab. Heart, Rat BrB, Rab. Br1, Rat
            BrA (Rpt I)

(xi) SEQUENCE DESCRIPTION: SEQ ID NO:27:

```
Gln Val Leu Thr Gly Glu Asp Trp Asn Ser Val Met Tyr
1               5                    10
```

(2) INFORMATION FOR SEQ ID NO:28:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel consensus (Repeat II)

(xi) SEQUENCE DESCRIPTION: SEQ ID NO:28:

```
Gln Ile Leu Thr Gly Glu Asp Trp Asn Ser Val Met Tyr
1               5                    10
```

(2) INFORMATION FOR SEQ ID NO:29:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: Calcium channel Drosophila (Repeat II)

(xi) SEQUENCE DESCRIPTION: SEQ ID NO:29:

```
Gln Ile Met Thr Gly Glu Asp Trp Asn Ala Val Met Tyr
1               5                    10
```

(2) INFORMATION FOR SEQ ID NO:30:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: Calcium channel Carp Skel (Repeat II)

(xi) SEQUENCE DESCRIPTION: SEQ ID NO:30:

```
Gln Val Leu Thr Gly Glu Glu Trp Asp Ser Ile Met Tyr
1               5                    10
```

(2) INFORMATION FOR SEQ ID NO:31:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel Rabbit Skel (Repeat
            II)

(xi) SEQUENCE DESCRIPTION: SEQ ID NO:31:

Gln Cys Ile Thr Met Glu Gly Trp Thr Asp Val Leu Tyr
1             5                  10

(2) INFORMATION FOR SEQ ID NO:32:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel Human brain and Rat
            Br-D (Repeat II)

(xi) SEQUENCE DESCRIPTION: SEQ ID NO:32:

Gln Ile Leu Thr Gly Glu Asp Trp Asn Ala Val Met Tyr
1             5                  10

(2) INFORMATION FOR SEQ ID NO:33:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel Rat Br-C, Rat Aorta,
            Rab. Heart, Rat Br-B, Rab. Br-1, Rat Br-A (Repeat II)

(xi) SEQUENCE DESCRIPTION: SEQ ID NO:33:

Gln Ile Leu Thr Gly Glu Asp Trp Asn Ser Val Met Tyr
1             5                  10

(2) INFORMATION FOR SEQ ID NO:34:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel consensus (Repeat I)

(xi) SEQUENCE DESCRIPTION: SEQ ID NO:34:

Arg Leu Met Thr Gln Asp Tyr Trp Glu Asn Leu Tyr Gln
1             5                  10

```
(2) INFORMATION FOR SEQ ID NO:35:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (viii) POSITION IN GENOME:
         (A) CHROMOSOME/SEGMENT: sodium channel para, Rat BrII, Rat
             BrIII, Rat Heart, Rat Skel mu1, Eel(Repeat I)

(xi) SEQUENCE DESCRIPTION: SEQ ID NO:35:

Arg Leu Met Thr Gln Asp Phe Trp Glu Asp Leu Tyr Gln
1               5                   10

(2) INFORMATION FOR SEQ ID NO:36:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (viii) POSITION IN GENOME:
         (A) CHROMOSOME/SEGMENT: sodium channel consensus (Repeat II)

(xi) SEQUENCE DESCRIPTION: SEQ ID NO:36:

Arg Val Leu Cys Gly Glu Trp Ile Glu Thr Met Trp Asp
1               5                   10

(2) INFORMATION FOR SEQ ID NO:37:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (viii) POSITION IN GENOME:
         (A) CHROMOSOME/SEGMENT: sodium channel para (Repeat II)

(xi) SEQUENCE DESCRIPTION: SEQ ID NO:37:

Arg Val Leu Cys Gly Glu Trp Ile Glu Ser Met Trp Asp
1               5                   10

(2) INFORMATION FOR SEQ ID NO:38:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (viii) POSITION IN GENOME:
         (A) CHROMOSOME/SEGMENT: sodium channel Rat BrII, Rat BrIII
             (Repeat II)

(xi) SEQUENCE DESCRIPTION: SEQ ID NO:38:

Arg Val Leu Cys Gly Glu Trp Ile Glu Ser Met Trp Asp
1               5                   10
```

(2) INFORMATION FOR SEQ ID NO:39:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Rat Heart, Rat Skel mu1
            (Repeat II)

(xi) SEQUENCE DESCRIPTION: SEQ ID NO:39:

Arg Ile Leu Cys Gly Glu Trp Ile Glu Ser Met Trp Asp
1               5                   10

(2) INFORMATION FOR SEQ ID NO:40:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Eel (Repeat II)

(xi) SEQUENCE DESCRIPTION: SEQ ID NO:40:

Arg Ala Leu Cys Gly Glu Trp Ile Glu Ser Met Trp Asp
1               5                   10

(2) INFORMATION FOR SEQ ID NO:41:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel consensus (Repeat III)

(xi) SEQUENCE DESCRIPTION: SEQ ID NO:41:

Thr Val Ser Thr Phe Glu Gly Trp Pro Glu Leu Leu Tyr
1               5                   10

(2) INFORMATION FOR SEQ ID NO:42:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel Drosophila (Repeat
            III)

(xi) SEQUENCE DESCRIPTION: SEQ ID NO:42:

Thr Val Ser Thr Phe Glu Gly Trp Pro Gly Leu Leu Tyr
1               5                   10

```
(2) INFORMATION FOR SEQ ID NO:43:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel Carp Skel (Repeat III)

(xi) SEQUENCE DESCRIPTION: SEQ ID NO:43:

Thr Ile Ser Thr Phe Glu Gly Trp Pro Glu Ile Leu Tyr
1               5                   10

(2) INFORMATION FOR SEQ ID NO:44:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: Ca chan Rab. Skel, Human Br, Rat BrD,
            Rat BrC, Rat Aorta, Rab Heart, Rat BrB, Rabbit Br1, Rat
            BrA (Repeat III)

(xi) SEQUENCE DESCRIPTION: SEQ ID NO:44:

Thr Val Ile Ser Thr Phe Glu Gly Trp Pro Glu Ile Leu Tyr
1               5                   10

(2) INFORMATION FOR SEQ ID NO:45:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel consensus (Repeat IV)

(xi) SEQUENCE DESCRIPTION: SEQ ID NO:45:

Arg Cys Ala Thr Gly Glu Ala Trp Gln Glu Ile Met Leu
1               5                   10

(2) INFORMATION FOR SEQ ID NO:46:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: calcium channel Drosophila (Repeat IV)

(xi) SEQUENCE DESCRIPTION: SEQ ID NO:46:

Arg Ser Ala Thr Gly Glu Ala Trp Glu Ile Met Met
1               5                   10

(2) INFORMATION FOR SEQ ID NO:47:
```

(i) SEQUENCE CHARACTERISTICS:
           (A) LENGTH: 13 amino acids
           (B) TYPE: amino acid
           (C) STRANDEDNESS: single
           (D) TOPOLOGY: linear (ii) MOLECULE TYPE: peptide (viii) POSITION IN GENOME:
           (A) CHROMOSOME/SEGMENT: calcium channel Carp Skel (Repeat IV)

(xi) SEQUENCE DESCRIPTION: SEQ ID NO:47:

Arg Val Ala Thr Gly Glu Gln Trp Pro Lys Val Ile Leu
1               5                  10

(2) INFORMATION FOR SEQ ID NO:48:

(i) SEQUENCE CHARACTERISTICS:
           (A) LENGTH: 13 amino acids
           (B) TYPE: amino acid
           (C) STRANDEDNESS: single
           (D) TOPOLOGY: linear (ii) MOLECULE TYPE: peptide (viii) POSITION IN GENOME:
           (A) CHROMOSOME/SEGMENT: Ca chan Rab. Skel, Human Br, Rat BrD,
               Rat BrC, Rat Aorta, Rab. Heart, Rat BrB, Rab. Br1, Rat
               BrA (Repeat IV)

(xi) SEQUENCE DESCRIPTION: SEQ ID NO:48:

Arg Cys Ala Thr Gly Glu Gln Trp Pro Lys Val Ile Leu
1               5                  10

(2) INFORMATION FOR SEQ ID NO:49:

(i) SEQUENCE CHARACTERISTICS:
           (A) LENGTH: 13 amino acids
           (B) TYPE: amino acid
           (C) STRANDEDNESS: single
           (D) TOPOLOGY: linear (ii) MOLECULE TYPE: peptide (viii) POSITION IN GENOME:
           (A) CHROMOSOME/SEGMENT: sodium channel consensus (Repeat III)

(xi) SEQUENCE DESCRIPTION: SEQ ID NO:49:

Gln Val Ala Thr Phe Lys Gly Trp Met Asp Ile Met Tyr
1               5                  10

(2) INFORMATION FOR SEQ ID NO:50:

(i) SEQUENCE CHARACTERISTICS:
           (A) LENGTH: 13 amino acids
           (B) TYPE: amino acid
           (C) STRANDEDNESS: single
           (D) TOPOLOGY: linear (ii) MOLECULE TYPE: peptide (viii) POSITION IN GENOME:
           (A) CHROMOSOME/SEGMENT: sodium channel para, Rat BrII, Rat
               BrIII, Rat Heart (Repeat III)

(xi) SEQUENCE DESCRIPTION: SEQ ID NO:50:

Gln Val Ala Thr Phe Lys Gly Trp Ile Gln Ile Met Asn
1               5                  10

(2) INFORMATION FOR SEQ ID NO:51:

```
    (i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Rat Skel mu1 (Repeat
            III)

(xi) SEQUENCE DESCRIPTION: SEQ ID NO:51:

Gln Val Ala Thr Phe Lys Gly Trp Met Asp Ile Met Tyr
1               5                   10

(2) INFORMATION FOR SEQ ID NO:52:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Eel (Repeat III)

(xi) SEQUENCE DESCRIPTION: SEQ ID NO:52:

Gln Val Ser Thr Phe Lys Gly Trp Met Asp Ile Met Tyr
1               5                   10

(2) INFORMATION FOR SEQ ID NO:53:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel consensus (Repeat IV)

(xi) SEQUENCE DESCRIPTION: SEQ ID NO:53:

Gln Ile Thr Thr Ser Ala Gly Trp Asp Gly Ile Leu Ala
1               5                   10

(2) INFORMATION FOR SEQ ID NO:54:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel para (Repeat IV)

(xi) SEQUENCE DESCRIPTION: SEQ ID NO:54:

Gln Met Ser Thr Ser Ala Gly Trp Asp Gly Val Leu Asp
1               5                   10

(2) INFORMATION FOR SEQ ID NO:55:

(i) SEQUENCE CHARACTERISTICS:
```

```
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Rat BrII, Rat BrIII,
            Rat Heart (Repeat IV)

(xi) SEQUENCE DESCRIPTION: SEQ ID NO:55:

Gln Ile Ser Thr Ser Ala Gly Trp Asp Gly Val Leu Asp
1               5                  10

(2) INFORMATION FOR SEQ ID NO:56:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Rat Skel mu1 (Repeat
            IV)

(xi) SEQUENCE DESCRIPTION: SEQ ID NO:56:

Glu Ile Thr Thr Ser Ala Gly Trp Asp Gly Leu Leu Asn
1               5                  10

(2) INFORMATION FOR SEQ ID NO:57:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (viii) POSITION IN GENOME:
        (A) CHROMOSOME/SEGMENT: sodium channel Eel (Repeat IV)

(xi) SEQUENCE DESCRIPTION: SEQ ID NO:57:

Glu Ile Thr Thr Ser Ala Gly Trp Asp Gly Leu Leu Leu
1               5                  10
```

GENE ENCODING AN INVERTEBRATE ALPHA1 CALCIUM CHANNEL SUBUNIT

FIELD OF THE INVENTION

The present invention relates generally to the voltage-dependent calcium channel multigene family. More particularly, the present invention relates to the characterization and isolation of a neuronal invertebrate calcium channel $\alpha_1$ subunit. More particular it also relates to $\alpha_1$ lcalcium channel subunit from *Drosophila melanogaster*.

BACKGROUND OF THE INVENTION

Early electrophysiological studies on invertebrate preparations revealed the presence of calcium currents and suggested the presence of multiple types of voltage-dependent calcium channels (reviewed by Hille, B., (1992),-In: *Ion Channels of Excitable Membranes*, 2nd Ed., Sinauer, Sunderland, Mass.). Continuing studies of calcium channels have shown that they are ubiquitous since they are found in excitable cells in species ranging from *Paramecium* to humans. Calcium channels are involved in many cell functions including: membrane excitability, synaptic transmission, and differentiation (Tsien et al., (1988), *Trends Neurosci.*, vol. 11, pp. 431–438). Voltage-dependent calcium channels have been studied extensively in vertebrate neuronal tissue using electrophysiological and pharmacological approaches and as a result have been divided into four classes designated L, N, T, and P (Bean, B. P., (1989), *Annu. Rev., Physiol.*, vol 51, pp. 367–384; Hess, P., (1990), *Annu. Rev. Neurosci.*, vol. 13, pp. 1337–1356).

Gene cloning studies, which up to this point have focused exclusively on vertebrate species, have helped to elucidate the molecular nature of calcium channel structure and have suggested a remarkable degree of channel heterogeneity beyond that predicted from physiological and pharmacological approaches. This molecular diversity of calcium channels arises from several mechanisms. Calcium channels are comprised of multiple subunits designated $\alpha_1$, $\alpha_2$, $\beta$, $\gamma$, and $\delta$ (Catterall, W. A., (1991a), *Cell*, vol. 64, pp. 871–874; Catterall, W. A., (1991b), *Science*, vol. 253, pp. 1499–1500). The $\alpha_2$ and $\delta$ subunits are encoded by the same gene and are cleaved during posttranslational processing whereas each of the other subunits arise from different genes. One way that calcium channel diversity arises is through the presence of a family of genes each encoding genetic variants of a given subunit. For example, in rat brain the $\alpha_1$ subunit appears to be encoded by a family of at least five different genes (Snutch et al., (1990), *Proc. Natl. Acad. Sci. USA*, vol. 87, pp. 3391–3395; Snutch et al., (1991), *Neuron*, vol. 7, pp. 45–57; Hui et al., (1991), *Neuron*, vol. 7, pp. 35–44; Starr et al., (1991), *Proc. Natl. Acad. Sci. USA*, vol. 88, pp. 5621–5625; Dubel et al., (1992), *Proc. Natl. Acad. Sci. USA*, vol. 89, pp. 5058–5062; Soong et al., (1993), *Science*, vol. 260, pp. 1133–1136). For each member of the gene family further diversity is introduced by alternative splicing (Biel et al., (1990), *FEBS Lett.*, vol. 269, pp. 409–412; Koch et al., (1990), *J. Biol. Chem.*, vol. 265, pp. 17786–17791; Perez-Reyes et al., (1990), *J. Biol. Chem.*, vol. 265, pp. 20430–20436; Snutch et al., (1991), *Neuron*, vol. 7, pp. 45–57). Recent studies point to the existence of similar molecular diversity for the other subunits as well (Williams et al., (1992a), Science, vol. 257, pp. 389–395; Williams et al., (1992b), *Neuron*, vol. 8, pp. 71–84). If each subunit variant can interact with more than one form of each of the other subunits to form functional channels, then there is a potential for even further molecular diversity.

Although studies of the molecular diversity of calcium channels in *Drosophila* are just beginning, there is evidence for structural and functional heterogeneity in this system. Binding of phenylalkylamines (calcium channel blocking agents) to *Drosophila* head extracts showed curvilinear Scatchard plots indicative of multiple receptor classes differing in ligand affinity (Greenberg et al., (1989), *Insect Biochem.*, vol. 19, 309–322). Pelzer et al., (1989), *EMBO J.*, vol. 8, pp. 2365–2371, reported at least 8 distinct voltage-sensitive calcium channels in *Drosophila* head membranes following reconstitution into phospholipid bilayers. Patch clamp studies on cultured embryonic *Drosophila* myocytes and neurons also showed variability of channel properties, suggesting at least two types of neuronal calcium channels in *Drosophila* (Leung, H.T. and Byerly, L. (1991), *J. Neurosci.*, vol. 11, pp 3047–3059). Further evidence for channel heterogeneity comes from differential sensitivity of *Drosophila* neuronal calcium channels to a purified toxin from the spider *Hololena curta* (Leung, H. T. and Byerly, L., (1991), *J. Neurosci.*, vol. 11, pp. 3047–3059). This heterogeneity is further supported in another neuronal invertebrate (*Periplaneta americana*) where radiotracer flux studies have demonstrated the presence of dihydropyridine-insensitive and -sensitive components of phenylalkylamine-sensitive calcium uptake in nervous system and skeletal muscle membranes, respectively (Skeer et al., (1992), *Insect Biochem. Molec. Biol.*, vol. 22, pp. 539–545).

Given the heterogeneity of calcium channels in invertebrates, Drosophila provides an ideal system for a molecular genetic approach to define the significance of channel diversity by mutating individual subunit genes and determining the physiological and behavioral consequences.

Other ion channels have also been reported to date. For example, electrophysiological studies of ligand-gated ion currents in invertebrate nerve and muscle cells provide evidence for the existence of chloride channels gated by glutamate, histamine, and taurine, as well as those gated by γ-aminobutyric acid ("GABA") (Sattelle, D. B., (1990), *Adv. Insect Physiol.*, vol. 22, pp. 41–56 and Lummis et al., (1990), *Annu. Rev. Entomol.*, vol. 35, pp. 345–377). Although these findings imply the existence of a large and diverse gene family encoding ligand-gated chloride channels in invertebrates, very little is known about homologous channels of invertebrates. In ffrench-Constant et al., (1991), *Proc Nati. Acad. Sci. USA*, vol. 88, pp. 7209–7213, a *Drosophila melanogaster* cDNA having significant predicted amino acid sequence identity to vertebrate ligand-gated chloride channel genes was isolated and mapped to a genetic locus ("Rdll") that confers resistance to cyclodiene insecticides and other blockers of GABA-gated chloride channels. Rdl was shown to encode a GABA subunit by the expression of functional homomultimeric GABA receptors in *Xenopus oocytes* following injection with Rdl MRNA (ffrench-Constant et al., (1993), *Nature*, vol. 363, pp. 449–451).

The only other example of a ligand-gated chloride channel gene from an invertebrate species is a GABA receptor β-like subunit gene isolated from the pond snail, *Lymnaea stagnalis* (Harvey et al., (1991), *EMBO J.*, vol. 10, pp. 3239–3245). The functional relationship of the product encoded by this gene to vertebrate GABA receptor β subunits was corroborated Dy the formation of a functional chimeric receptor with properties similar to vertebrate α/β heteromultimers when the gene was co-expressed with a vertebrate a subunit in *Xenopus oocytes*.

The characterization and isolation of a neuronal invertebrate $\alpha_1$ calcium channel subunit gene(s) would be useful in the cloning of calcium channel subunits from other invertebrate preparations of physiological or economic importance for purposes such as screening chemical agents to identify chemical agents which specifically interact with, and bind to, the calcium channel receptor on the surface of a cell, such as, for example, organic calcium channel blocking agents, e.g., phenylalkylamines.

BRIEF SUMMARY OF THE INVENTION

The primary object of the present invention is the isolation and characterization of an invertebrate neuronal calcium channel $\alpha_1$ subunit gene(s).

The present invention provides for the isolation of genomic DNA fragment(s) from *Drosophila melanogaster* which encode a conserved amino acid sequence unique to the voltage-dependent calcium channel multigene family. Polymerase chain reaction ("PCR")-based homology and screening of cDNA libraries with homologous probe were utilized to isolate the genomic DNA fragment(s) of the invention. Using PCR, the first neuronal invertebrate calcium channel subunit gene was cloned. That is, the neuronal calcium channel $\alpha_1$ subunit gene was cloned from *Drosophila melanogaster*, and desginated herein as "Dmca1D". The cDNA clones corresponding to the DNA fragments are designated N1, W8A, SH22C, and SH22D.

The DNA sequence expressing the corresponding amino acid sequences encoding the calcium channel $\alpha_1$ subunit gene(s) of the invention can be cloned into any suitable expression vector, such as, for example, plasmid DNA, viral DNA including human viruses, animal viruses and invertebrate viruses and bacteriophages to form a recombinant expression system which directs the expression of the calcium channel $\alpha_1$ subunit of the invention. It is understood that this expression system can be expressed in any suitable host cell to form a functional recombinant calcium channel receptor.

In another aspect of the invention, there is provided a method of expressing a functional neuronal invertebrate $\alpha_1$ calcium channel receptor comprising (a) transforming a host cell with the gene of the present invention e.g., gene encoding the neuronal calcium channel $\alpha_1$ subunit from *Drosophila melanogaster*, and (b) facilitating expression of the gene(s) in the host cell, thereby forming a functional ion channel receptor which exhibits similar pharmacological properties of calcium channel in neuronal invertebrate tissue.

In still another aspect of the invention, there is provided a method of screening a chemical agent for effectiveness as a pesticide, comprising (a) facilitating expression of the gene of the invention e.g., gene encoding the calcium channel $\alpha_1$ subunit from *Drosophila melanogaster*, in a host thereby forming a functional calcium channel receptor, (b) exposing the host to a chemical agent having pesticidal activity, and (c) evaluating the exposed host to determine if the functional calcium channel receptor is the target site for the pesticidal activity of the chemical agent.

In still a further aspect of the invention, there is provided a method of identifying compositions which specifically interact with, and bind to, the calcium channel receptor on the surface of a cell comprising (a) contacting a vertebrate or invertebrate cell containing the gene of the invention e.g., gene encoding the calcium channel $\alpha_1$ subunit from *Drosophila melanogaster*, with a plurality of chemical agents, and (b) determining those chemical agents which bind to the calcium channel expressed in the cell, thereby identifying chemical agents which specifically interact with, and bind to, the calcium channel.

BRIEF DESCRIPTION OF THE DRAWINGS

Figure 2A-1:
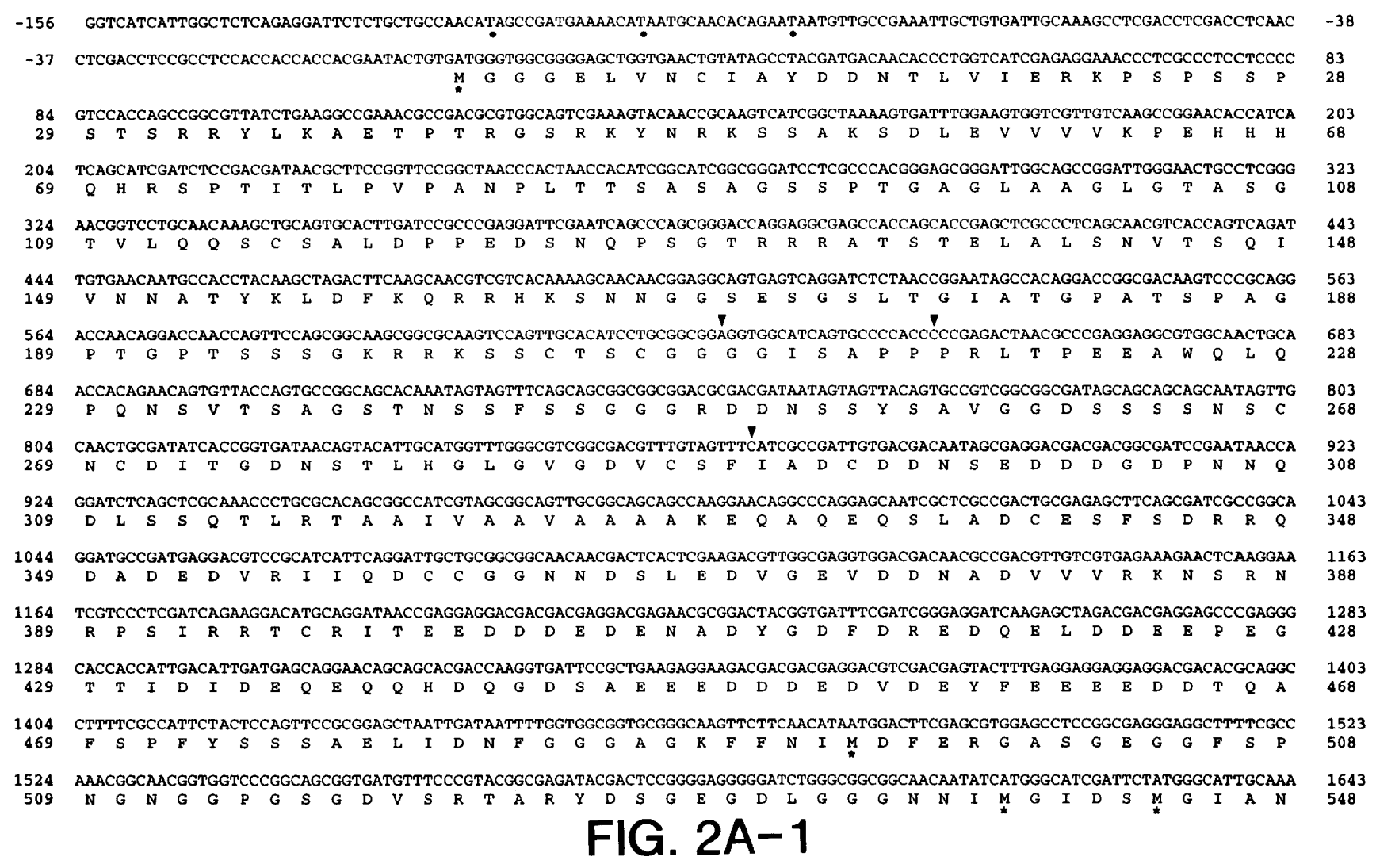
Figure 2A-2:
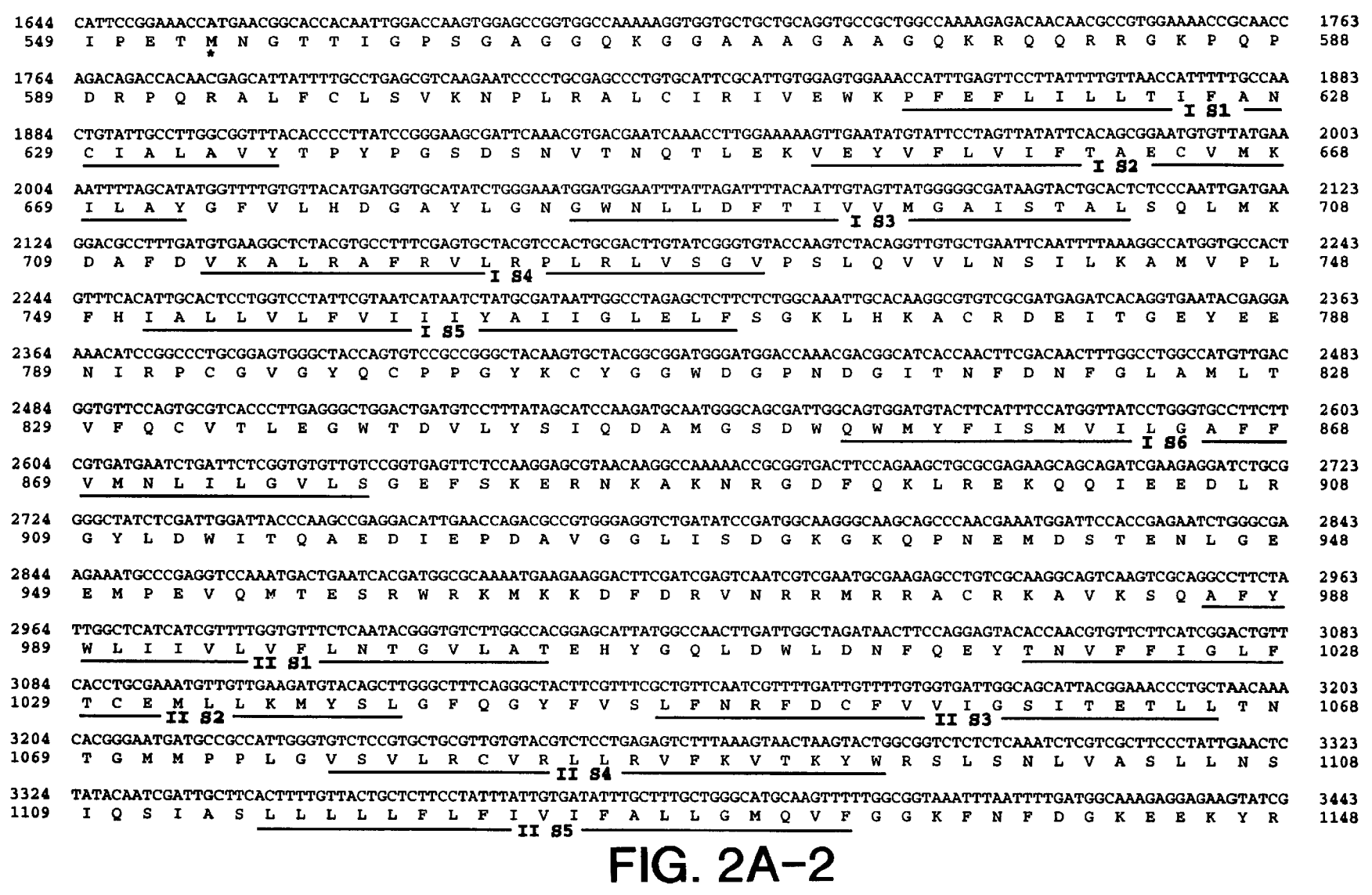
Figure 2A-3:
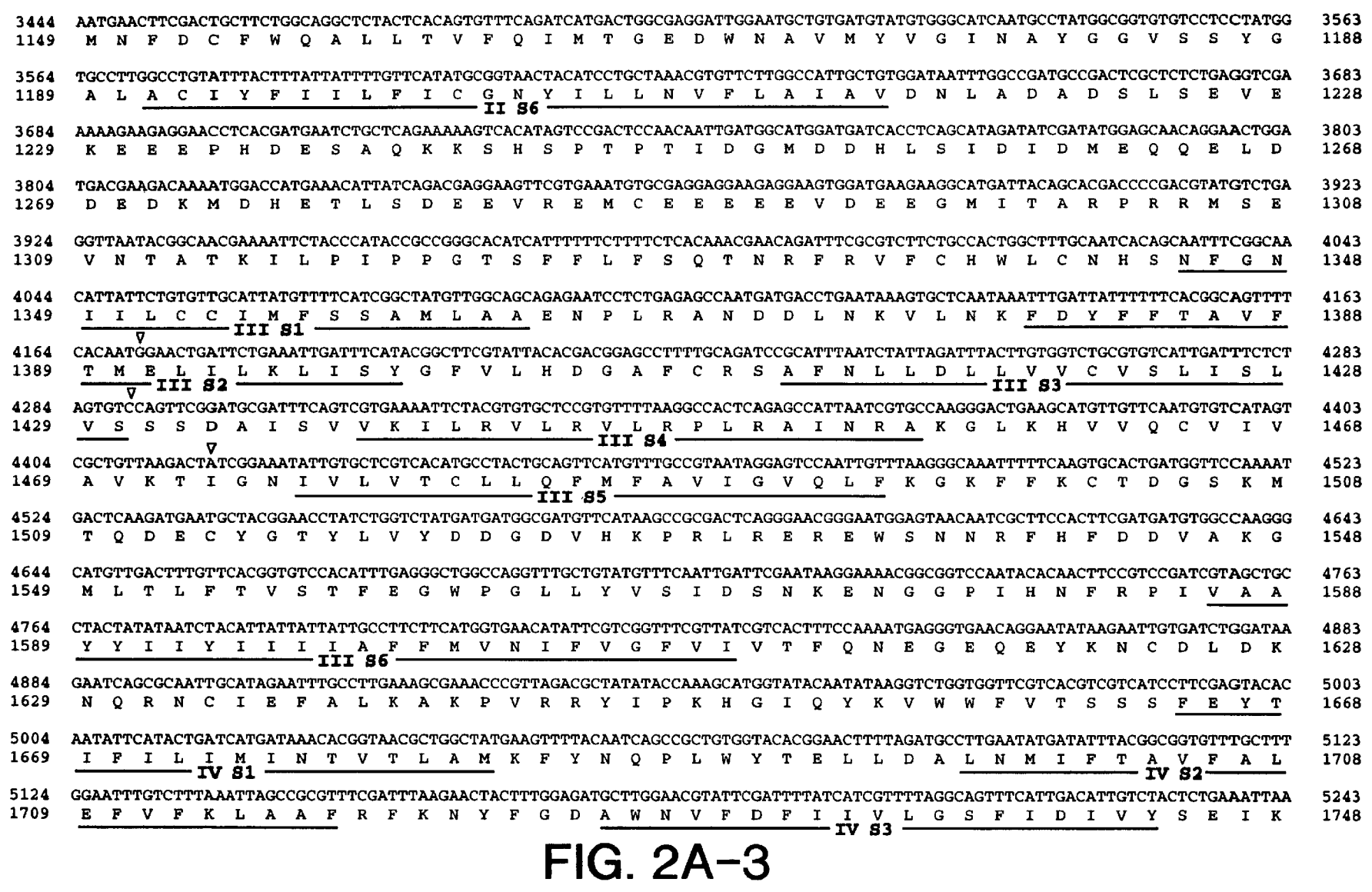
Figure 2A-4:
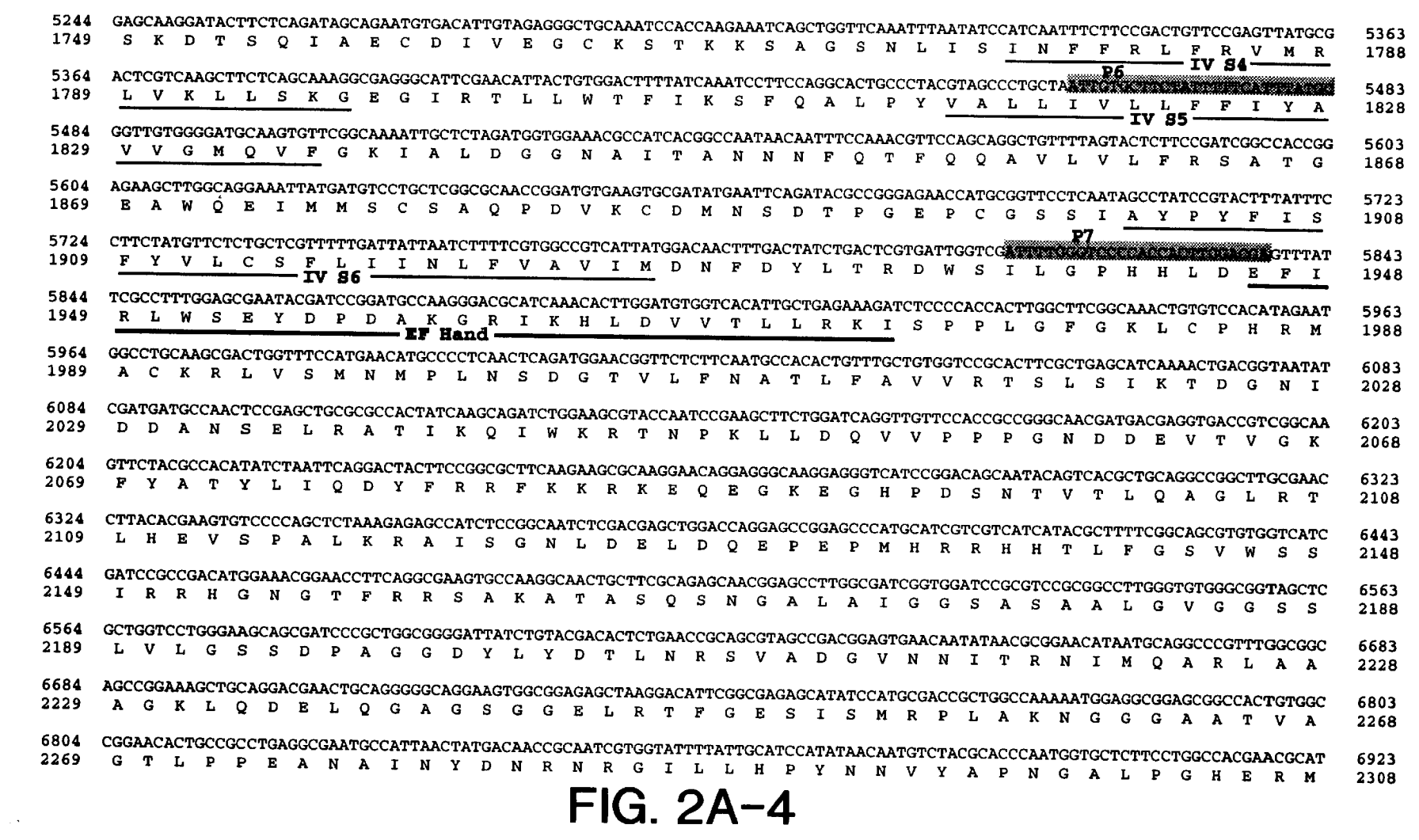

FIGS. 2A–2C illustrate the nucleotide sequence ("SEQ. ID. NO. 1") and deduced amino acid sequence ("SEQ. ID. NO. 2") of the cDNA encoding the *Drosophila* neuronal $\alpha_1$ subunit of the invention.

FIG. 2*a* [SEQ. I.D. NOS: 1 & 2]—2 sequences aligned.

FIG. 2*b*—SEQ. I.D. No. 1.

FIG. 2*c*—SEQ. I.D. No. 2.

FIG. 7[SEQ. ID. NOS: 3 & 4]. illustrates the alignment of the deduced amino acid sequences of $\alpha_1$ subunits from *Drosophila* (upper) and rabbit skeletal muscle (lower) [The transmembrane domains are shaded in gray and their identity is shown above in bold lettering. Nonconservative amino acid substitutions in regions of interest are indicated by filled triangles. The hatched bar indicates the phenylalkylamine-binding fragment. The black bars underline dihydropyridine-binding fragments].

DETAILED DESCRIPTION OF THE INVENTION

Figure 1A:
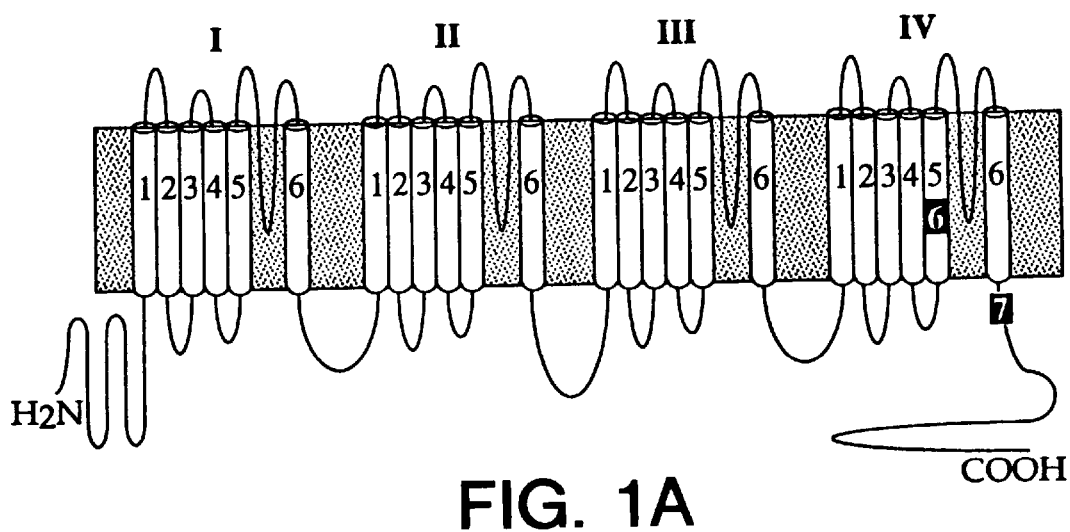
FIG. 1A and 1B are a schematic diagrams depicting a strategy for cloning and the relationship of cDNA clones encoding the neuronal calcium channel $\alpha_1$ subunit from *Drosophila* [A, Cartoon showing the general structure of $\alpha_1$ subunits. Black boxes labeled 6 & 7, identify the position of primers used for successful amplification of a portion of genomic DNA encoding the *Drosophila* $\alpha_1$ sequence. The region extending diagonally from the 3' end of W8A indicates an alternatively spliced sequence which is not present in clone SH22C. The small open boxes in SH22D indicate positions of the alternative splice regions studied in Table 1. The large rectangular box indicates the open reading frame for the *Drosophila* $\alpha_1$ subunit starting with the first possible methionine codon (designated met1 herein). The positions of the repeats (I–IV) are shown as shaded gray boxes within the open reading frame].

The present invention provides for the characterization and isolation of a neuronal calcium channel $\alpha_1$ subunit gene cloned from *Drosophila melanogaster*, and designated herein as "Dmca1D". The present invention provides the complete sequence of a calcium channel $\alpha_1$ subunit cDNA cloned from a Drosophila head cDNA library. This appears to be the first neuronal invertebrate calcium channel subunit cloned using a PCR approach which relied on sequence similarity to previously cloned calcium channels from vertebrate species. The approach used in the present invention allowed for the rapid cloning of related genes from evolutionarily distant organisms and should be applicable for the cloning of al subunits from other invertebrate preparations of physiological or economic importance.

The present invention provides for the isolation of genomic DNA fragment(s) from *Drosophila melanogaster* which encode a conserved amino acid sequence unique to the voltage-dependent calcium channel multigene family. Polymerase chain reaction ("PCR")-based homology was utilized to isolate genomic DNA fragment(s) which were used to probe a cDNA library. Using these techniques, the first neuronal invertebrate calcium channel subunit genes were cloned. More particularly, these techniques yielded four $\alpha_1$ cDNA clones, designated N1, W8A, SH22C, and SH22D the open reading frame of the combined cDNA clones (primarily N1, W8A, and SH22C) encompasses the Dmca1D gene sequence of the present invention.

It is understood that the cDNAs encoding the clones designated N1, W8A, SH22C, and SH22D (whose combination encompasses the open reading frame of the Dmca1D gene) are for purposes of illustration only, and the existence of a diverse family of genes in *Drosophila melanogaster* that are structurally related to the voltage-dependent calcium channel gene family of invertebrates is supported by the present invention.

The genomic sequence of the invention, designated Dmca1D, exhibits the conserved features commonly found in members of the family of voltage-dependent calcium channel genes. More specifically, the Dmca1D genomic sequence encodes a deduced protein estimated to contain 2516 amino acids with a predicted molecular weight of 276,493 kDa. The deduced protein shares many features with vertebrate homologues including: (1) 4 repeat structures each containing 6 transmembrane domains; (2) a conserved ion selectivity filter region between transmembrane domains 5 and 6; and (3) an EF hand in the carboxy tail. The *Drosophila* subunit is unusual in that the initial amino and terminal carboxy tails are much longer than those of the vertebrate homologues. The region corresponding to the last transmembrane domain (IVS6) and the adjacent cytoplasmic domain have been postulated to form a phenylalkylamine-binding site in vertebrate calcium channels. This region is completely conserved in the *Drosophila* sequence while domains thought to be involved in dihydropyridine binding show numerous changes. Since the *Drosophila* subunit of the invention exhibits 78.3% sequence similarity to the type D calcium channel $\alpha_1$ subunit from rat brain, it has been designated *Drosophila melanogaster* calcium channel alpha1 type D subunit ("Dmca1D"). This appears to be the first report of a neuronal calcium channel subunit sequence from an invertebrate species. In situ hybridization using digoxigenin-labeled probes shows that Dmca1D is highly expressed in the embryonic nervous system. Northern analysis shows that Dmca1D cDNA hybridizes to three size classes of mRNA (9.5, 10.2 and 12.5 kb) in heads, but only two classes (9.5 and 12.5 kb) in bodies and legs. PCR analysis of cDNA versus genomic DNA suggests that the Dmca1D message undergoes alternative splicing with more heterogeneity appearing in head and embryonic extracts than in bodies and legs.

In accordance with one embodiment of the invention, there is provided an isolated gene and/or gene fragment or portion thereof comprising a DNA molecule encoding a calcium channel $\alpha_1$ subunit from *Drosophila melanogaster*. Preferably, the DNA molecule of the invention encodes for an amino acid sequence, or mutant thereof, corresponding to Dmca1D, as shown in FIG. 2 (SEQ. ID. NO. 2). The DNA molecule of the invention preferably comprises a nucleotide sequence, or a mutant DNA sequence thereof, corresponding to Dmca1D, as shown in FIG. 2 (SEQ. ID. NO. 1). It is understood that any modifications, e.g., insertions, deletions, mutations, recombinants, etc., of the DNA nucleotide and/or corresponding amino acid sequence(s) are within the scope of the present invention provided that the modified sequence (s) encode for a gene, its homologs or a fragment thereof producing a calcium channel $\alpha_1$ subunit from *Drosophila melanogaster*. In addition, this subunit should exhibit pharmacological properties of the native calcium channel $\alpha_1$ subunit in neuronal invertebrate tissue.

Recombinant DNA techniques are used to insert the DNA sequences of the invention (e.g. gene encoding the calcium channel $\alpha_1$ subunit from *Drosophila melanogaster*) from *Drosophila melanogaster* into an appropriate expression vector, i.e., a vector which contains the necessary elements for the transcription and translation of the inserted coding sequences. A large number of vector systems known in the art can be used, such as, plasmids, bacteriophage virus or other modified viruses. Suitable vectors include, but are not limited to the following viral vectors such as lambda vector system gt11, gtWES.tB, Charon 4, and plasmid vectors such as pBR322, pBR325, pACYC177, pACYC184, pAR series, pKK223-3, pUC8, pUC9, pUC18, pUC19, pLG339, pR290, pKC37, pKC101 and other similar systems. The DNA sequences are cloned into the vector using standard cloning procedures in the art, as described by Sambrook et al., (1989), In: *Molecular Cloning: A Laboratory Manual,* 2nd ed., Cold Springs Harbor Laboratory Press, Cold Spring Harbor, N.Y., which disclosure is hereby incorporated by reference.

The recombinant DNA molecule (e.g., vector+sequence of invention) can then be introduced into appropriate host cells, including but not limited to bacteria, virus, yeast, vertebrate or invertebrate cells or the like. The vector system must be compatible with the host cell used. The recombinant vectors can be introduced into the host cells via transformation, transfection or infection using standard techniques in the art. A variety of host cell systems can be used to express the calcium channel $\alpha_1$ subunit gene of the invention. For example, host cell systems include, but are not limited to the following: bacteria transformed with bacteriophage DNA, plasmid DNA or cosmid DNA such as E. coli JM103, E. coli C600, E. coli C04, E. coli DH20 and E. coli TB1; microorganisms such as yeast containing yeast vectors; mammalian cell systems infected with virus (vaccinia virus, adenovirus, etc.); neuronal invertebrate cell systems infected with virus (baculovirus).

In order to obtain efficient expression of the calcium channel $\alpha_1$ subunit gene, a promoter must be present in the expression vector. RNA polymerase normally binds to the promoter and initiates transcription of a gene or a group of linked genes and regulatory elements (operon). Promoters vary in their strength, i.e., ability to promote transcription. For the purpose of expressing the gene of the invention, it is desirable to use strong promoters in order to obtain a high level of transcription and, hence, expression of the gene. Depending upon the host cell system utilized, any one of a number of suitable promoters can be used, such as, the lac promoter, trp promoter, recA promoter, ribosomal RNA promoter, the $P_R$ and $P_L$ promoters of coliphage lambda, the copia (Flavell, A.J., Levis, R., Simon, M.A., and Rubin, G.M. (1981) Nucleic Acid Research 9, 6279–6291), heatshock 70 (Ingolia, T.D., Craig, E.A., and McCarthy, B.J. (1980) cell 21, 669–679) or metallothionein promoters (Maroni, G., Otto, E. and Lastowski-Perry, D. (1986) Genetics 112, 493–504) from Drosophila, and others including but not limited to lacUV5, ompF, bla, 1pp and the like, nos promoter, the small subunit ribulose bisphosphate carboxylase genes, the small subunit chlorophyll A/B binding polypeptide, the 35S promoter of cauliflower mosaic virus, and promoters isolated from plant genes, including the Pto promoter itself (Vallejos et al., (1986), Genetics, vol. 112, pp. 93–105, which disclosure is hereby incorporated by reference) to direct high levels of transcription of adjacent DNA segments.

Host cell strains and expression vectors can be chosen which inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the PL promoter of lambda can be induced by an increase in temperature in host cells containing a temperature sensitive lambda repressor, e.g., c1857. In this way, greater than 95% of the promoter-directed transcription may be inhibited in uninduced cells. Thus, expression of the gene of the invention can be controlled.

One such promoter/operator system is the so-called "tac" or trp-lac promoter/operator system (Russell and Bennett, (1982), Gene, vol. 20, pp.231–243, which disclosure is hereby incorporated by reference). This hybrid promoter is constructed by combining the −35 b.p. (−35 region) of the trp promoter and the −10 b.p. (−10 region or Pribnow box) of the lac promoter (the sequences of DNA which are the RNA polymerase binding site). In addition to maintaining the strong promoter characteristics of the tryptophan promoter, tac is also controlled by the lac repressor.

When cloning in a eucaryotic host cell, enhancer sequences (e.g., the 72 bp tandem repeat of SV40 DNA or the retroviral long terminal repeats of LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have the remarkable abilitv to function upstream from, within, or downstream from eucaryotic genes. Therefore, the position of the enhancer sequence with respect to the inserted gene is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in E. coli requires a Shine-Dalgarno ("SD") sequence about 7–9 bases 5' to the initiation codon (ATG) to provide a ribosome binding site. Thus, any SD-ATG combination that can be utilized by host cell ribosomes can be employed. Such combinations include but are not limited to the SD-ATG combination from the CRO gene or the N gene of coliphage lambda, or from the E. coli tryptophan E, D, C, B or A genes. Additionally, any SD-ATG combination produced by recombinant DNA or other techniques involving incorporation of synthetic nucleotides can be used.

Any of the conventional cloning methods for insertion of DNA fragments into a vector can be used to ligate the promoter and other control elements into specific sites within the vector. Accordingly, gene sequences containing those regions coding for the calcium channel Cl subunit of the invention can be ligated into an expression vector at a specific site in relation to the vector promoter and control elements so that when the recombinant DNA molecule is introduced into a host cell the foreign genetic sequence can be expressed (i.e., transcribed and translated) by the host cell.

As previously mentioned, the recombinant DNA molecule can be introduced into appropriate host cells (including but not limited to bacteria, virus, yeast, vertebrate and invertebrate cells or the like) by transformation, infection or transfection (depending upon the vector/host cell system) . Transformants are selected based upon the expression of one or more appropriate gene markers normally present in the vector, such as ampicillin resistance or tetracycline resistance in pBR322, or thymidine kinase activity in eucaryotic host systems. Expression of such marker genes should indicate that the recombinant DNA molecule is intact and is replicating. Expression vectors may be derived from cloning vectors, which usually contain a marker function. Such cloning vectors may include, but are not limited to the following: SV40 and adenovirus, vaccinia virus vectors, neuronal invertebrate viruses such as baculoviruses, yeast vectors, bacteriophage vectors such as lambda gt-WES-lambda BC, lambda gt-l-lambda B, M13mp7, M13mp8, M13mp9, or plasmid DNA vectors such as pBR322, pAC105, pVA51, pACYC177, pKH47, pACYC184, pUB110, pMB9, pBR325, Col El, pSC101, pBR313, pML21, RSF2124, pCR1, RP4, pBR328 and the like.

The expression vectors containing the foreign gene inserts (i.e., DNA encoding the calcium channel $\alpha_1$ subunit of the invention) can be identified by three approaches: (1) DNA—DNA hybridization using probes comprising sequences that are homologous to the gene(s) ; (2) presence or absence of "marker" gene function and (3) expression of inserted sequences based on physical, immunological or functional properties. Once a recombinant which expresses the gene is identified, the gene product should be analyzed. Immunological analysis is especially important because the ultimate goal is to use the gene(s) or recombinant expression systems that express the gene(s) in assays for screening chemical agents. Once the calcium channel al subunit is identified, it is cultured under conditions which facilitate growth of the cells and expression of the gene as will he at-parent to one skilled in the art, then isolated and purified by standard methods including chromatography (e.g., ion exchange, affinity, and sizing column chromatography) , centrifugation, differential solubility, or by any other standard techniques. In addition, since the amino acid sequence is known from the DNA sequence of the invention, the calcium channel (XI subunit can be synthesized by chemical methods according to the procedure of Hunkapiller et al., (1984), Nature, vol. 310, pp. 105–111, which disclosure is hereby incorporated by reference.

The functional calcium channel receptor produced by expression of the calcium channel $\alpha_1$ subunit gene above of the invention, can be used to screen for pesticides that are effective in the control of invertebrates. It is known that the invertebrate calcium channel receptor forms a particularly attractive site for pesticides due to pronounced differences in its pharmacology with that of vertebrates, as described in Glossman, *British Journ. of Pharmacology*, Vol 202, pp 446–456 (1991), which disclosure is hereby incorporated by reference. Due to those differences in neuronal invertebrate and vertebrate calcium channel receptor pharmacology, cells transformed to include the neuronal invertebrate calcium channel receptor formed in accordance with the present invention can be exposed to various potential insecticides and pesticides and evaluated for their susceptibility to the agents to develop and identify invertebrate control agents that will not cause adverse effects to vertebrate species. Exemplary methods of screening are described in Eldefrawi et al., (1987), *FASEB J., vol.* 1, pp. 262–271; and Rauh et al., (1990), *Trends in Pharmacol. Sci., vol.* 11, pp. 325–329, which disclosures are hereby incorporated by reference.}

The following Examples are provided to further illustrate the present invention.

EXAMPLE I

Figure 3:
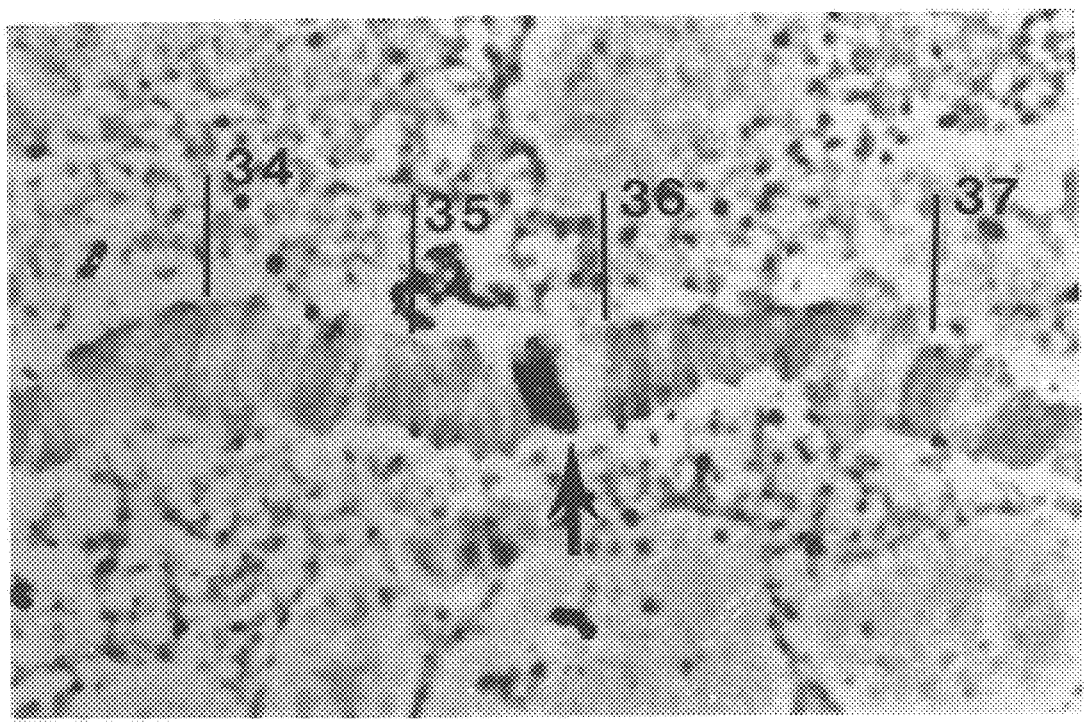
FIG. 3 is a photomicrograph of the chromosome mapping of the $\alpha_1$ subunit Dmca1D [In situ hybridization to *Drosophila* salivary gland polytene chromosomes using a biotinylated probe (bases 4252–5795, FIG. 2) mapped this gene to 35EF on the left arm of chromosome 2. Numbered divisions for this section of chromosome 2L are marked and the hybridization signal is indicated by the arrow].

Methods
1. Polymerase Chain Reaction ("PCR"):

Primer sites were selected by aligning cDNA sequences for $\alpha_1$ subunits of calcium channels from rabbit skeletal muscle (Tanabe et al., (1987), *Nature, vol.* 328, pp. 313–318, which disclosure is hereby incorporated by reference), heart (Mikami et al., (1989), Nature, vol. 340, pp. 230–233, which disclosure is hereby incorporated by reference) and brain (Mori et al., (1991), *Nature, vol.* 350, pp. 398–402, which disclosure is hereby incorporated by reference), rat aorta (Koch et al., (1990), *J. Biol. Chem., vol.* 265, pp. 17786–17791, which disclosure is hereby incorporated by reference), and fish skeletal muscle (Grabner et al., (1991), *Proc. Natl. Acad. Sci. USA, vol.* 88, pp. 727–731, which disclosure is hereby incorporated by reference) to identify the most highly conserved regions with the least amount of codon degeneracy. Inosine was used when A, T, G, and C were all a possibility at a given site (Martin et al., (1985), *Nucleic Acids Res., vol.* 13, p. 8927 and Knoth et al., (1988), *Nucleic Acids Res., vol.* 16, p. 11932, which disclosures are hereby incorporated by reference). FIGS. 1 and 3 show the positions of a successful primer pair (P6 and P7) in the carboxy portion of the channel. Primer P6 lies within IVS5 and has the sequence: 5'AT[C/T/A]G[T/C]IATG[C/T]TITT [C/T]TT[CT]ATITA[C/T]GC3'("SEQ. ID. NO. 5") Primer P7 lies between IVS6 and the putative EF hand and has the sequence: 5'TC[G/A]TCIA[G/A][G/A]TG[G/A] TGIGGICCIA[G/A] [G/A/T]AT3'("SEQ. ID. NO. 6"). FIG. 1 additionally shows that there are 4 repeat units designated I, II, III, and IV which are similar in structure to each other. Within each repeat there are six transmembrane domains designated 1 through 6 (aka S1–S6) which are thought to form α-helical structures through the membrane. The S4 regions have positively charged amino acids every 3 to 4 residues which are thought to align on one side of the α-helix to form the voltage sensor. In addition to the membrane spanning domains, the extracellular region which falls between regions S5 and S6 in each repeat is thought to dip into the membrane forming short segments SS1 and SS2 involved in the ion selectivity filter of the channel. Furthermore, the cDNA clones shown in FIG. 1 were isolated from a head library using as a probe the 499 base pair PCR amplification product from primers shown in A (SH22C) or the 5' ends of clones SH22C or W8A. The diagram shows the overlap among the clones. FIG. 3 further shows that in situ hybridization to *Drosophila* salivary gland polytene chromosomes using a biotinylated probe (bases 4252–5795, FIG. 2) mapped this gene to 35EF on the left arm of chromosome 2. This same position was seen using a variety of other probes from W8A and SH22C (data not shown) suggesting that these overlapping cDNAs (FIG. 1) are encoded by the same gene.

2. Reaction Conditions For Cross Species Amplifications:

The template for the polymerase chain reaction was 150 ng of *Drosophila* genomic DNA prepared from adult flies as described by Jowett, T., (1986), In: *Drosophila: A Practical Approach,* Roberts, D. B. (ed.), IRL Press (Oxford), which disclosure is hereby incorporated by reference. The 50 $\mu$L reaction mixture contained: 0.2 mM of each of the dNTPs, 10 mM Tris (hydroxymethyl) aminomethane (Tris) buffer pH 8.3, 50 mM KCl, 1.5 mM $MgCl_2$, 0.001% gelatin, 0.1 $\mu$M of each primer, and 1.25 units AmpliTaq™ DNA polymerase from Perkin Elmer Cetus (Norwalk, Conn.). Following an initial 2 minutes at 95° C., the following cycle was repeated 35 times: denaturation 2 minutes at 95° C., annealing 2 minutes at 40° C, extension 2 minutes at 72° C. The final extension was 10 minutes at 72° C. PCR products were analyzed by electrophoresis of 10 $\mu$L of reaction mix on a 1% agarose gel.

3. DNA Sequencing:

The band containing the PCR product of interest was extracted from the gel by the phenol/freezing method of Benson, S. A., (1984), *Biotechniques, vol.* 2, pp. 66–68, which disclosure is hereby incorporated by reference), resuspended in Tris EDTA buffer, ph 8.0 (TE buffer, ph 8.0) (Sambrook et al., (1989), In: *Molecular Cloninc: A Laboratory Manual,* 2nd ed., Cold Spring Harbor Laboratory Press, Cold Spring Harbor, N.Y., which disclosure is hereby incorporated by reference) to a concentration of 10–20 ng/$\mu$L and 25 ng template was used for reamplification in 100 $\mu$L reactions prior to sequencing. The PCR conditions were as described above, except that the annealing temperature was 65° C. Sequencing templates were purified and concentrated using Centricon-100 columns (Amicon, Danvers, Mass.). Double-stranded DNA sequencing was performed on an Applied Biosystems Sequencer Model 373A using the dideoxy chain termination method with fluorescent dye-tagged M13 or SP6 primers according to instructions supplied with a Taq Dye Primer Cycle Sequencing kit (Applied Biosystems, Inc., Foster City, Calif.). Using this approach 300–400 bases were generally read from each template. Each segment of DNA was sequenced at least twice in each direction. For sequencing PCR products without subcloning or for sequencing phage clones, new tailed primers were synthesized adding an 18 nucleotide M13 or SP6 sequence to the 5' end of the original PCR primer sequence.

Figure 1B:
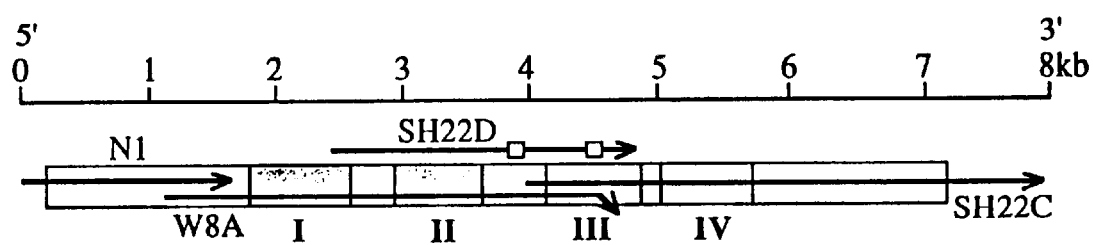

4. Screening For cDNA Clones:

A total of $2 \times 10^5$ plaque-forming units (pfu) of a *Drosophila* head cDNA library in λgt11 (Itoh et al., (1986), *Proc. Natl. Acad. Sci. USA, vol.* 83, pp. 4081–4085, which disclosure is hereby incorporated by reference, generously provided by Dr. Paul Salvaterra, Beckman Research Institute, Duarte, Calif.) were screened on Nylon membranes (ICN, Costa Mesa, Calif. using the 499 base pair amplification product from primer pair P6/P7. The probe was random-prime labeled with $^{32}$P-dCTP using the Multiprime Kit (Amersham Corp., Arlington Heights, Ill.). Standard conditions were used for prehybridization, hybridization, and washing (Sambrook et al., (1989), cited elsewhere herein, which disclosure is hereby incorporated by reference). A 4 kb cDNA clone (SH22C) was isolated initially and further clones (including W8A and SH22D) were obtained using the 5' end of SH22C. Since W8A did not contain the 5' end of the open reading frame, rapid amplification of cDNA ends was done with the 5' rapid amplification of cDNA ends (RACE) kit from Clontech (Palo Alto, Calif.) and a primer from the 5' end of W8A and extended the sequence 360 bases upstream. Since this extension was still incomplete, the 5' end of W8A was also used to isolate the N1 cDNA clone (FIG. 1B).

5. In situ Hybridization To Salivary Gland Chromosome Squashes:

The map position of cloned cDNAs was determined as described by Engels et al., (1985), *Focus, vol.* 8J pp. 6–8 and Murtagh et al., (1993), *Biochemistry, vol.* 32, pp. 6011–6018, which disclosures are hereby incorporated by reference, using biotinylated probes hybridized to salivary gland chromosomes.

6. Northern Blots:

Heads, bodies and legs were isolated from frozen adult flies as described by Schmidt-Nielsen et al. (1977), *J. Neurochem., vol.* 29, pp. 1013–1029, which disclosure is hereby incorporated by reference. Total RNA was prepared and poly(A)+MrRNA isolated by the guanidinium isothiocyanate-CsCl gradient method followed by one passage over oligo (dT)-cellulose columns (Sambrook et al., (1989), cited elsewhere herein, which disclosure is hereby incorporated by reference). 10 μg of poly(A)+RNA in TE was added to each lane of 0.8% agarose gel containing 6.3% formaldehyde and electrophoresed for 3 hours at 100V using 1×MOPS buffer [(3-[N-Morpholino]propanesulfonic acid)] according to Sambrook et al. (1989), cited elsewhere herein, which disclosure is hereby incorporated by reference. The gel was capillary blotted onto a nylon membrane (Schleicher & Schuell, Keene, N.H.) and fixed by UV crosslinking. Prehybridization was for 6 hours at 42° C. in 50% deionized formamide, 5×SSPE, 5×Denhardt's, 0.5% sodium dodecyl sulfate (SDS), 100 μg/ml denatured salmon sperm DNA and then $10^6$ cpm/ml $^{32}$P-labeled cDNA probe was added and the incubation continued for 16 hr at 42° C. The blot was washed 2 times for 15 minutes each at room temperature in 2×SSC, 0.1% SDS followed by 2 more washes for 30 minutes each at 65° C. in 0.1×SSC, 0.1% SDS. The blots were exposed to X-ray film at −70° C. Standard solutions (SSC, SSPE, Denhardt's) are as described by Sambrook et al. (1989), cited elsewhere herein, which disclosure is hereby incorporated by reference.

7. Reverse Transcri-tase-Couiled PCR ("RT-PCR"):

First strand cDNA synthesis in 50 μL was conducted at 42° C. for 60 minutes using 1200 units/ml AMV (avian myeloblastosis virus) reverse transcriptase and 80 μg/ml poly(A)+MRNA as described by Gubler, U. and Hoffman, B J., (1983), *Gene, vol.* 25, pp. 263–269, which disclosure is hereby incorporated by reference, with the following changes: 40 μg/ml oligo dT primer, 50 μM KCl, 0.5 mM spermidine, 1 mM each DNTP, 800 units/ml RNasin. The reaction was stopped with 1 mM EDTA (ethylenediaminetetraacetic acid) and 0.5 μL of the reaction mix was used for a 50 μL PCR as described for the cross species amplifications above except that 0.005% gelatin was used and the amplification was 35 cycles of: 95° C. 1 minute, 60° C. 1 minute, 72° C. 1 minute, followed by a final 5 minute extension at 72° C. Forty μL of the amplification reaction was electrophoresed and extracted from an agarose gel by the freezing phenol method as described above. DNA pellets were resuspended in 20 μL distilled water and 6 μL was used for each restriction enzyme digestion described in Table 1.

8. In situ Hybridization To Embrvo Whole Mounts:

Whole mount in situ hybridization to *Drosophila* embryos was done as described by Tautz and Pfeifle, (1989), cited elsewhere herein, which disclosure is hereby incorporated by reference, using the formaldehyde fixation method. A single-stranded digoxigenin-labeled cDNA probe was prepared from a PCR product (bases 6488–6777 of the coding region, FIG. 2) which had been extracted from the gel using an Ultrafree-MC filter unit from Millipore Corp. (Bedford, Mass.), and concentrated using a Centricon-30 spin column. This purified PCR product (200 ng) was used as template to prepare single-stranded antisense DNA in a total volume of 25 μL using 5 μL of the nucleotide solution from vial 6 in the Genius Kit from Boehringer Mannheim (Indianapolis, Ind.), 2 μL primer stock for the antisense strand (10 μM), and 0.3 μL Taq polymerase (5U/μL). Amplification conditions for the synthesis of this single-stranded probe were: 94° C. 45 seconds, 55.C. 30 seconds, and 72° C. for 60 seconds, for a total of 25 cycles. Labeled probe was stored at −20° C.

EXAMPLE II

Strategy For Cloning An $\alpha_1$ Subunit

Of Drosorhila Calcium Channels

When these studies were conducted, it was evident that *Drosophila* had multiple calcium channel subtypes, at least some of which had a different pharmacological specificity from that reported for the cloned dihydropyridine receptor from vertebrate skeletal muscle (Pauron et al., (1987), *Biochemistry, vol.* 26, pp. 6311–6315; Greenberg et al., (1989), *Insect Biochem., vol.* 19, pp. 309–322; Pelzer et al., (1989), *EMBO J., vol.* 8, pp. 2365–2371; Glossmann et al., (1991), *Br. J. Pharmacol., vol.* 102, pp. 446–452, which disclosures are hereby incorporated by reference). It was not clear, however, how much structural conservation would exist between *Drosophila* calcium channel subunits and those which had been cloned from vertebrates (Tanabe et al., (1987), *Nature, vol.* 328, pp. 313–318; Mikami et al., (1989), *Nature, vol.* 340, pp. 230–233; Koch et al., (1990), *J. Biol. Chem., vol.* 265, pp. 17786–17791; Mori et al., (1991), *Nature, vol.* 350, pp. 398–402; and Grabner et al., (1991), *Proc. Nati. Acad. Sci. USA, vol.* 88, pp. 727–731, which disclosures are hereby incorporated by reference). Since both the *Drosophila* head binding activity and the cloned vertebrate subunits were known to be phenylalkylamine sensitive, it was reasoned that at least some regions of the sequence were likely to be conserved. Using a polymerase chain reaction ("PCR") based strategy allowed focus on short regions for primer design which were most likely to be conserved across species. *Drosophila* genomic DNA was used as a template to avoid assumptions concerning the tissue and stage in development when calcium channels would be expressed. Products approximately the same size as (or larger than) that predicted from vertebrate $\alpha_1$ subunits were sequenced to identify those which encoded deduced amino acid sequences with structural similarity to the corresponding region of vertebrate calcium channel $\alpha_1$ subunits. By including products larger than predicted from the vertebrate sequences, it allowed for the occurrence of introns in the genomic DNA used as template.

The product from primer pair P6/P7, spanning the region from IVS5 to a cytoplasmic region following IVS6 (FIG. 1A), had a deduced amino acid sequence very similar to that of vertebrate $\alpha_1$ subunits except that the 3' end of the IVS5 coding region and the middle of the IVS6 coding region were disrupted by 59 and 60 base pair introns, respectively.

These introns were readily recognized using codon preference analysis from the University of Wisconsin Genetics Computer Group (GCG) software package.

Northern analysis showed that this *Drosophila* genomic fragment recognized a message that was expressed at a relatively high level in heads as would be expected for a neuronal calcium channel component (Greenberg et al., (1989), *Insect Biochem.*, vol. 19, pp. 309–322, which disclosure is hereby incorporated by reference), so an adult head cDNA library was screened. The two longest cDNA clones, W8A and SH22C, with an overlap of 572 nucleotides were sequenced and combined as shown schematically in FIG. 1B. Although the sequence match between the two clones is excellent within the region of overlap (only 3 nucleotide discrepancies, indicated by open triangles in FIG. 2), there is a region of 149 nucleotides in W8A which shows no sequence similarity with SH22C. This nonmatch region begins in the intracellular loop between IIIS4 and S5 and extends into transmembrane domain IIS5. In situ hybridization to salivary gland chromosomes (FIG. 3) showed that both W8A and SH22C mapped to the same position at 35EF on the left arm of the second chromosome suggesting that the two cDNA clones are derived from the same gene. This was confirmed by sequencing a genomic clone and the SH22D cDNA clone in the regions flanking the non-overlap section. Sequence analysis revealed two alternatively spliced exons in this region.

The 5' end sequence of the cDNA was derived from the N1 clone. In addition, 5' RACE (rapid amplification of cDNA ends) was done starting with pole (A)+mRNA from Canton-S and a primer from the 5' end of W8A. The RACE product extended only 360 bases upstream from the end of W8A whereas N1 clone provided 1116 bases upstream of the 5' end of W8A. In the 360 bases of overlap between the RACE product and clone N1, there was an exact match except for three bases (indicated by the closed triangles in FIG. 2) within the proposed open reading frame. These differences did not affect the amino acid sequence and most likely represent sequence polymorphisms between DNA from different wild-type sources.

EXAMPLE III

Structural Features Of The CDNA Sequence

The complete nucleotide sequence and the deduced amino acid sequence for the *Drosophila* $\alpha_1$ subunit are shown in FIG. 2 (SEQ. ID. NO. 1 and SEQ. ID. NO. 2, respectively). Bases are numbered from the first of five possible AUG initiation codons all of which are marked with a *. Three nucleotides which differ in sequence between the N1 clone and the 5' RACE product using Canton-S poly (A)+ MRNA are indicated with a closed triangle above the nucleotide. The sequence shown is from the Nl clone. The 3 nucleotides which differ between cDNA clones W8A and SH222C are indicated with an open triangle above each. The sequence shown is that found in W8A because those nucleotides have also been found in the corresponding genomic DNA sequence (D. Ren and L.M. Hall, unpublished). The deduced amino acid sequence is shown below the DNA sequence and the proposed transmembrane domains are indicated as labeled lines underneath the corresponding amino acid sequences. The position of a proposed calcium binding domain (the EF hand, Babitch, J., (1989), Nature, vol. 346, pp. 321–322, which disclosure is hereby incorporated by reference) is indicated by the heavy labeled line under the amino acids involved. The in-frame stop codons preceding and following the open reading frame are indicated with a dark dot underneath the first base in each codon. The positions of the primers used in the initial PCR amplification of genomic DNA are indicated by the boxed gray areas of the nucleic acid sequence with labels P6 and P7 directly above them. This sequence was submitted to GenBank and received Accession No. U00690.

The carboxy terminus of the deduced protein is unambiguously determined by the TAG stop codon at nucleotide position 7549–7551 which is followed by 10 additional in-frame stop codons (indicated by a black dot below the first nucleotide in each triplet). There is no polyadenylation consensus sequence (AAUAAA) in the 3' untranslated region, so there may be some additional 3' sequence which was not included in the SH22C clone. The total assembled cDNA sequence (~8 kb) is about 1.5 kb shorter than the smallest message observed in Northern blotting experiments (FIG. 4). This may be due to missing 5' and/or 3' untranslated regions in the cDNA clones sequenced and/or to extensive polyadenylation.

With reference to FIG. 4, there is shown the Northern blot of poly(A)+ MRNA (10 µg/lane) isolated from bodies (B), heads (H), or legs (L) was probed with a PCR fragment (bases 6141–7511, FIG. 2) from clone SH22C and washed at high stringency. The tics on the right of the figure indicate positions of bands. The lower inset shows the results of reprobing with ribosomal protein 49 cDNA (rp49) to control for mRNA recovery and gel loading differences since rp49 is expressed uniformly throughout the organism and throughout the different developmental stages (see B below) (O'Connell, P. O. and Rosbash, M., (1984), *Nucleic Acids Res.*, vol. 12, pp. 5495–5513, which disclosure is hereby incorporated by reference). A Northern blot (as in part A) consisting of mRNA isolated from embryos of different ages was hybridized with a $^{32}$P-labeled double-stranded probe from W8A (nucleotides 961 to 2214, FIG. 2).

The most likely start translation start site is in the first methionine marked with a * since it is preceded by 3 in-frame stop codons within the 156 bases upstream as shown in FIG. 2. However, there are 4 additional methionines (also marked with a * underneath the M symbol in FIG. 2) encoded in the region between the first methionine and IS1. The area immediately upstream of each of these methionine codons was compared with the *Drosophila* translation start site consensus sequence (C/AAAA/C AUG) (Cavener, D. R., (1987), *Nucleic Acids Res.*, vol. 15, pp. 1353–1361, which disclosure is hereby incorporated by reference). The first methionine shows 0/4 matches. Although it lacks an A at the crucial −3 position, it has the second most commonly used base (G) at this position. The second, third and fifth methionines all have an A in the −3 position. In addition, the second (M494) and fifth (M553) methionines show 3 out of 4 nucleotide matches to the upstream consensus sequence for *Drosophila*. In *Drosophila*, the average fit to the 4 nucleotide consensus positions immediately upstream of a start codon is 3.1 matches. On the basis of nucleotide sequence, met494 and met553 could be start site candidates, however there are no upstream in-frame stop codons preceding them. Therefore, it is believed that met1 is the start site.

EXAMPLE IV

Tissue Distribution And Heterogeneity

Of Dmca1D Message Expression

Figure 4A:
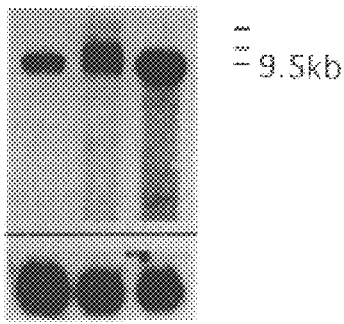
FIG. 4 illustrates the tissue and temporal expression of the *Drosophila* $\alpha_1$ subunit mRNA by Northern blotting [A, Message distribution in adult body parts. B, developmental profile of calcium channel $\alpha_1$ subunit MRNA expression in embryos showing a peak of expression in the late embryonic stages. Lanes 1–7 represent sequentially older embryos collected over 3 hour intervals and then aged approximately at 25° C. (1=0–3 hr, 2=3–6 hr, 3=6–9 hr, 4=9–12 hr, 5=12–15 hr, 6=15–18 hr, 7=18–24 hr)].
Figure 4B:
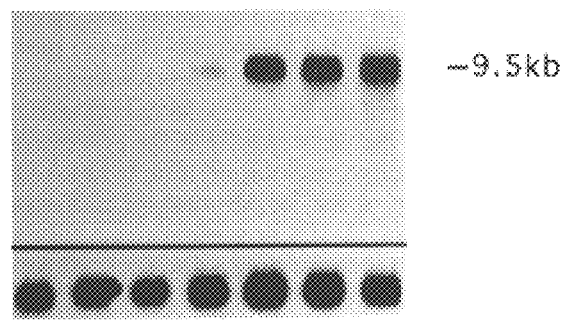

The relative expression of Dmca1D transcripts in different body parts was determined by Northern blot analysis using rp49 (a uniformly expressed ribosomal protein mRNA) (O° Connell, P. 0. and Rosbash, M., (1984), *Nucleic Acids Res.,* vol. 12, pp. 5495–5513, which disclosure is hereby incorporated by reference) as a control for amount of RNA loaded into each lane. As shown in FIG. 4A, poly(A)+RNA from bodies (B), heads (H), and legs (L) were compared following hybridization with a probe from the 3'end of clone SH22C. This probe contains the coding sequence for the nonconserved carboxy terminus of the $\alpha_1$ subunit. All three preparations show a major band at 9.5 kb and a minor band at 12.5 kb. The minor band is seen most clearly in the head preparation. In addition, the head preparation shows a second major band at 10.2 kb. A similar result (data not shown) was obtained using a probe derived from W8A. The relationship among the three MRNA size classes is not known. The largest size class (12.5 kb) is a very weak signal in all lanes suggesting that it might be an unprocessed transcript or the product of another gene picked up by sequence similarity. Compared to messages expressed in heads, there is less heterogeneity in the message expressed in the bodies and legs since only one major band (9.5 kb) is visible.

Figure 5:
FIG. 5. is a photomicrograph of the localization of $\alpha_1$ subunit mRNA in the embryonic nervous system using in situ hybridization to a whole mount embryo [Dorsal is up and anterior is to the left].

To further investigate the difference in message heterogeneity among heads, bodies and legs, two regions where sequence data from 3 different cDNA clones (W8A, SH22C, and SH22D; see FIG. 1) had shown differences were reviewed. The positions of the regions studied are shown as open boxes in the SH22D clone in FIG. 1B. These differences could be most easily distinguished by RT-PCR (reverse transcriptase coupled PCR) amplification followed by a diagnostic restriction enzyme digestion. It should be noted that the differences in the actual nucleic acid sequences were extensive as expected for alternative splice products and could not be explained by single base changes due to sequence polymorphisms (D. Ren and L.M. Hall, unpublished). As shown in Table 1, in each of the two regions tested for alternative splicing, two different forms were found in heads but only a single form was found in bodies or legs. Embryos (which express this subunit only in the nervous system as shown in FIG. 5 and discussed below) show the same pattern of heterogeneity seen in heads. Taken together, these results again suggest there may be more functional heterogeneity in Dmca1D type calcium channels in neuronal tissue than elsewhere in the fly.

EXAMPLE V

Temporal Pattern Of Expression Of Dmca1D

To determine when the Dmca1D message is expressed in *Drosophila* embryos, a Northern blot (FIG. 4B) containing poly(A)$^+$ mRNA from a variety of embryonic stages was probed with two different Dmca1D specific probes: one from W8A (shown in FIG. 4B) and one from SH22C (from nucleotide 5665 in IVS6 to the end, data not shown). Regardless of which probe was used, expression of the 9.5 kb calcium channel message is detected faintly in embryos at 9 to 12 hours corresponding to the time when condensation of the 20 nervous system begins (Kankel et al., (1980), In: *The Genetics and Biology of Drosophila,* vol. 2, Ashburner, M. and Wright, T. R. F., eds., Academic Press (New York), which disclosure is hereby incorporated by reference). Expression increases rapidly as the nervous system matures within the embryo, peaking just prior to hatching. A second peak of expression of the 9.5 kb message is observed in late pupal stages around 73 to 108 hours post puparium formation when the nervous system is completing a dramatic reorganization (F. Hannan, unpublished observations, which disclosure is hereby incorporated by reference).

EXAMPLE VI

Embryonic Whole Mount in situ Hybridization

To determine where the message for this $\alpha_1$ subunit is expressed, a digoxigenin-labeled antisense probe was used on embryonic whole mounts. As shown in the 13–15 hour embryo in FIG. 5, the Dmca1D subunit was preferentially expressed in the nervous system. A single-stranded, antisense DNA probe labeled with digoxigenin was hybridized to embryo whole mounts and the signal detected as described by Tautz, D. and Pfeifle, C., (1989), *Chromosoma,* vol. 98, pp. 81–85, which disclosure is hereby incorporated by reference. The dark staining pattern highlights the round, dorsal cerebral hemisphere and the ventral ganglion which comes off the ventral side of the sphere and curves posteriorly on the ventral surface of the embryo.

EXAMPLE VII

General Structural Features Of

The Deduced Amino Acid Secuence

Figure 6A:
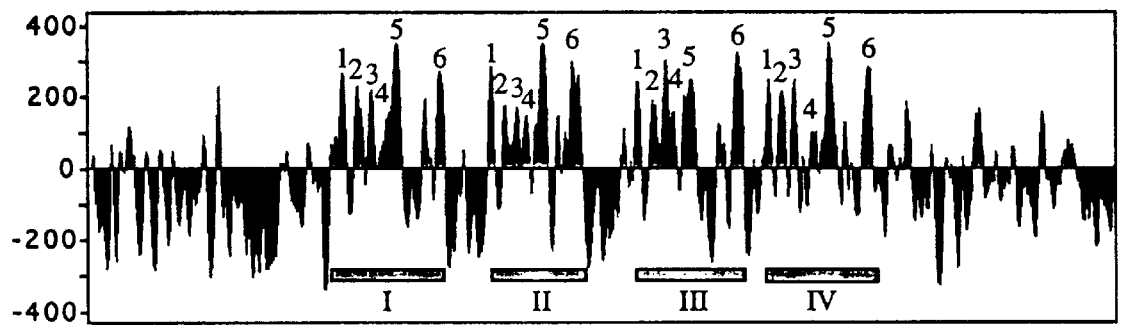
FIG. 6. is a comparison of hydropathy plots for $\alpha_1$ subunits from rat brain type D [Panel B, with the *Drosophila* subunit; Panel A, using the first in-frame methionine (met1) as the initiating amino acid in the *Drosophila* sequence. Up is hydrophobic and down (negative numbers) is hydrophilic].
Figure 6B:
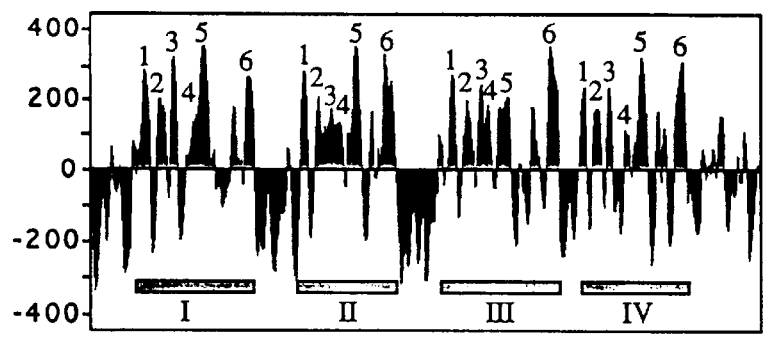

Using the first in-frame AUG (metl) following a series of in-frame stop codons as the translation start site, FIG. 2 shows that the open reading frame of the combined cDNA clones would encode a protein of 2516 amino acids with an expected molecular weight of 276,493 and a predicted pI of 5.04. The hydrophobicity plot of this complete deduced protein is shown in FIG. 6A where it is compared with the calcium channel type D $\alpha_1$ subunit from rat brain (FIG. 6B). Hydropathy plots were determined using the method of Kyte, J. and Doolittle, R. F., (1982), *J. Mol. Biol.,* vol. 157, pp. 105–132, which disclosure is hereby incorporated by reference, with the GeneWorks software. If the second AUG is the actual translation start site, the *Drosophila* protein would consist of 2023 amino acids and have a predicted molecular weight of 224,369 and a pI of 6.49. If it begins with the fifth AUG, the protein would consist of 1964 amino acids with a predicted molecular weight of 218,580 and a predicted pI of 6.78. Just as in the vertebrate calcium channel $\alpha_1$ subunits, the *Drosophila* subunit shows four repeat domains (indicated by the bars in FIG. 6 labeled I through IV). Each of these repeats shows 6 hydrophobic domains (labeled 1 through 6) which would be long enough to span the membrane. The resemblance to the vertebrate $\alpha_1$ hydropathy plots is striking in the hydrophilic as well as the hydrophobic domains. The only places where there are differences are in the cytoplasmic amino and carboxy terminal tails. Both regions are much longer in *Drosophila* than in the vertebrate homologues. Although there is striking similarity in the region of the carboxy tail closest to transmembrane region IVS6, the similarity falls off after about 163 amino acids from the end of the IVS6 region when the *Drosophila* sequence is compared with the rat brain D sequence or after 199 amino acids when compared with the rabbit skeletal muscle sequence (comparison not shown). On the amino terminal end the similarity to the vertebrate homologues falls off after about 40 to 50 amino acids upstream of the beginning of IS1.

The repeat structure and the pattern of the hydrophobic domains puts this newly cloned *Drosophila* protein in the same superfamily as the voltage-gated sodium and calcium channels. As shown in Table 2, when the deduced protein is compared with available sequences for sodium and calcium channels, in general there is more similarity in amino acid sequence between the *Drosophila* clone and vertebrate calcium channels (ranging from 63.4 to 78.3%) than between this sequence and sodium channels (57.9 to 58.9%) even if the sodium channel is from *Drosophila*. These differences are even more striking if amino acid identity is considered (42.7 to 64.2% identity for calcium channels versus 29.6 to 30.5% for sodium channels). Thus, based on overall sequence similarity, the newly cloned gene would be designated as a member of the calcium channel gene family.

Within the calcium channel group, the *Drosophila* sequence shows the closest relationship to rat brain type D. The next highest scoring channel from rabbit skeletal muscle shows 8% less identity and 6% less similarity than the rat brain type D channel. Based on this sequence similarity hierarchy and on its expression in the nervous system, the *Drosophila* channel was designated as *Drosophila melanogaster* calcium channel alpha 1 subunit type D ("Dmca1D").

As for ot her members of the voltage-sensitive cation channel family, each of the S4 transmembrane domains of the newly cloned channel subunit shows positively charged amino acids (R=arginine or K=lysine) every third or fourth amino acid. In a commonly proposed model, this pattern would put all of the positively charged side chains on the same side of an alpha helix so that they sit in the membrane as the voltage-sensor (Stühmer et al., (1989), *Nature, vol.* 339, pp. 597–603, wh ich disclosure is hereby incorporated by reference). As summarized in Table 3, the *Drosophila* protein shows the same general pattern as the majoritf of other calcium channels with 5 positively charged side chains in the S4 helices in domains I, II, and IV and 6 in domain III. Oniy the rat brain A and B and rabbit brain-1 channels deviate from this pattern.

EXAMPLE VIII

Proposed Calcium Binding EF Hand Region

Another feature commonly found in both sodium and calcium channel $\alpha_1$ subunits is a protein motif known as the EF hand, which consists of two $\alpha$-helices flanking a calcium binding loop (Babitch, J., (1990), *Nature, vol.* 346, pp. 321–322, which disclosure is hereby incorporated by reference). As indicated by the heavy underlined region beginning 20 amino acids downstream from the IVS6 region in FIG. 2, an EF hand is found in the *Drosophila* sequence. As shown in Table 4,(SEQ ID NOS: 10–23) in the Tufta-Kretsinger test (Tufty, R. M. and Kretsinger, R. H., (1975), *Science, vol.* 187, pp. 167–169, which disclosure is hereby incorporated by reference) the Dmca1D sequence has 11 matches (out of 16 possibilities) for residues important for calcium binding. The number of matches for Dmca1D can be increased to 14 by allowing conservative amino acid substitutions. Many vertebrate calcium channel $\alpha_1$ subunits show a similar pattern of matching (Babitch, J., (1990), *Nature, vol.* 346, pp. 321–322, which disclosure is hereby incorporated by reference). Again, the *Drosophila* sequence shows more similarity to calcium channels than to sodium channels in this critical area.

EXAMPLE IX

Ion Selectivity Filter

A portion of the sodium channel involved in the ion selectivity filter has been identified within short segment 2 (SS2) lying between S5 and S6 in all repeats (Heinemann et al., (1992), *Nature, vol.* 356, pp. 441–443, which disclosure is hereby incorporated by reference) . By changing a single amino acid residue (K1422 in repeat III or A1714 in repeat IV of rat sodium channel II) to a negatively charged glutamic acid (E) (as is found in calcium channels) , the ion selectivity of the channel can be changed from that of a sodium channel to resemble that of a calcium channel. Recently, Tang et al., (1993), *J. Biol. Chem., vol.* 268, pp. 13026–13029, which disclosure is hereby incorporated by reference, have done the reciprocal experiment on cardiac calcium channels and have shown that modification of conserved glutamate residues in the SS2 region of repeats I, II, or IV alters the ion selectivity and permeability of calcium channels. Table 5(SEQ ID NOS: 24–57) compares the SS2 sequences of the newly cloned Dmca1D cDNA with those of other sodium and calcium channels. In general, the new *Drosophila* sequence resembles the calcium channel sequences more closely than it does the sodium channel sequences. In the crucial region of repeats I, II, III and IV all of the negatively charged glutamic acids (bold E) found in calcium channels have been conserved in the *Drosophila* sequence, providing further evidence that Dmca1D encodes a calcium channel subunit. The conservation of glutamate residues in all four SS2 regions is consistent with the suggestion of Tang et al. (1993), cited above, which disclosure is hereby incorporated by reference, that these residues form a ring in the pore-lining SS1-SS2 region involved in ion selectivity and permeability.

EXAMPLE X

Possible Sites For Posttranslational

Modification Of The Protein Encoded Bv Dmca1D

There are 2 partially overlapping, possible N-linked glycosylation sites (NX[S/T]X) (N644 and N647) (SEQ ID NO: 2) in the *Drosophila* $\alpha_1$ subunit located in a region of the protein predicted to be external to the plasma membrane. (X generally is any amino acid, but in this site only X refers to any amino acid except P.) These asparagines fall in the loop between IS1 and IS2 which is predicted to be extracellular (see FIGS. 1 and 2). There are 8 possible cAMP-dependent protein kinase phosphorylation sites ([R/K]XX[S/T](SEQ ID NO: 8)) lying in predicted cytoplasmic domains. Six are in the amino terminal region; one is in the region between IIS6 and IIIS1, which, in skeletal muscle L-type channels, has been implicated in excitation-contraction coupling processes (Tanabe et al., (1990), *Nature, vol.* 346, pp. 567–569, which disclosure is hereby incorporated by reference); one is in the carboxy terminus in the cytoplasmic region corresponding to the calcium-binding EF hand. In addition, there are 21 possible protein kinase C phosphorylation sites ([S/T]X[R/K]). Twelve of these are in the amino terminus; 2 are in the region between IIS6 and IIIS1; and 7 are in the carboxy terminal tail. There are also 27 possible casein kinase phosphoration sites ((S/T]XX[D/E])(SEQ ID NO: 9): 12 in the amino terminus, 1 each in the loops IS6/IIS1 and IIIS6/IVS1, 4 in loop IIS6/IIIS1, I at the cytoplasmic end of IVS4, and 8 in the carboxy terminal tail. The high concentration of potential phosphorylation sites within several regions (the amino terminus, the II/III cytoplasmic loop and the C terminal tail) suggests that they may play roles in channel modulation by phosphorylation.

EXAMPLE XI

Comparison Of Sequences In Region Of The Proposed

Phenylalkylamine-Binding Domain

Figure 7:
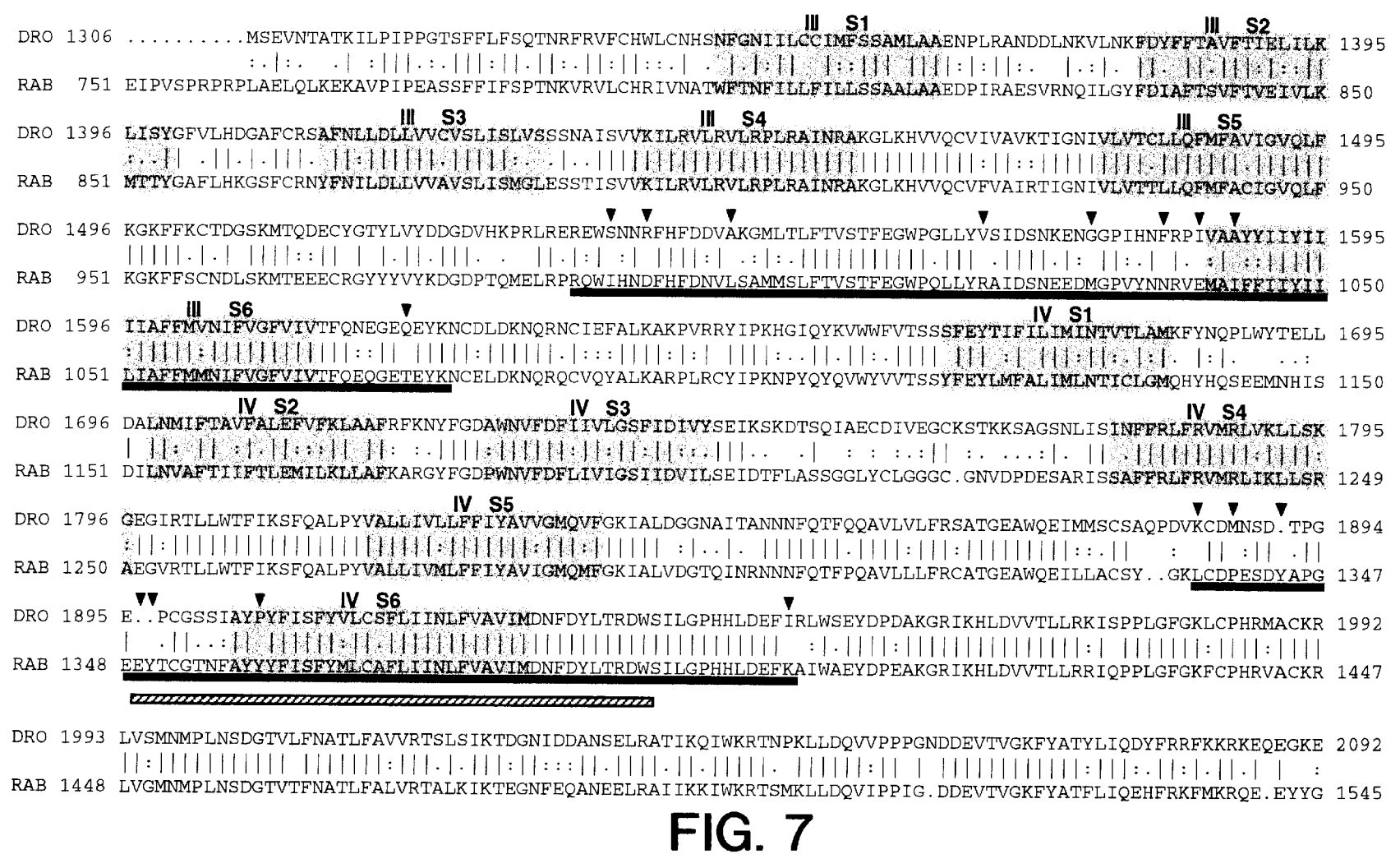

The phenylalkylamines constitute an important class of organic calcium channel blockers. A proposed binding site for phenylalkylamines has been localized to a 42 residue segment extending from E1349 to W1391 in the rabbit skeletal muscle subunit (Striessnig et al., (1990), *Proc. Natl. Acad. Sci. USA, vol.* 87, pp. 9108–9112, which disclosure is hereby incorporated by reference). This region (shown by hatched underline in FIG. 7) includes transmembrane domain IVS6 and adjacent intracellular and extracellular segments. Since phenylalkylamines exert their blocking effects from the inner surface of the membrane (Hescheler et al., (1982), *Pflügers Arch., vol.* 393, pp. 287–291; Affolter, J. and Coronado, R., (1986), *Biophys. J., vol.* 49, pp. 767–771, which disclosures are hereby incorporated by reference), the binding site for this class of blockers is thought to include the intracellular side of transmembrane segment IVS6 and the adjacent intracellular amino acids (Striessnig et al., (1990), *Proc. Natl. Acad. Sci. USA, vol.* 87, pp. 9108–9112, which disclosure is hereby incorporated by reference). In FIG. 7, starting with the intracellular amino acids fright end of the hatched underline) and proceeding to the left into the transmembrane region IVS6, it is apparent that this segment is completely conserved between *Drosophila* (upper line) and rabbit skeletal muscle (lower line) until about halfway through the transmembrane region where there is a weakly conserved change from alanine (A) in the rabbit to serine (S) in *Drosophila* and a highly conserved change from methionine (M) to valine (V). This high degree of conservation predicts that this *Drosophila* subunit should bind phenylalkylamines with high affinity.

EXAMPLE XII

Sequence Comparisons Relevant

To Dihydropyridine Sensitivity

Among the calcium channel $\alpha_1$ subunits listed in Table 2, the *Drosophila* subunit is most similar in sequence to those isoforms which have been shown to be dihydropyridine ("DHP") sensitive (indicated by+in this table). The four isoforms which are known to be insensitive to dihydropyridines (rat brain A and B, rabbit brain-1, and human N-type) show the least similarity to the *Drosophila* sequence. Another correlation is seen if the length of the cytoplasmic loop between repeats II and III is considered since all the known dihydropyridine-sensitive subunits have a short loop (134 to 150 amino acids in length) whereas the insensitive subunits have a much longer loop, ranging in length from 479 to 539. By this criterion, the *Drosophila* sequence would also fall into the DHP-sensitive category with a loop length of 129 amino acids.

A model for dihydropyridine-binding sites has been developed using photoaffinity labeling with dihydropyridines and has implicated the extracellular sides of transmembrane segments IIIS6 and IVS6 and the extracellular amino acids immediately adjacent to these transmembrane regions (Nakayama et al, (1991), *Proc. Natl. Acad. Sci. USA, vol.* 88, 9203–9207; Striessnig et al., (1991), *Proc. Natl. Acad. Sci. USA, vol.* 88, pp. 10769–10773; Catterall, W. A. and Striessnig, J., (1992), *TIPS, vol.* 13, pp. 256–262, which disclosures are hereby incorporated by reference). The segments involved are shown by the black underline in FIG. 7. In the portions of those two segments which include the left end (extracellular surface) of both S6 segments and the regions which extend to the left from the shaded transmembrane region, there are many amino acid differences (filled triangles above point to the changes) including: 8 nonconserved amino acid substitutions in the region adjacent to IIIS6 and extending into the extracellular side of S6. In region IVS6 and the adjacent extracellular amino acids, there are three nonconserved substitutions and two deletions (involving one and two amino acids) in the *Drosophila* sequence compared with the rabbit. The functional significance of these changes can be addressed by expression of this new subunit. The large number of changes in this region are consistent with the cloned channel being the dihydropyridine-insensitive, phenylalkylamine-binding activity which predominates in *Drosophila* head membranes (Greenberg et al., (1989), *Insect Biochem., vol.* 19, pp. 309–322, which disclosure is hereby incorporated by reference) even though the cloned channel falls into the sarstructural category as vertebrate dihydropyridine-sensitive subunits.

RESULTS

1. Invertebrate voltage-dependent calcium channels belong to the same multigene family as those in mammals:

It was clear that *Drosophila* had calcium channels in both neurons and muscles, but the pharmacological specificity of these channels was apparently different from that described for the vertebrate L-type channel from skeletal muscle (Pauron et al., (1987), *Biochemistry, vol.* 26, pp. 6311–6315; Greenberg et al., (1989), *Insect Biochem., vol.* 19, pp. 309–322; Pelzer et al., (1989), *EMBO J., vol.* 8, pp. 2365–2371; Glossman et al., (1991), *Br. J. Pharmacol., vol.* 102, pp. 446–452, which disclosures are hereby incorporated by reference) since the predominant channel in *Drosophila* heads was phenylalkylamine sensitive and dihydropyridine insensitive. In addition, other pharmacological differences were apparent in side-by-side comparisons of guinea pig skeletal muscle with *Drosophila* head extracts (Glossmann et al., (1991), *Br. J. Pharmacol., vol.* 102, pp. 446–452, which disclosure is hereby incorporated by reference). Using PCR with degenerate primers, we were able to rapidly cross species to isolate the first invertebrate calcium channel $\alpha_1$ subunit using information from vertebrate homologues. Our results indicate that despite pharmacological differences across species, neuronal invertebrate calcium channel $\alpha_1$ subunits belong to the same multigene family as mammalian $\alpha_1$ subunits. The subunit described here shows the same 4 repeat structure, each containing 6 transmembrane segments, that is the characteristic pattern for voltage-dependent calcium channels. This *Drosophila* sequence highlights regions of ai subunits which have been conserved across large evolutionary distances and therefore will facilitate the design of primer pairs for cloning homologous subunits from other invertebrate preparations of physiological importance or for cloning this subunit from pest neuronal invertebrates.

2. Analysis Of Dmca1D Suggests Heterogeneity Of Neuronal $\alpha_1$ Subunits:

In the tissues tested, the size of the mRNA on Northern blots is larger (9.5, 10.2, or 12.5 kb) than the cDNA sequence which we report here (8.0 kb). One possible explanation for this difference is that some untranslated regions are missing from the 5' and 3' ends. Indeed, we have not found a polyadenylation site on the 3' end. The finding of multiple in-frame stop codons in both the 5' and 3' untranslated regions provides strong evidence that the sequence presented here contains the full length open reading frame. The predominant forms seen on the Northern blot (FIG. 4) may represent major differences due to alternative splicing. Preliminary comparisons between genomic and cDNA using PCR have demonstrated the presence of at least 22 introns ranging in size from 55 base pairs to 3 kb (D.F. Eberl and D. Ren, unpublished observations, which are hereby incorporated by reference). We demonstrate here that alternative splicing occurs in at least two of these intron regions, but there are still many additional regions to be characterized. Depending on how the alternative splicing is done, it is possible to generate a large variety of mRNAs which will encode subunit forms with potentially different properties. Preliminary results suggest that this calcium channel subunit will show much heterogeneity due to alternative splicing. Indeed, the *Drosophila* sodium channel α-subunit has the potential to express more than 48 different splice variants and at least 19 of which have been identified to date (J.R. Thackery and B. Ganetzky, 1994, J. Neurosci, 14:2569–2578, personal communication, which is hereby incorporated by reference).

In view of the wide variety of potential alternative splice forms, it should be emphasized that the CDNA sequence shown in FIG. 2 represents the synthetic fusion of sequence information from two cDNA clones joined in a region of overlap within repeat III. Because of the large size of the full length message, it has not been possible to isolate a single cDNA clone that contains a complete open reading frame.

Using the Dmca1D cDNA as a probe in Northern blot analysis, there is more $\alpha_1$ subunit heterogeneity in heads than in bodies and legs since a prominent band at 10.2 kb is seen in heads and is not detected in bodies and legs. Only the 9.5 kb band is seen in all preparations. The heads would be enriched for nervous system compared to bodies and legs so the heterogeneity which we see in size of mRNA from heads could, in part, be due to functional diversity of channels expressed in neurons. This is interesting because it mirrors the greater heterogeneity observed by Leung, H. T. and Byerly, L., (1991), *J. Neurosci., vol.* 11, pp. 3047–3059, which is hereby incorporated by reference, in the physiological properties of neuronal compared to muscle calcium channels in primary cultures of neurons and muscle from *Drosophila* embryos.

Indeed, there could be much more heterogeneity than reflected by our Northern analysis with respect to the Dmca1D gene since alternatively spliced messages close in size would not be readily distinguished by Northern blot analysis of a message of this large size. PCR analysis of cDNA using strategically placed primers is a more sensitive approach. In the preliminary PCR experiment summarized in Table 1 we again see more heterogeneity in heads than in bodies and legs. Pelzer et al., (1989), *EMBO J., vol.* 8, 2365–2371, which disclosure is hereby incorporated by reference, found 8 different conductance levels for calcium channels when Drosophila head membranes were reconstituted into lipid bilayers. These conductances were found in single channel activity records and did not interconvert suggesting that each activity results from a different type of channel molecule. It is possible that these functionally distinct, nonconverting channel subtypes reflect, in part, the alternative splicing which we observe in Dmca1D expressed in *Drosophila* head mRNA. Functional expression of different splice variants of this cloned calcium channel subunit will allow us to define the molecular basis of these biophysically and pharmacologically distinct channel subtypes.

3. Relationship of Dmca1D To Previously Studied Calcium Channel Activities In Drosophila:

The clones used to construct the full length Dmca1D cDNA were all isolated from a head cDNA library. Thus, Dmca1D is a candidate for encoding the predominant phenylalkylamine-sensitive, dihydropyridine-insensitive binding activity found in *Drosophila* head membranes. The complete conservation of the phenylalkylamine-binding site in the Dmca1D deduced protein coupled with the numerous changes in the proposed dihydropyridine-binding domains are consistent with this suggestion. There is, however, one difficulty in equating Dmca1D with the previously characterized phenylalkylamine-binding activity in heads and that is that there is a substantial size difference between the deduced amino acid sequence of Dmca1D (219–276 kDa) and the photoaffinity labeled phenylalkylamine-binding components (136 and 27 kDa) (Greenberg et al., (1989), *Insect Biochem., vol.* 19, pp. 309–322; Pauron et al. (1987), *Biochemistry, vol.* 26, pp. 6311–6315, which disclosures are hereby incorporated by reference). Even if the two photoaffinity labeled components are actually part of the same protein, they still add up to only 166 kDa. There are several possible explanations for this size discrepancy. It could be due to alternative splicing and the predominantly expressed form of Dmca1D might be a different splice variant from the one presented here. Alternatively, it could be caused by a physiologically relevant proteolysis required for the maturation/activation of the subunit. The deduced *Drosophila* protein seems to be much larger in size than its vertebrate counterparts and it will be interesting to determine whether the long amino and carboxy tails are required for physiological function. The size difference might also be an artifact reflecting anomalous electrophoretic mobility of a large membrane protein on SDS gels or an artefact reflecting proteolysis during and/or following photoaffinity labeling. Indeed, the carboxy tail of the deduced protein sequence of Dmca1D contains a motif resembling the active site of thiol (cysteine) proteases. Thus, this subunit might catalyze its own cleavage. A final possibility is that the cloned subunit might be the product of a different gene from the one encoding the product seen by phenylalkylamine-photoaffinity labeling in head extracts. Although this seems unlikely in light of the high degree of conservation of the phenylalkylamine-binding site in Dmca1D, there is preliminary evidence for a distinct gene encoding another calcium channel $\alpha_1$ subunit in *Drosophila* (L.A. Smith and J.C. Hall, personal communication, which disclosure is hereby incorporated by reference).

Determination of the pharmacological properties of Dmca1D will have to await functional expression. Regardless of its pharmacological specificity, as the first neuronal invertebrate calcium channel subunit, the *Drosophila* $\alpha_1$ remains the evolutionarily most distant of the sequences described to date. Sequence comparisons coupled with functional studies of chimeric molecules should provide useful information concerning the nature of drug binding sites.

4. Using Genetics To Define Subunit Properties In The Organism:

One of the primary motivating factors in extending calcium channel molecular biology studies to *Drosophila* is the ability to use genetics to inactivate subunit genes singly and in combination in order to define functional roles within the organism. The chromosome mapping studies described here show that the newly cloned Dmca1D gene falls within a well-studied region of the *Drosophila* genome (see Ashburner et al., (1990), *Genetics, vol.* 126, pp. 679–694, which disclosure is hereby incorporated by reference). This region includes several lethal mutations. Recently, we have demonstrated that one of these embryonic lethal mutations causes a premature stop codon within the open reading frame of the Dmca1D gene (D.F. Eberl, D. Ren, G. Feng and L.M. Hall, unpublished observations, which disclosures are hereby incorporated by reference). Genetic analysis of double mutants from this and other calcium channel subunits will allow us to define which subunits actually interact in vivo. Transformation rescue experiments (Spradling, A. C., (1986), In: *Drosophila: A Practical Approach*, Roberts, D. B., ed., IRL Press, Washington, D.C., pp. 175–197, which disclosure is hereby incorporated by reference) using this $\alpha_1$ subunit will allow us to test whether there is functional overlap among the different genes encoding homologous subunits and to determine the role in vivo of the different splice variants of this gene.

Although the invention has been described in detail for the purpose of illustration, it is understood that such detail is solely for that purpose, and variations can be made therein by those skilled in the art without departing from the spirit and scope of the invention which is described by the following claims.

TABLE 1

RT-PCR followed by restriction enzyme digestion reveals more DmcalD message heterogeneity in heads than in bodies or legs

| Region amplified by RT-PCR | Source of mRNA | mRNA isoforms present | Diagnostic restriction enzyme |
|---|---|---|---|
| Cytoplasmic loop between II & III (bases 3830–4033) | Heads | (1)A, D | Hinf I |
| | Bodies | A | Hinf I |
| | Legs | A | Hinf I |
| IIIS3 to Loop between IIIS5 & S6 (bases 4251–4635) | Heads | C, D | Pst I or RSA I |
| | Bodies | C | Pst I or Rsa I |
| | Legs | D | Pst I or Rsa I |

(1)A, C, D refer to splice forms found in different cDNA clones (A = W8A, C = SH22C, D = SH22D) in the regions indicated by open boxes in the SH22D diagram in FIG. 1B. Although the alternative forms were similar in size, they could be distinguished in the PCR amplification products following digestion with the indicated restriction enzymes.

TABLE 2

Comparison of a Drosophila calcium channel $\alpha_1$ subunit with the vertebrate $\alpha_1$ subunits at amino acid level.

| DHP Sensitivity | Similarity % | Identity % | Loop II/III* | References |
|---|---|---|---|---|
| + Rat Brain-D | 78.3 | 64.2 | 134 | Hui et al., 1991 |
| + Rabbit Skeletal Muscle | 72.4 | 56.1 | 138 | Tambe et al., 1987 |
| + Human Brain | 71.3 | 55.5 | 134 | Williams et al, 1992b |
| + Rabbit Lung | 70.2 | 54.1 | 125 | Biel et al., 1990 |
| + Carp Skeletal Muscle | 70.0 | 51.7 | 139 | Grabner et al., 1991 |
| + Rat Brain-C | 69.9 | 54.1 | 150 | Snutch et al., 1991 |
| + Rat Heart | 69.6 | 53.3 | 147 | Mikami et al., 1989 |
| + Rat Aorta | 68.7 | 53.0 | 147 | Koch et al., 1990 |
| − Rat Brain-A | 65.2 | 45.1 | 479 | Starr et al., 1991 |
| − Rabbit Brain-1 | 64.5 | 44.2 | 539 | Mori et al., 1991 |
| − Rat Brain-B | 63.4 | 43.7 | 438 | Dubel et al., 1992 |
| − Human N-type | 63.4 | 42.7 | 451 | Williams et al., 1992a |
| Na+ channel (Drosophila) | 58.9 | 30.5 | | Loughney et al., 1989 |
| Na+ channel (Rat skel. muscle) | 57.9 | 29.6 | | Trimmer et al., 1989 |

*This is the cytoplasmic loop between IIS6 and IIS1. In DmcalD the length of this loop is 129 amino acids.

TABLE 3

Comparison of alternating positive charges in S4 transmembrane domains in calcium channel $\alpha_1$ subunits.

| | Numbers of positively charged amino acids in S4 domain | | | |
|---|---|---|---|---|
| Clone Source† | #KRT | KRT | KRT | KRT |
| Drosophila head (DmcalD) | 145 | 235 | 156 | 235 |
| Carp skeletal muscle | 145 | 145 | 156 | 145 |
| Rabbit skeletal muscle | 145 | 235 | 156 | 145 |
| Human brain | 145 | 145 | 156 | 145 |
| Rat brain-D | 145 | 145 | 156 | 145 |
| Rat brain-C | 145 | 145 | 156 | 145 |
| Rat aorta | 145 | 145 | 156 | 145 |
| Rabbit heart | 145 | 145 | 156 | 145 |
| Rat brain-B | 101 | 213 | 235 | 123* |
| Rabbit brain-1 | 145 | 235 | 246 | 134* |
| Rat brain-A | 145 | 235 | 246 | 134* |

†The references for sequences used in this comparison are given in Table 2.
K = lysine; R - arginine; T - total positively charged side chains placed every 3–4 residues.
*For this domain, these $\alpha_1$ sununits have a glutamine (Q) in the position occupied by arginine (R) or lysine (K) in other species. This position is the fourth amino acid from the previous positively charged amino acid and falls near the cytoplasmic end of this transmembrane α-helix. There is an arginine residue in the immediately preceding position for each of these proteins.

TABLE 4

Tufty-Kretsinger (TK) test for EF hand: Comparison of the Drosophila sequence with vertebrate sodium and calcium channel α1 subunits (taken, in part, from Babitch, 1990).†

Vertices:
TK TEST:
Na+ channel $\alpha_1$ subunit upstream sequences

| | | | | |
|---|---|---|---|---|
| Eel | 1588 | M F D E T W H K F D V H G T Q F L D Y N D L P R F V N A L | 1616 | 9(12) |
| Rat BrI | 1607 | M F Y E V W E K F D P D A T Q F M E F E K L S Q F A A A L | 1535 | 10(13) |
| Rat BRII | 1797 | M F Y E V W E K F D P D A T Q F I E F C K L S D F A A A L | 1825 | 11(13) |
| Rat BRIII | 1743 | M F Y E V W E K F D P D A T Q F I E F C K L S D F A A A L | 1771 | 11(13) |
| Rat Heart | | M F Y E I W E K F D P E A T Q F I E Y L A L S D F A D A L | | 11(13) |
| Rat µ1 | 1612 | M F Y E T W E K F D P D A T Q F I D Y S R L S D F V T D L | 1840 | 11(12) |

Na+ channel $\alpha_1$ subunit downstream sequences:

| | | | | |
|---|---|---|---|---|
| Eel | 1642 | K I S Y L D V L L A V T Q E V L G D T T E M E A M R L S I | 1670 | 10(11) |
| Rat µ1 | 1666 | K I H C L D I L F A L T K E V L G D S G E M D A L K Q T M | 1694 | 10(11) |

TABLE 4-continued

Tufty-Kretsinger (TK) test for EF hand: Comparison of the Drosophila sequence with vertebrate sodium and calcium channel α1 subunits (taken, in part, from Babitch, 1990).†

Ca$^{2+}$ channel α1 subunit sequences:

| | | | |
|---|---|---|---|
| Rat Brain-C | E F K R I W A E Y D P E A K G R I K H L D V V T L L R R I | | 11(14) |
| Carp Skel. | E F K K I W A E Y D P E A T G R I K H L D V V T L L R R I | | 11(14) |
| Human Brain | E F K R I W S E Y D P E A K G R I K H L D V V T L L R R I | | 11(14) |
| Rabbit Skel. | E F K A I W A E Y D P E A K G R I K H L D V V T L L R R I | | 11(14) |
| Rat Brain-D | E F K R I W S E Y D P E A K G R I K H L D V V T L L R R I | | 11(14) |
| DmcalD | 1946 E F I R L W S E Y D P D A K G R I K H L D V V T L L R K I | 1974 | 11(14) |

†Footnotes for Table 4

The X, Y, Z, –Y, –X, –Z in the "Vertices" row refer to the vertices of the calcium coordination octahedron in the EF hand. These positions are often occupied by amino acids containing an oxygen atom. The TK TEST row indicates the positions of the 16 test residues where E is glutainic acid, n is a hydrophobic residue (F, phenylalanine; I, isoleucine; L, leucine; M, methionine; V, valine) and * is an oxygen containing residue (D, aspartic acid; N, asparagine; E, glutamic acid; Q, glutamine; S, serine; T, threonine). Each seqtience is scored 1 for the presence and 0 for the absence of a test residue with 16 matches being the highest possible score. In the "Scores" column the first number is the raw score (and is tbe sum of the single underlined amino acids). The number within the parentheses is the score if conservative substitutions are allowed (and is the sum of the single and double underlined amino acids). The references for calcium channel sequences are given in Table 2. The sodium channel references are: eel (Noda et al, 1984), rat brain I and II (Noda et al., 1986), rat brain III (Kayano et al., 1988), rat heart (Rogart et al., 1989), rat skeletal μ1 (Trimmer et al., 1989). Br = brain; Skel = skeletal muscle

TABLE 5

Ion selectivity filter of ion channels †

| | | Repeat I | | Repeat II |
|---|---|---|---|---|
| Calcium channel | Consensus | QCiTmEgWTDvLY | Consensus | QilTGEdWnsvMY |
| | Drosophila | QCVTLEGWTDVLY | Drosophila | QIMTGEDWNAVMY |
| | Carp Skel | QCITTESWTDVLY | Carp Skel | QVLTGEEWDSIMY |
| | Rab. Skel | QVLTGEDWNSVMY | Rab. Skel | QCITMEGWTDVLY |
| | Human Br | QCITMEGWTDVLY | Human Br | QILTGEDWNAVMY |
| | Rat Br-D | QCITMEGWTDVLY | Rat Br-D | QILTGEDWNAVMY |
| | Rat Br-C | QCITMEGWTDVLY | Rat Br-C | QILTGEDWNSVMY |
| | Rat Aorta | QCITMEGWTDVLY | Rat Aorta | QILTGEDWNSVMY |
| | Rab. Heart | QCITMEGWTDVLY | Rab. Heart | QILTGEDWNSVMY |
| | Rat Br-B | QCITMEGWTDVLY | Rat Br-B | QILTGEDWNSVMY |
| | Rab. Br-1 | QCITMEGWTDVLY | Rab. Br-1 | QILTGEDWNSVMY |
| | Rat Br-A | QCITMEGWTDVLY | Rat Br-A | QILTGEDWNSVMY |
| Sodium channel | Consensus | RLMTQDyWEnLYQ | Consensus | RvLCGEWIEtMWD |
| | para | RLMTQDFWEDLYQ | para | RVLCGEWIESMWD |
| | Rat BrII | RLMTQDFWEDLYQ | Rat BrII | RVLCGEWIESMWD |
| | Rat BrIII | RLMTQDFWEDLYQ | Rat BrIII | RVLCGEWIESMWD |
| | Rat Heart | RLMTQDFWEDLYQ | Rat Heart | RILCGEWIESMWD |
| | Rat Skel μ1 | RLMTQDFWEDLYQ | Rat Skel μ1 | RILCGEWIESMWD |
| | Eel | RLMTQDFWEDLYQ | Eel | RALCGEWIESMWD |
| | | SS2     SS2 | | SS1     SS2 |
| | | Repeat III | | Repeat IV |
| Calcium channel | Consensus | TvSTfEGWPeILY | Consensus | RcATGEaWqeiml |
| | Drosophila | TVSTFEGWPGLLY | Drosophila | RSATGEAWEIMM |
| | Carp Skel | TISTFEGWPEILY | Carp Skel | RVATGEQWPKVIL |
| | Rab. Skel | TVISTFEGWPEILY | Rab. Skel | RCATGEQWPKVIL |
| | Human Br | TVISTFEGWPEILY | Human Br | RCATGEQWPKVIL |
| | Rat Br-D | TVISTFEGWPEILY | Rat Br-D | RCATGEQWPKVIL |
| | Rat Br-C | TVISTFEGWPEILY | Rat Br-C | RCATGEQWPKVIL |
| | Rat Aorta | TVISTFEGWPEILY | Rat Aorta | RCATGEQWPKVIL |
| | Rab. Heart | TVISTFEGWPEILY | Rab. Heart | RCATGEQWPKVIL |
| | Rat Br-B | TVISTFEGWPEILY | Rat Br-B | RSATGEQWPKVIL |
| | Rab. Br-1 | TVISTFEGWPEILY | Rab. Br-1 | RSATGEQWPKVTL |
| | Rat Br-A | TVISTFEGWPEILY | Rat Br-A | RSATGEQWPKVIL |
| Sodium channel | Consensus | QVaTFKGWMdIMy | Consensus | qitTSAGWDGlLa |
| | para | QVATFKGWIQIMN | para | QMSTSAGWDGVLD |
| | Rat BrII | QVATFKGWIQIMN | Rat BrII | QISTSAGWDGVLD |
| | Rat BrIII | QVATFKCWIQIMN | Rat BrIII | QISTSAGWDGVLD |
| | Rat Heart | QVATFKCWIQIMN | Rat Heart | QISTSAGWDGVLD |
| | Rat Skel μ1 | QVATFKGWMDIMY | Rat Skel μ1 | EITFSAGWDGLLN |
| | Eel | QVSTFKGWMDIMY | Eel | EITTSAGWDGLLL |
| | | SS1     SS2 | | SS1     SS2 |

What is claimed is:

1. An isolated gene comprising a DNA molecule encoding an invertebrate neuronal calcium channel $\alpha_1$ subunit from *Drosophila melanogaster*.

2. The gene according to claim 1, wherein said DNA is cDNA.

3. The gene according to claim 1, wherein said DNA molecule encodes the amino acid sequence according to SEQ. ID. NO. 2.

4. The gene according to claim 1, wherein said DNA molecule has the nucleotide sequence corresponding to SEQ. ID. NO. 1.

5. A gene comprising a DNA molecule according to claim 1, linked to a heterologous DNA.

6. A method of expressing a functional invertebrate calcium channel, comprising:
   transforming a host cell with the gene according to claims 1, 2, 3, 4, 5; and
   culturing said host cell under conditions such that said gene is expressed, thereby forming a functional channel.

7. A vector comprising a DNA sequence encoding an invertebrate neuronal calcium channel $\alpha_1$ subunit from *Drosophila melanogaster*.

8. The vector according to claim 7, wherein said vector is selected from the group consisting of a plasmid, virus and bacteriophage.

9. The vector according to claim 7, wherein said DNA sequence is inserted into said vector in proper orientation and correct reading frame such that said DNA sequence may be expressed by a cell transformed with said vector.

10. The vector according to claim 7, wherein said DNA sequence is operatively linked to a promoter sequence.

11. A cell transformed with the vector of claim 7.

12. A composition of matter useful for expression of a calcium channel $\alpha_1$ subunit from *Drosophila melanogaster* comprising the vector of claim 7, wherein the DNA is operably linked to a control sequence.

* * * * *